(12) United States Patent
McCormick et al.

(10) Patent No.: US 7,803,828 B2
(45) Date of Patent: *Sep. 28, 2010

(54) FUNCTIONALLY SELECTIVE ALPHA2C ADRENORECEPTOR AGONISTS

(75) Inventors: Kevin D. McCormick, Basking Ridge, NJ (US); Christopher W. Boyce, Flemington, NJ (US); Robert G. Aslanian, Rockaway, NJ (US); Neng-Yang Shih, Warren, NJ (US); Salem Fevrier, Cranford, NJ (US); Pietro Mangiaracina, Monsey, NY (US); Chia-Yu Huang, West Windsor, NY (US); Bo Liang, Lawrenceville, NJ (US); Rong-Qiang Liu, Kendall Park, NJ (US); Huagang Lu, Plainsboro, NJ (US)

(73) Assignee: Schering-Plough Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/508,458

(22) Filed: Aug. 23, 2006

(65) Prior Publication Data

US 2007/0099872 A1 May 3, 2007

Related U.S. Application Data

(60) Provisional application No. 60/711,398, filed on Aug. 25, 2005.

(51) Int. Cl.
*A01N 43/50* (2006.01)
*C07D 233/00* (2006.01)

(52) U.S. Cl. .................................... 514/397; 548/300.1
(58) Field of Classification Search ....................... None
See application file for complete search history.

(56) References Cited

U.S. PATENT DOCUMENTS

| 5,977,134 A * | 11/1999 | Ciccarone et al. ........... 514/307 |
| 6,673,337 B2 | 1/2004 | Olejnik et al. |
| 7,399,868 B2 | 7/2008 | Heidelbaugh et al. |
| 2003/0087962 A1 | 5/2003 | Demopulos et al. |

FOREIGN PATENT DOCUMENTS

WO    WO 97/12874    4/1997

OTHER PUBLICATIONS

Heidelbaugh et al., caplus an 2006:299467.*
Mizuno et al., Bioorg. & med. Chem. Lett, 14(2004), 5959-5962.*
Medical Dictionary Online-, 5-HT1 Agonists, www.online-medical-dictionary.org,—2 Pages.
Siemens, What Are Natriuretic Peptides?, www.chestpainperspectwes.com,—5 Pages.

* cited by examiner

*Primary Examiner*—Golam M. M. Shameem
*Assistant Examiner*—Sun Jae Y Loewe
(74) *Attorney, Agent, or Firm*—H. Eric Fischer; Gerard M. Devlin; Mark W. Russell

(57) ABSTRACT

In its many embodiments, the present invention provides a novel class of indolines as inhibitors of α2C adrenergic receptor agonists, methods of preparing such compounds, pharmaceutical compositions containing one or more such compounds, methods of preparing pharmaceutical formulations comprising one or more such compounds, and methods of treatment, prevention, inhibition, or amelioration of one or more conditions associated with the α2C adrenergic receptors using such compounds or pharmaceutical compositions.

17 Claims, No Drawings

FUNCTIONALLY SELECTIVE ALPHA2C ADRENORECEPTOR AGONISTS

RELATED APPLICATIONS

This application claims priority to provisional application U.S. Ser. No. 60/711,398, filed on Aug. 25, 2005, herein incorporated by reference.

FIELD OF THE INVENTION

The present invention relates to indoline compounds useful as α2C adrenergic receptor agonists, methods for making the compounds, pharmaceutical compositions containing the compounds, and methods of treatment and prevention using the compounds and compositions to treat disease states such as congestion (including nasal), migraine, congestive heart failure, cardiac ischemia, glaucoma, pain and psychotic disorders without substantial adverse side effects associated with α2A receptor agonist treatments.

BACKGROUND OF THE INVENTION

The initial classification of adrenergic receptors into α- and β-families was first described by Ahlquist in 1948 (Ahlquist R P, "A Study of the Adrenergic Receptors," Am. J. Physiol. 153:586-600 (1948)). Functionally, the α-adrenergic receptors were shown to be associated with most of the excitatory functions (vasoconstriction, stimulation of the uterus and pupil dilation). β-adrenergic receptors were implicated in vasodilation, bronchodilation and myocardial stimulation (Lands et al., "Differentiation of Receptor Systems Activated by Sympathomimetic amines," Nature 214:597-598 (1967)). Since this early work, α-adrenergic receptors have been subdivided into a 1- and α2-adrenergic receptors. Cloning and expression of α-adrenergic receptors have confirmed the presence of multiple subtypes of both α1-(α1A, α1B, α1D) and α2-(α2A, α2B, α2C) adrenergic receptors (Michel et al., "Classification of $α_1$-Adrenoceptor Subtypes," Naunyn-Schmiedeberg's Arch. Pharmacol, 352:1-10 (1995); Macdonald et al., "Gene Targeting—Homing in on $α_2$-Adrenoceptor-Subtype Function," TIPS, 18:211-219 (1997)).

Current therapeutic uses of α-2 adrenergic receptor drugs involve the ability of those drugs to mediate many of the physiological actions of the endogenous catecholamines. There are many drugs that act on these receptors to control hypertension, intraocular pressure, eye reddening and nasal congestion and induce analgesia and anesthesia.

α2 adrenergic receptors can be found in the rostral ventrolateral medulla, and are known to respond to the neurotransmitter norepinephrine and the antihypertensive drug clonidine to decrease sympathetic outflow and reduce arterial blood pressure (Bousquet et al., "Role of the Ventral Surface of the Brain Stem in the Hypothesive Action of Clonidine," Eur. J. Pharmacol., 34:151-156 (1975); Bousquet et al., "Imidazoline Receptors: From Basic Concepts to Recent Developments," 26:S1-S6 (1995)). Clonidine and other imidazolines also bind to imidazoline receptors (formerly called imidazoline-guanidinium receptive sites or IGRS) (Bousquet et al., "Imidazoline Receptors: From Basic Concepts to Recent Developments," 26:S1-S6 (1995)). Some researchers have speculated that the central and peripheral effects of imidazolines as hypotensive agents may be related to imidazoline receptors (Bousquet et al., "Imidazoline Receptors: From Basic Concepts to Recent Developments," 26:S1-S6 (1995); Reis et al., "The Imidazoline Receptor: Pharmacology, Functions, Ligands, and Relevance to Biology and Medicine," Ann. N.Y. Acad. Sci., 763:1-703 (1995).

Compounds having adrenergic activity are well-known in the art, and are described in numerous patents and scientific publications. It is generally known that adrenergic activity is useful for treating animals of the mammalian species, including humans, for curing or alleviating the symptoms and conditions of numerous diseases and conditions. In other words, it is generally accepted in the art that pharmaceutical compositions having an adrenergic compound or compounds as the active ingredient are useful for treating, among other things, glaucoma, chronic pain, migraines, heart failure, and psychotic disorders.

For example, published PCT application WO 02/076950 discloses compounds having α2 agonist activity of the following general formula:

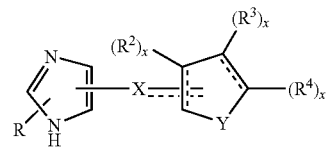

Another class of compounds having α2-agonist properties is disclosed in U.S. Pat. No. 5,658,938, and has the following general formula:

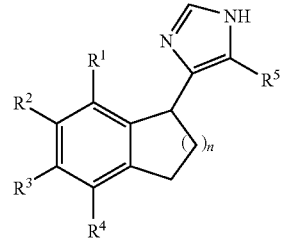

wherein n=1-2, $R^1$-$R^3$ represent hydrogen, halogen hydroxy, alkyl or alkoxy, and $R^5$ is hydrogen or alkyl.

Another class of compounds reported to have affinity for α2 receptors includes the following two compounds (Bagley et. al., Med. Chem. Res. 1994, 4:346-364):

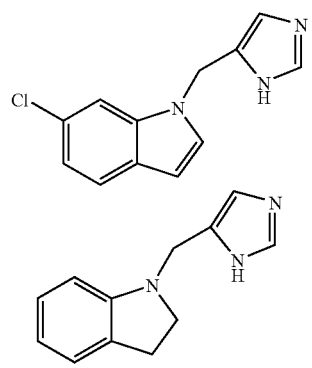

It is also known that compounds having adrenergic activity, such as α2A agonists, may be associated with undesirable side effects. Examples of such side effects include hyper- and hypotension, sedation, locomotor activity, and body temperature variations.

It has been discovered in accordance with the present invention that adrenergic compounds that act selectively, and preferably even specifically, as agonists of the α2C or the α2B/α2C (hereinafter referred to as α2C or α2B/2C) receptor subtypes in preference over the α2A receptor subtype, with the adrenergic compounds that are functionally selective agonists of the α2C or the α2B/2C receptor subtype in preference over the α2A receptor subtype, possess desirable therapeutic properties associated with adrenergic receptors but without having one or more undesirable side effects such as changes in blood pressure or sedation. For the purposes of the present invention, a compound is defined to be a specific or at least functionally selective agonist of the α2C receptor subtype over the α2A receptor subtype if the compound's efficacy at the α2C receptor is $\geq 30\%$ $E_{max}$ (GTPγS assay) and its efficacy at the α2A receptor is $\leq 30\%$ $E_{max}$ (GTPγS assay).

There is a need for new compounds, formulations, treatments and therapies to treat diseases and disorders associated with α2C adrenergic receptors while minimizing adverse side effects. Further, there is a need to develop compounds that are functionally selective for the α2C or the α2B/2C receptor subtype with respect to the α2A receptor subtype. It is, therefore, an object of this invention to provide compounds useful in the treatment or prevention or amelioration of such diseases and disorders.

SUMMARY OF THE INVENTION

In its many embodiments, the present invention provides a novel class of heterocyclic compounds as functionally selective α2C adrenergic receptor agonists, or metabolites, stereoisomers, salts, solvates or polymorphs thereof, methods of preparing such compounds, pharmaceutical compositions comprising one or more such compounds, methods of preparing pharmaceutical formulations comprising one or more such compounds, and methods of treatment, prevention, inhibition or amelioration of one or more conditions associated with α2C receptors using such compounds or pharmaceutical compositions.

In one aspect, the present application discloses a compound, or pharmaceutically acceptable salts or metabolites, solvates or polymorphs of said compound, said compound having the general structure shown in Formula I:

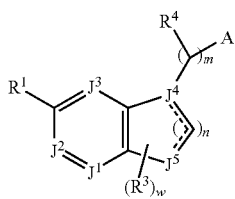

Formula I wherein:

A is a 5-membered heterocyclic ring containing 1-3 heteroatoms, and is optionally substituted with at least one $R^5$;

$J^1$, $J^2$, and $J^3$ are independently —N—, —N(O)— or —C($R^2$)—;

$J^4$ is C or N;

$J^5$ is —C($R^6$)— or —N($R^6$)—;

----- is a single or double bond;

$R^1$ is selected from the group consisting of —$(CH_2)_q YR^7$, —$(CH_2)_q NR^7 YR^7$, —$(CH_2)_q NR^7 R^7$, —$(CH_2)_q OYR^7$, —$(CH_2)_q ON=CR^7 R^7$, —$P(=O)(OR^7)(OR^7)$, —$P(=O)(NR^7 R^7)_2$, and —$P(=O)R^8_2$;

Y is selected from the group consisting of a bond, —C(=O)—, —C(=O)NR^7—, —C(=O)O—, —C(=NR^7)—, —C(=NOR^7)—, —C(=NR^7)NR^7—, —C(=NR^7)NR^7O—, —S(O)_p—, —SO_2NR^7—, and —C(=S)NR^7—;

$R^2$ is independently selected from the group consisting of H, —OH, halo, —CN, —$NO_2$, —$SR^7$, —$NR^7 R^7$, —$(CH_2)_q YR^7$, —$(CH_2)_q NR^7 YR^7$, —$(CH_2)_q OYR^7$, —$(CH_2)_q ON=CR^7 R^7$, —$P(=O)(OR^7)(OR^7)$, —$P(=O)NR^7 R^7$, and —$P(=O)R^8_2$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^3$ is independently selected from the group consisting of H and (=O), and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$, provided that when w is 3, no more than 2 of the $R^3$ groups may be (=O);

$R^4$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

$R^5$ is independently selected from the group consisting of H, halo, —OH, —CN, —$NO_2$, —$NR^7 R^7$, and —$SR^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —$NO_2$, —$NR^7 R^7$, and —$S(O)_P R^7$ substituents;

$R^6$ is independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —$NO_2$, —$NR^7 R^7$, and —$SR^7$ substituents, and —$C(=O)R^7$, —$C(=O)OR^7$, —$C(=O)NR^7 R^7$, —$SO_2 R^7$ and —$SO_2 NR^7 R^7$;

$R^7$ is independently selected from the group consisting of H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —$NO_2$, —$N(R^{11})_2$ and —$SR^{11}$ substituents;

$R^{7'}$ is independently selected from the group consisting of H and alkyl, alkenyl, alkynyl, cycloalkyl, aryl, arylalkyl, heteroaryl, and heteroarylalkyl groups, each of which is optionally substituted with at least one of halo, —OH, —CN, —$NO_2$, —$N(R^{11})_2$, and —$SR^{11}$ substituents; or $R^7$ and $R^{7'}$ together with the nitrogen atom to which they are attached form a 3- to 8-membered heterocyclyl, heterocyclenyl or heteroaryl ring having, in addition to the N atom, 1 or 2 additional hetero atoms selected from the group consisting of O, N, —$N(R^9)$— and S, wherein said rings are optionally substituted by 1 to 5 independently selected $R^5$ moieties, $R^8$ is independently selected from the group consisting of alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —$NO_2$, —$N(R^{11})_2$, and —$SR^{11}$ substituents $R^9$ is independently selected from the group consisting of H, —C(O)—$R^{10}$, —C(O)—$OR^{10}$, and —S(O)$_p$—$OR^{10}$ and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —$SR^{11}$ substituents; and $R^{10}$ is selected from the group consisting of alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N($R^{11}$)$_2$, and —$SR^{11}$ substituents;

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

m is 1-5;

n is 1-3;

p is 0-2;

q is 0-6; and w is 1-3;

with the following provisos:

(a) if $J^1$-$J^3$ are —C(H)—, $R^1$ is —(CH$_2$)$_q$OY$R^7$, q is 0, and A is unsubstituted imidazolyl, then Y is other than a bond;

(b) if $J^1$-$J^3$ are —C(H)—, $R^1$ is —(CH$_2$)$_q$Y$R^7$, q is 0, and A is unsubstituted imidazolyl, then Y is other than a bond;

(c) if $J^4$ is N, then $J^5$ is —C($R^6$)—; and (d) if $J^4$ is C, then $J^5$ is —N($R^6$)—.

The compounds of Formula I can be useful as α2C adrenergic receptor agonists, and can be useful in the treatment and prevention of allergic rhinitis, congestion (including, but not limited to nasal congestion), migraine, congestive heart failure, cardiac ischemia, glaucoma, stress-induced urinary incontence, neuronal damage from ischemia and psychotic disorders. Further, the compounds of formula I can be useful in the treatment of pain (both chronic and acute), such as pain that is caused by inflammation, neuropathy, arthritis (including rheumatoid arthritis), diabetes (e.g., diabetes mellitus or diabetes insipidus), or an unknown origin. Other pain that can be treated is nociceptive pain and pain that is visceral in origin or pain that is secondary to inflammation or nerve damage in other diseases or diseases of unknown origin.

Alternatively, the present invention provides for a method for the treatment of congestion in a mammal in need thereof which comprises administering to a mammal an effective dose of at least one compound having adrenergic activity wherein said compound is a functionally selective agonist of the α2c receptor.

A further embodiment of the present invention is a method for the treatment of congestion in a mammal in need thereof which comprises administering to a mammal an effective dose of at least one compound having adrenergic activity wherein said compound is a functionally selective agonist of the α2C receptor, wherein the selective agonist of the α2c receptor has an efficacy that is greated than or equal to 30% $E_{max}$ when assayed in the GTPγS assay and its efficacy at the α2A receptor is ≦30% $E_{max}$ (GTPγS assay).

Another embodiment of the present invention is a method for the treatment of congestion in a mammal in need thereof without modifying the blood pressure at therapeutic doses which comprises administering to the mammal an effective dose of at least one compound having adrenergic activity wherein said compound is a selective agonist of the α2C receptor.

DETAILED DESCRIPTION

In an embodiment, the present invention discloses certain heterocyclic compounds which are represented by structural Formula I, or a pharmaceutically acceptable salt or solvate thereof, wherein the various moieties are as described above.

In one embodiment, if $J^1$-$J^3$ are —C(H)—, $R^1$ is —(CH$_2$)$_q$OY$R^7$, q is 0, and A is unsubstituted imidazolyl, then Y is other than a bond.

In another embodiment, if $J^1$-$J^3$ are —C(H)—, $R^1$ is —(CH$_2$)$_q$Y$R^7$, q is 0, and A is unsubstituted imidazolyl, then Y is other than a bond; and In another embodiment, if $J^4$ is N, then $J^5$ is —C($R^6$)—;

In another embodiment, if $J^4$ is C, then $J^5$ is —N($R^6$)—;

In another embodiment, $J^1$-$J^3$ are each —C($R^2$)—;

In another embodiment, A is an 5-membered heterocyclic ring containing at least one ring nitrogen.

In another embodiment, $R^1$ is selected from —(CH$_2$)$_q$Y$R^7$, —(CH$_2$)$_q$N$R^7$Y$R^{7'}$, —(CH$_2$)$_q$N$R^7$$R^{7'}$, —(CH$_2$)$_q$OY$R^7$, —(CH$_2$)$_q$ON=C$R^7$$R^{7'}$, —P(=O)(O$R^7$)(O$R^{7'}$), —P(=O)(N$R^7$$R^{7'}$), and —P(=O)$R^8{}_2$;

In another embodiment, Y is selected from a bond, —C(=O)—, —C(=O)N$R^7$—, —C(=O)O—, —C(=N$R^7$)—, —C(=NO$R^7$)—, —C(=N$R^7$)N$R^7$—, —C(=N$R^7$)N$R^7$O—, —S(O)$_p$—, —SO$_2$N$R^7$—, and —C(=S)N$R^7$—;

In another embodiment, $R^2$ is independently selected from the group consisting of H, —OH, halo, —CN, —NO$_2$, —S$R^7$, —N$R^7$$R^{7'}$, —(CH$_2$)$_q$Y$R^7$, —(CH$_2$)$_q$N$R^7$Y$R^{7'}$, —(CH$_2$)$_q$OY$R^7$, —(CH$_2$)$_q$ON=C$R^7$$R^{7'}$, —P(=O)(O$R^7$)(O$R^{7'}$), —P(=O)N$R^7$$R^{7'}$, and —P(=O)$R^8{}_2$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

In another embodiment, $R^3$ is independently selected from H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

In another embodiment, $R^4$ is independently selected from H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups optionally substituted with at least one $R^5$;

In another embodiment, $R^5$ is independently selected from H, halo, —OH, —CN, —NO$_2$, —N$R^7$$R^{7'}$, and —S$R^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —N$R^7$$R^{7'}$, and —S(O)$_p$$R^7$ substituents;

In another embodiment, $R^6$ is independently selected from H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —N$R^7$$R^{7'}$, and —S$R^7$ substituents, and —C(=O)$R^7$, —C(=O)O$R^7$, —C(=O)N$R^7$$R^{7'}$, —SO$_2$$R^7$ and —SO$_2$—N$R^7$$R^{7'}$;

In another embodiment, $R^7$ or $R^{7'}$ is independently selected from H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N(R$^{11}$)$_2$, and —SR$^{11}$ substituents In another embodiment, R$^7$ and R$^{7'}$ together with the N atom to which they are attached form a aziridine, azetidine, pyrrole, pyrrolidine, piperidine, piperazine or morpholine ring, each of which are optionally substituted by R$^5$.

In another embodiment, R$^5$ is independently selected from alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N(R$^{11}$)$_2$, and —SR$^{11}$ substituents In another embodiment, m is 1.
In another embodiment, n is 1.
In another embodiment, p is 0-2.
In another embodiment, q is 0-3.
In another embodiment, A is imidazolyl.
In another embodiment, J$^4$ is N.
In another embodiment, J$^5$ is —N(R$^6$)—.

In another embodiment, the present invention discloses compounds which are represented by structural formulae II-V or a pharmaceutically acceptable salt, solvate or ester thereof, wherein the various moieties are as described above:

Formula II

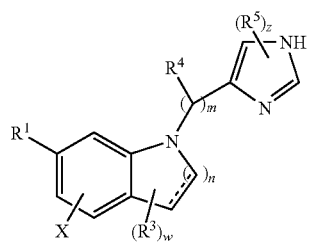

Formula III

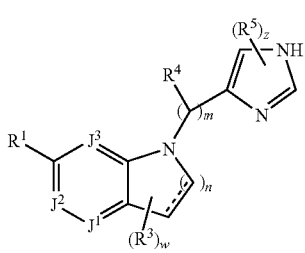

Formula IV

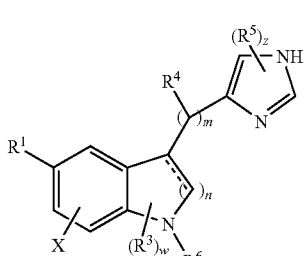

Formula V

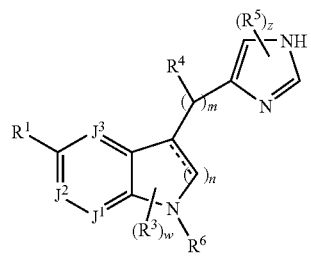

wherein X is halo or H and z is 0-3.

An inventive group of compounds is shown below:

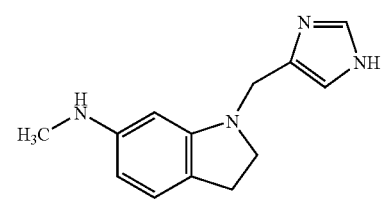

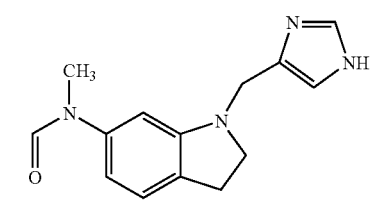

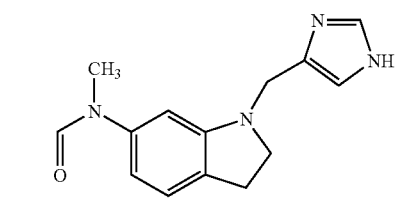

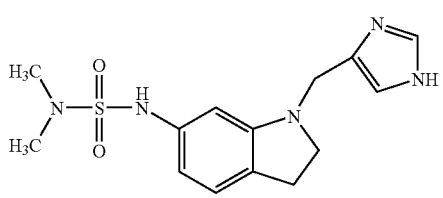

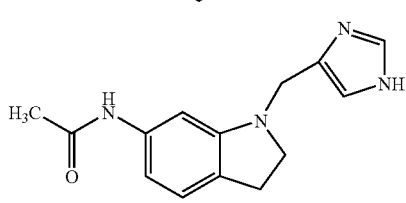

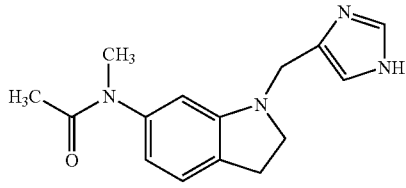

-continued
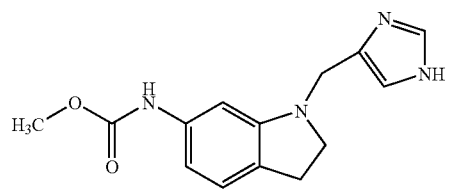
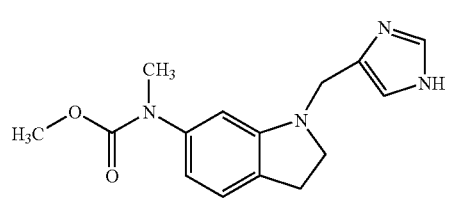
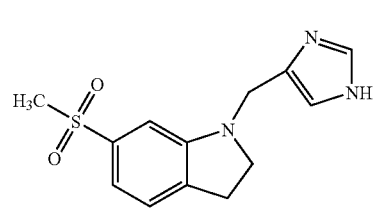
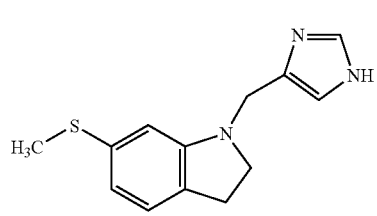
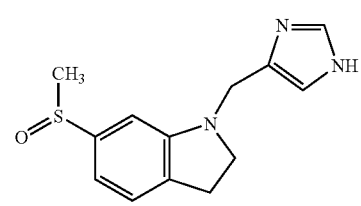
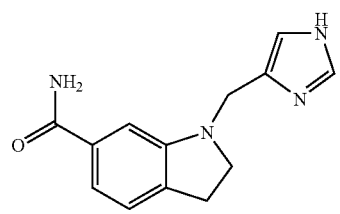
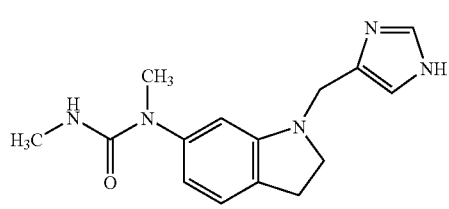
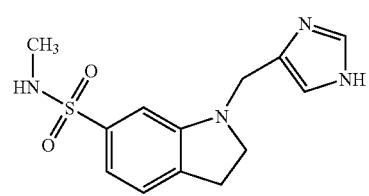
-continued
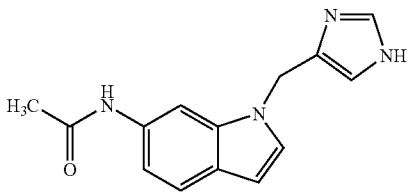
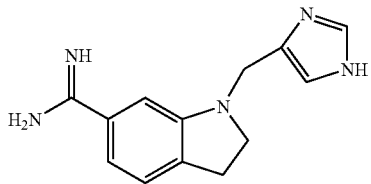
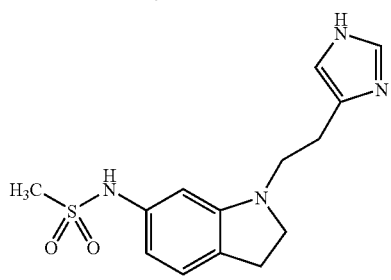
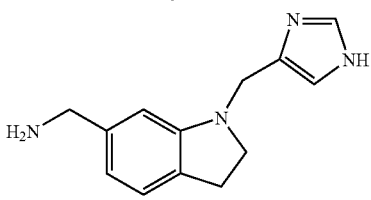
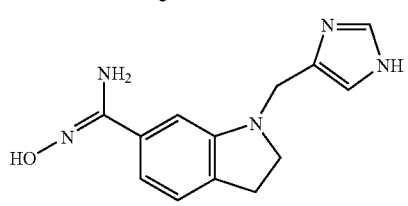
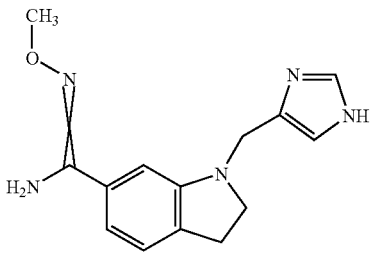
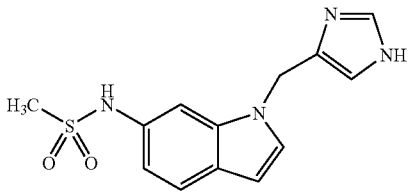
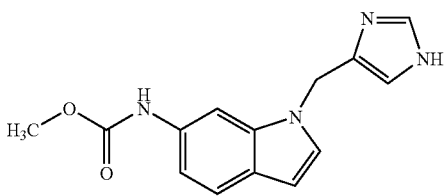

-continued
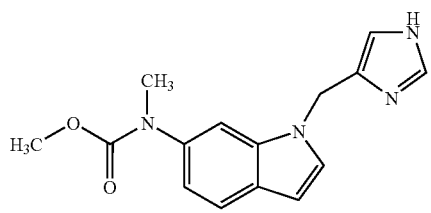
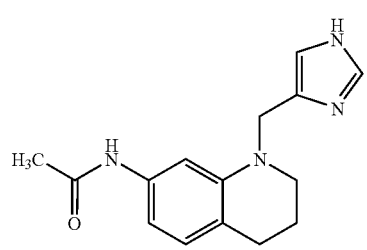
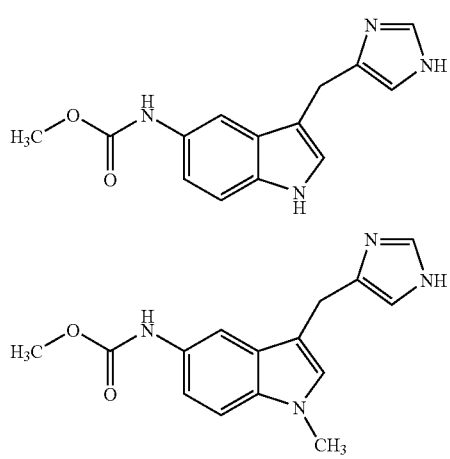
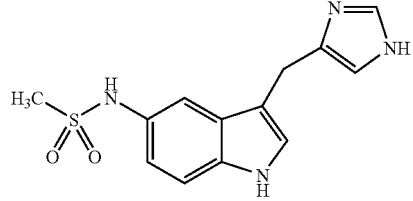
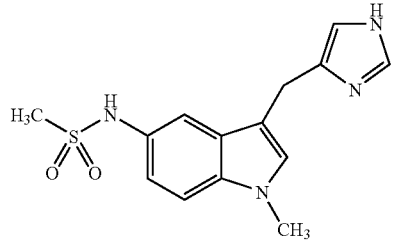
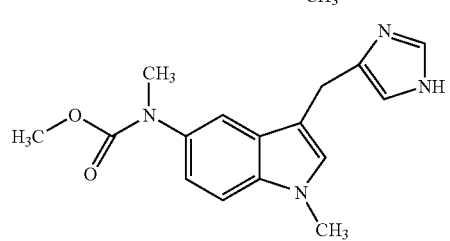
-continued
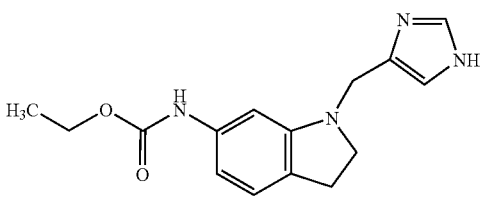
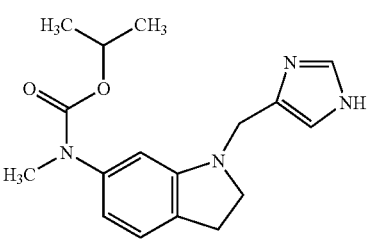
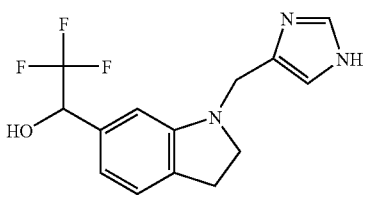
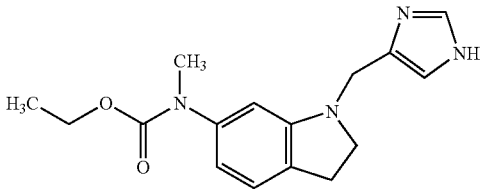
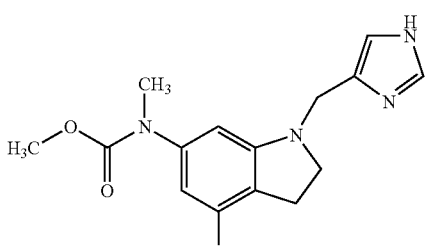
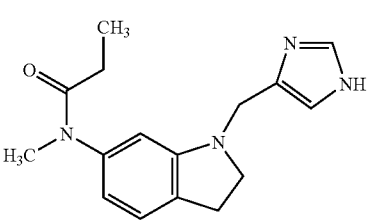
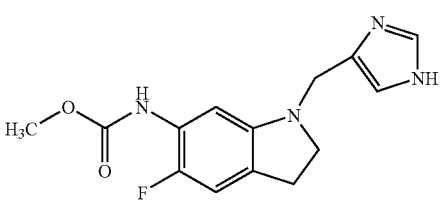

-continued
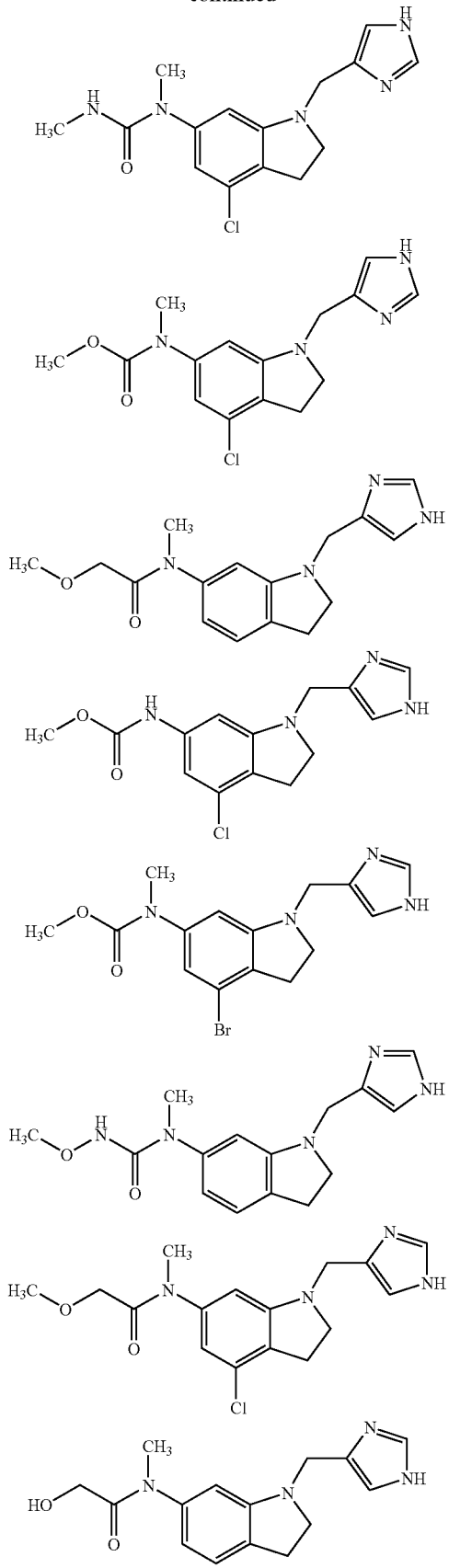
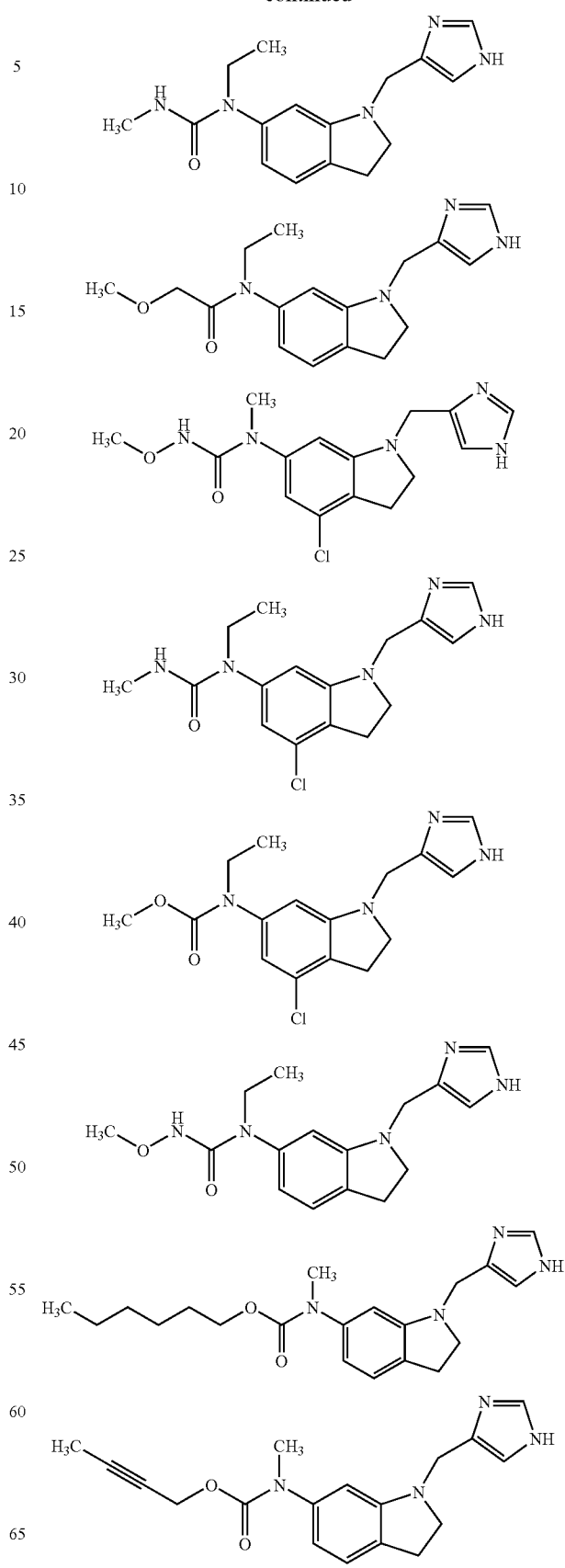

-continued

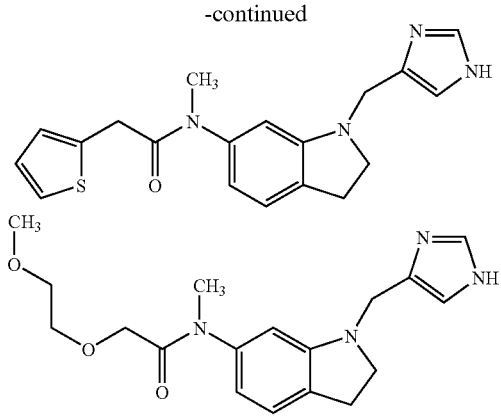

As used above, and throughout this disclosure, the following terms, unless otherwise indicated, shall be understood to have the following meanings:

"Patient" includes both human and animals.

"Mammal" means humans and other mammalian animals.

"Congestion" refers to all type of congestion including, but not limited to, congestion associated with perennial allergic rhinitis, seasonal allergic rhinitis, non-allergic rhinitis, vasomotor rhinitis, rhinitis medicamentosa, sinusitis, acute rhinosinusitis, or chronic rhinosinusitis or when the congestion is caused by polyps or is associated with the common cold.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The term "substituted alkyl" means that the alkyl group may be substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. The term "substituted alkynyl" means that the alkynyl group may be substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" and "Halo" mean fluorine, chlorine, bromine, or iodine. Preferred are fluorine, chlorine or bromine, and more preferred are fluorine and chlorine.

"Ring system substituent" means a substituent attached to an aromatic or non-aromatic ring system which, for example, replaces an available hydrogen on the ring system. Ring system substituents may be the same or different, each being independently selected from the group consisting of aryl, heteroaryl, aralkyl, alkylaryl, heteroaralkyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, $Y_1Y_2N$—, $Y_1Y_2N$-alkyl-, $Y_1Y_2NC(O)$— and $Y_1Y_2NSO_2$—, wherein $Y_1$ and $Y_2$ may be the same or different and are independently selected from the group consisting of hydrogen, alkyl, aryl, and aralkyl.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protected moieties are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, and the like.

It should be noted that in heterocyclyl containing systems of this invention, there are no hydroxyl groups on carbon atoms adjacent to a N, O or S, as well as there are no N or S groups on carbon adjacent to another heteroatom. Thus, for example, in the ring:

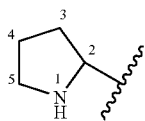

there is no —OH attached directly to carbons marked 2 and 5.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Heterocyclylalkyl" means a heterocyclyl-alkyl group in which the heterocyclyl and the alkyl are as previously described. Preferred heterocyclylalkyls contain a lower alkyl group. Non-limiting examples of suitable heterocyclylalkyl groups include piperidylmethyl, piperidylethyl, pyrrolidylmethyl, morpholinylpropyl, piperazinylethyl, azindylmethyl, azetidylethyl, oxiranylpropyl and the like. The bond to the parent moiety is through the alkyl group.

"Heterocyclenyl" (or "heterocycloalkeneyl") means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root-name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable monocyclic azaheterocyclenyl groups include 1,2,3,4-tetrahydropyridyl, 1,2-dihydropyridyl, 1,4-dihydropyridyl, 1,2,3,6-tetrahydropyridyl, 1,4,5,6-tetrahydropyrimidyl, 2-pyrrolinyl, 3-pyrrolinyl, 2-imidazolinyl, 2-pyrazolinyl, and the like. Non-limiting examples of suitable oxaheterocyclenyl groups include 3,4-dihydro-2H-pyran, dihydrofuranyl, fluorodihydrofuranyl, and the like. Non-limiting example of a suitable multicyclic oxaheterocyclenyl group is 7-oxabicyclo[2.2.1]heptenyl. Non-limiting examples of suitable monocyclic thiaheterocyclenyl rings include dihydrothiophenyl, dihydrothiopyranyl, and the like.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an organic acid group in which the —OH of the carboxyl group is replaced by some other substituent. Suitable non-limiting examples include H—C(O)—, alkyl-C(O)—, cycloalkyl-C(O)—, heterocyclyl-C(O)—, and heteroaryl-C(O)— groups in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound' or "stable structure" is meant a compound that is sufficiently robust to survive isolation to a useful degree of purity from a reaction mixture, and formulation into an efficacious therapeutic agent.

It is noted that carbons of formula I can be replaced with 1-3 silicon atoms, provided all valency requirements are satisfied.

The term "optionally substituted" means optional substitution with the specified groups, radicals or moieties.

It should also be noted that any heteroatom with unsatisfied valences in the text, schemes, examples and Tables herein is assumed to have the hydrogen atom to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, R$^2$, etc.) occurs more than one time in any constituent or formula, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, (C$_1$-C$_8$)alkyl, (C$_2$-C$_{12}$)alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C$_1$-C$_2$)alkylamino(C$_2$-C$_3$)alkyl (such as β-dimethylaminoethyl), carbamoyl-(C$_1$-C$_2$)alkyl, N,N-di(C$_1$-C$_2$)alkylcarbamoyl-(C1-C2)alkyl and piperidino-, pyrrolidino- or morpholino(C$_2$-C$_3$) alkyl, and the like.

Similarly, if a compound of Formula I contains an alcohol functional group, a prodrug can be formed by the replacement of the hydrogen atom of the alcohol group with a group such as, for example, (C$_1$-C$_6$)alkanoyloxymethyl, 1-((C$_1$-C$_6$)alkanoyloxy)ethyl, 1-methyl-1-((C$_1$-C$_6$)alkanoyloxy)ethyl, (C$_1$-C$_6$)alkoxycarbonyloxymethyl, N—(C$_1$-C$_6$)alkoxycarbonylaminomethyl, succinoyl, (C$_1$-C$_6$)alkanoyl, α-amino (C$_1$-C$_4$)alkanyl, arylacyl and α-aminoacyl, or α-aminoacyl-α-aminoacyl, where each α-aminoacyl group is independently selected from the naturally occurring L-amino acids, —P(O)(OH)$_2$, —P(O)(O(C$_1$-C$_6$)alkyl)$_2$ or glycosyl (the radical resulting from the removal of a hydroxyl group of the hemiacetal form of a carbohydrate), and the like.

If a compound of Formula I incorporates —NH— functional group, such as in a primary or secondary amine or in a nitrogen-containing heterocycle, such as imidazole or piperazine ring, a prodrug can be formed by the replacement of a hydrogen atom in the amine group with a group such as, for example, R-carbonyl, RO-carbonyl, NRR'-carbonyl where R and R' are each independently (C$_1$-C$_{10}$)alkyl, (C$_3$-C$_7$) cycloalkyl, benzyl, or R-carbonyl is a natural α-aminoacyl or natural α-aminoacyl, —C(OH)C(O)OY$^1$ wherein Y$^1$ is H, (C$_1$-C$_6$)alkyl or benzyl, —C(OY$^2$)Y$^3$ wherein Y$^2$ is (C$_1$-C$_4$) alkyl and Y$^3$ is (C$_1$-C$_6$)alkyl, carboxy(C$_1$-C$_6$)alkyl, amino (C$_1$-C$_4$)alkyl or mono-N— or di-N,N—(C$_1$-C$_6$)alkylaminoalkyl, —C(Y$^4$)Y$^5$ wherein Y$^4$ is H or methyl and Y$^5$ is mono-N— or di-N,N—(C$_1$-C$_6$)alkylamino morpholino, piperidin-1-yl or pyrrolidin-1-yl, and the like.

"Effective amount" or "therapeutically effective amount" is meant to describe an amount of compound or a composition of the present invention effective in producing the desired therapeutic, ameliorative, inhibitory or preventative effect.

"Capsule" is meant to describe a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

"Tablet" is meant to describe a compressed or molded solid dosage form containing the active ingredients with suitable diluents. The tablet can be prepared by compression of mixtures or granulations obtained by wet granulation, dry granulation or by compaction.

"Oral gels" is meant to describe to the active ingredients dispersed or solubilized in a hydrophillic semi-solid matrix.

"Powders for constitution" refers to powder blends containing the active ingredients and suitable diluents which can be suspended in water or juices.

"Diluent" refers to substances that usually make up the major portion of the composition or dosage form. Suitable diluents include sugars such as lactose, sucrose, mannitol and sorbitol; starches derived from wheat, corn, rice and potato;

and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

"Disintegrants" refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

"Binders" refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

"Lubricant" is meant to describe a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d'l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

"Glidents" means materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

"Coloring agents" refers to excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

"Bioavailability" refers to the rate and extent to which the active drug ingredient or therapeutic moiety is absorbed into the systemic circulation from an administered dosage form as compared to a standard or control. Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula III contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of Formula I, and salts, solvates and prodrugs thereof, may exist in their tautomeric form (for example, as an amide or imino ether). All such tautomeric forms are contemplated herein as part of the present invention. For example,

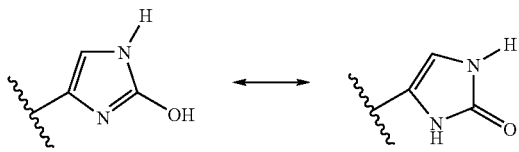

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons or sulfurs on various substituents, including enantiomeric forms (which may exist even in the absence of asymmetric carbons), rotameric forms, atropisomers, and diastereomeric forms, are contemplated within the scope of this invention. For example, if a compound of Formula (I) incorporates a double bond or a fused ring, both the cis- and trans-forms, as well as mixtures, are embraced within the scope of the invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

Diasteromeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diasteromeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

Polymorphic forms of the compounds of formula I, and of the salts, solvates and prodrugs of the compounds of formula I, are intended to be included in the present invention The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

The compounds according to the invention have pharmacological properties; in particular, the compounds of Formula I can be useful as α2C adrenoreceptor agonists.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

The compounds of this invention may also be useful in combination (administered together or sequentially) with one or more therapeutic agents such as, for example, steroids, PDE-4 inhibitors, anti-muscarinic agents, cromolyn sodium, $H_1$ receptor antagonists, 5-$HT_1$ agonists, NSAIDs, angiotensin-converting enzyme inhibitors, angiotensin II receptor agonists, β-blockers, β-agonists (including both long and short acting), leukotriene antagonists, diuretics, aldosterone antagonists, ionotropic agents, natriuretic peptides, pain management/analgesic agents, anti-anxiety agents, anti-migraine agents, and therapeutic agents suitable for treating heart conditions, psychotic disorders, and glaucoma.

Suitable steroids include prednisolone, fluticasone (including all ester such as the propionate or furoate esters), triamcinolone, beclomethasone, mometasone (including any ester form such as mometasone furoate), budasamine, ciclesonide betamethasone, dexamethasone, prednisone, flunisolide, and cortisone.

Suitable PDE-4 inhibitors include roflumilast, theophylline, rolipram, piclamilast, cilomilast and CDP-840.

Suitable antiimuscarinic agents include ipratropium bromide and tiatropium bromide.

Suitable $H_1$ antagonists include astemizole, azatadine, azelastine, acrivastine, brompheniramine, cetirizine, chlorpheniramine, clemastine, cyclizine, carebastine, cyproheptadine, carbinoxamine, descarboethoxyloratidine, diphenhydramine, doxylamine, dimethindene, ebastine, epinastine, efletirizeine, fexofenadine, hydroxyzine, ketotifen, loratidine, levocabastine, meclizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

Suitable anti-inflammatory agents include aspirin, diclofenac, diflunisal, etodolac, flurbiprofen, ibuprofen, indomethacin, ketoprofen, ketorolac, nabumetone, naproxen, oxaprozin, piroxicam, sulindac, and tolmetin.

Suitable aldosterone antagonists include spironolactone.

Suitable ionotropic agents include digitalis.

Suitable angiotensin II receptor agonists include irbesartan and losartan.

Suitable diuretics include spironolactone, methyclothiazide, bumetanide, torsemide, hydroflumethiazide, trichlormethiazide, hydroclorothiazide, triamterene, ethacrynic acid, methyclothiazide, hydrochlorothiazide, benzthiazide, hydrochlorothiazide, quinethazone, hydrochlorothiazide, chlorthalidone, furosemide, indapamide, hydroclorothiazide, triamterene, trichlormethiazide, hydrochlorothiazide, amiloride HCl, amiloride HCl, metolazone, trichlormethiazide, bendroflumethiazide, hydrochlorothiazide, polythiazide, hydroflumethiazide, chlorthalidone, and metolazone.

Suitable pain management/analgesic agents include Celecoxib, amitriptyline, ibuprofen, naproxen, gabapentin, tramadol, rofecoxib, oxycodone HCl, acetaminophenoxycodone HCl, carbamazepine, diclofenac, diclofenac, etodolac, fenoprofen calcium, flurbiprofen, ibuprofen, indomethacin, ketoprofen, ketorolac tromethamine, mefenamic acid, meloxicam, nabumetone, naproxen, oxaprozin, piroxicam, sulindac, tolmetin sodium, valdecoxib, diclofenac/misoprostol, oxycontin, vicodin, darvocet, morphine sulfate, dilaudid, stadol, stadol NS, acetaminophen with codeine, acetaminophen with codeine #4, Lidoderm® patches, and percocet.

Suitable β-blockers include acebutolol, atenolol, atenolol/chlorthalidone, betaxolol, bisoprolol fumarate, bisoprolol/HCTZ, labetolol, metoprolol tartrate, nadolol, pindolol, propranolol, propranolol/HCTZ, sotalol, and timolol.

Suitable β-agonists include dobutamine, ritodrine, salbutamol, levalbuterol, metaproternol, formoterol, fenoterol, bambuterol, brocaterol, clenbuterol, terbutaline, tulobuterol, epinephrine, isoprenalin, and hexoprenalin.

Suitable leucotriene antagonists include levamisole.

Suitable anti-migraine agents include rovatriptan succinate, naratriptan HCl, rizatriptan benzoate, sumatriptan succinate, zolmitriptan, almotriptan malate, methysergide maleate, dihydroergotamine mesylate, ergotamine tartrate, ergotamine tartrate/caffeine, Fioricet®, Fiorninal®, Depakene®, and Depakote®.

Suitable anti-anxiety and anti-depressant agents include amitriptyline HCl, bupropion HCl, citalopram hydrobromide, clomipramine HCl, desipramine, fluoxetine, fluvoxamine maleate, maprotiline HCl, mirtazapine, nefazodone HCl, nortriptyline, paroxetine HCl, protriptyline HCl, sertraline HCl, doxepin, and trimipramine maleate.

Suitable angiotensin converting enzyme inhibitors include Captopril, enalapril, enalapril/HCTZ, lisinopril, lisinopril/HCTZ, and Aceon®.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions or suspensions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Another aspect of this invention is a kit comprising a therapeutically effective amount of at least one compound of Formula I, or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one therapeutic agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz), Varian Mercury VX-400 (400 MHz), or Bruker-Biospin AV-500 (500 MHz), and are reported as ppm with number of protons and multiplicities indicated parenthetically. Where LC/MS data are presented, analyses was performed using an Applied Biosystems API-100 mass spectrometer and C18 column, 10-95% $CH_3CN$—$H_2O$ (with 0.05% TFA) gradient. The observed parent ion is given.

The following solvents and reagents may be referred to by their abbreviations in parenthesis:

Me=methyl; Et=ethyl; Pr=propyl; Bu=butyl; Ph=phenyl, and Ac=acetyl
μl=microliters
AcOEt or EtOAc=ethyl acetate
AcOH or HOAc=acetic acid
ACN=acetonitrile
atm=atmosphere
Boc or BOC=tert-butoxycarbonyl
DCM or $CH_2Cl_2$: dichloromethane:
DIPEA=diisopropylethylamine
DMAP=4-dimethylaminopyridine
DMF=dimethylformamide
DMS=dimethylsulfide
DMSO=dimethyl sulfoxide
EDCI=1-(3-dimethylaminopropyl)-3-ethylcarbodiimide
Fmoc=9-fluorenylmethoxycarbonyl
g=grams
h=hour
HATU=O-(7-azabenzotriazol-1-yl)-N,N,N',N'-tetramethyluronium hexafluorophosphate
HOBt=1-hydroxybenzotriazole
LAH=lithium aluminum hydride
LCMS=liquid chromatography mass spectrometry
min=minute
mg=milligrams
mL=milliliters
mmol=millimoles
MCPBA=3-chloroperoxybenzoic acid
MeOH: methanol
MS=mass spectrometry
NMR=nuclear magnetic resonance spectroscopy
RT or rt=room temperature (ambient, about 25° C.).
TEA or $Et_3N$=triethylamine
TFA=trifluoroacetic acid
THF=tetrahydrofuran
TLC=thin layer chromatography
TMS=trimethylsilyl
Tos or tosyl=p-toluenesulfonyl
Tr=triphenylmethyl

EXAMPLES

The compounds of this invention can be prepared through the general approach outlined in Schemes 1 and 2. Scheme 1 shows an approach in which S1 and S2 are joined together. Examples of these approaches include reaction of S1 with an electrophilic S2 compound. In various embodiments, R' is an carboxaldehyde (leading to coupling by reductive amination), a carboxylic acid (leading to amide coupling) or methylene chloride (leading to coupling by alkylation).

SCHEME 1:

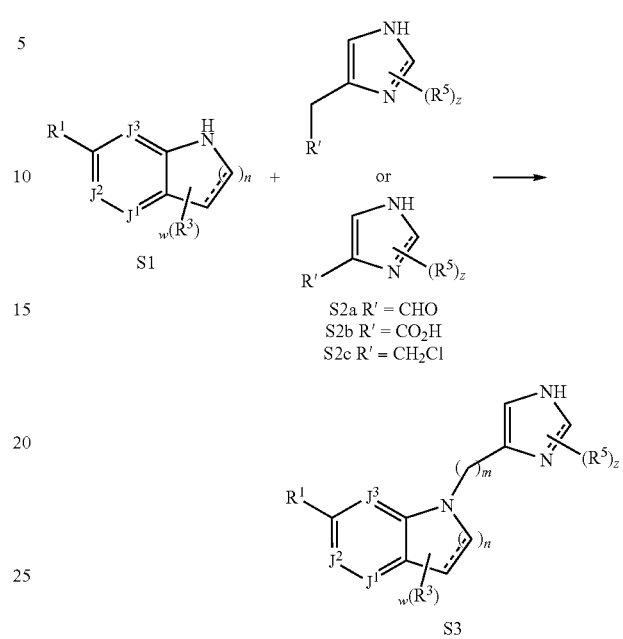

S2a R' = CHO
S2b R' = $CO_2H$
S2c R' = $CH_2Cl$

According to another embodiment, compound S6 is prepared by alkylation of S4 with S5. Exemplary procedures employed in the synthesis of various S1 and S4 fragments are described in the examples below.

SCHEME 2:

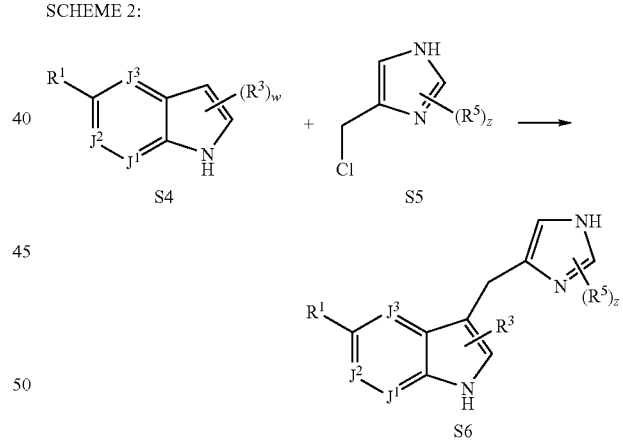

The starting materials and reagents used in preparing compounds described are either available from commercial suppliers such as Aldrich Chemical Co. (Wisconsin, USA) and Acros Organics Co. (New Jersey, USA) or were prepared by literature methods known to those skilled in the art.

Compounds of formulae S3 and S6 can be prepared by the general methods outlined above. Exemplary compounds were prepared as described in the examples below or from starting materials known in the art. These examples are being provided to further illustrate the present invention. They are for illustrative purposes only; the scope of the invention is not to be considered limited in any way thereby.

Preparative Example 1

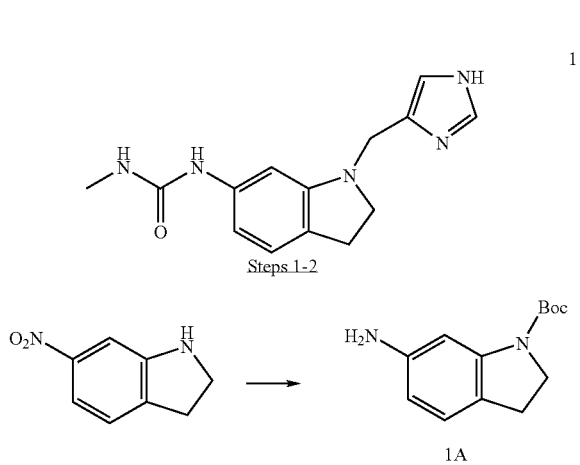

Steps 1-2

To a stirred solution of 6-nitroindoline (8.0 g, 48.8 mmol) in DCM (50 mL) was added pyridine (9.9 mL, 122 mmol), (Boc)$_2$O (10.6 g, 48.6 mmol) and catalytic DMAP. The mixture was stirred overnight. Reaction was washed with brine, and the organic layer was dried (Na$_2$SO$_4$), filtered and concentrated. Chromatography (20% EtOAc/hexanes) provided 1-Boc-6-nitroindoline (10 g, 78%).

To a stirred solution of 1-Boc-6-nitroindoline (3.5 g, 13.2 mmol) in MeOH/EtOAc (80 mL/40 mL) was added 10% Pd/C (700 mg). The reaction was stirred under H$_2$ (1 atm) overnight. The mixture was filtered through celite and concentrated to give 1A (3.1 g, 100%).

Steps 3-4

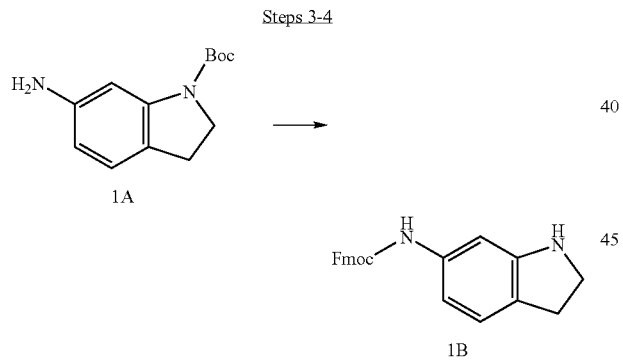

To a stirred solution of compound 1A (1.33 g, 5.68 mmol) in dioxane (36 mL) and H$_2$O (10 mL) at 0° C. was added Na$_2$CO$_3$ (66 g, 6.25 mmol) and Fmoc-Cl (1.61 g, 6.25 mmol). The reaction was stirred at 0° C. for 1.5 h and then at RT for 1 h. Solvent was removed under reduced pressure and the residue was partitioned between H$_2$O (50 mL) and DCM (50 mL). The aqueous phase was extracted with DCM (50 mL). The combined organic layer was dried (Na$_2$SO$_4$), filtered and concentrated under reduced pressure. The residue was purified by chromatography (10-30% EtOAc/hexanes) to give 2.31 g (90%). This compound was stirred in 30% TFA/DCM (50 mL) for 0.5 h. Solvent was removed under reduced pressure and sat. NaHCO$_3$ solution was added (50 mL). The mixture was extracted with DCM (3×50 mL). The combined organic layer was dried (Na$_2$SO$_4$), filtered and concentrated to give 1B (1.6 g, 80%).

Step 5

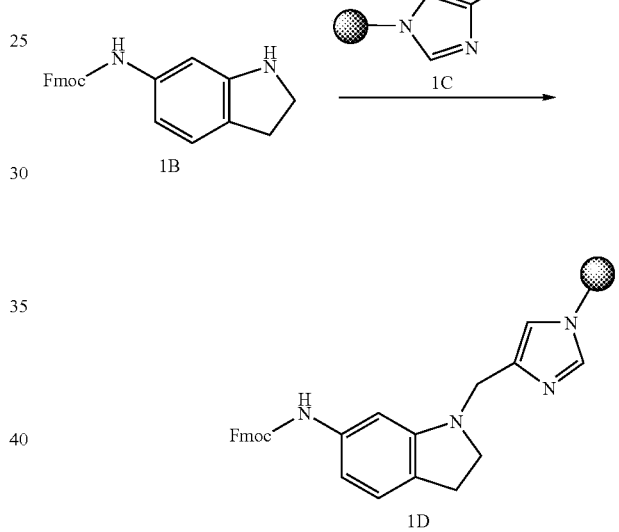

The resin bound imidazole-4-carboxyaldehyde (1C) was prepared as follows: 2-Chlorotrityl chloride resin (1 g, 1.1 to 1.6 mmole/g, Novabiochem, 100-200 mesh, 1% DVB) was suspended in dry DMF (5 mL) and 1,2-dichloroethane (5 mL), followed by addition of 4-imidazolecarboxaldehyde (0.28 g, 3.3 mmol) and TEA (0.46 mL, 3.3 mmole). The mixture was shaken overnight. The resin was filtered and washed with DMF (3×10 mL), MeOH (3×10 mL), and DCM (4×10 mL) and dried under high vacuum overnight.

To a suspension of resin 1C (0.3 g, 0.42 mmol) and 1B (0.6 g, 1.68 mmol) in 1,2-dichloroethane (8 mL) and N,N-dimethylacetamide (2 mL) was added NaBH(OAc)$_3$ (0.71 g, 3.36 mmol). The mixture was shaken overnight. The resin was filtered and washed with DMF (3×10 mL), MeOH (3×10 mL), and DCM (4×10 mL) to give resin 1D.

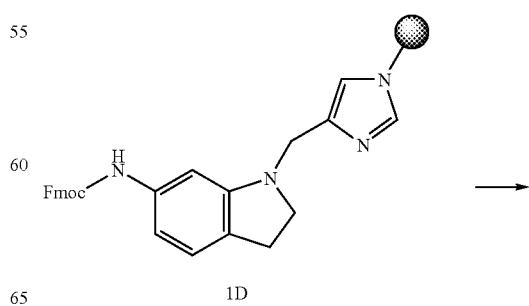

-continued

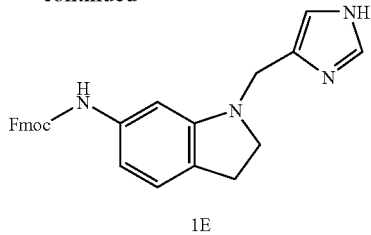

1E

A small amount of resin 1D (10 mg) was cleaved in 50% TFA/DCM for 1 h. The resin was filtered and the filtrate was concentrated under reduced pressure and the residue was identified in LC-MS as a single peak as the desired cleavage product 1E. MS m/z 437 (MH+).

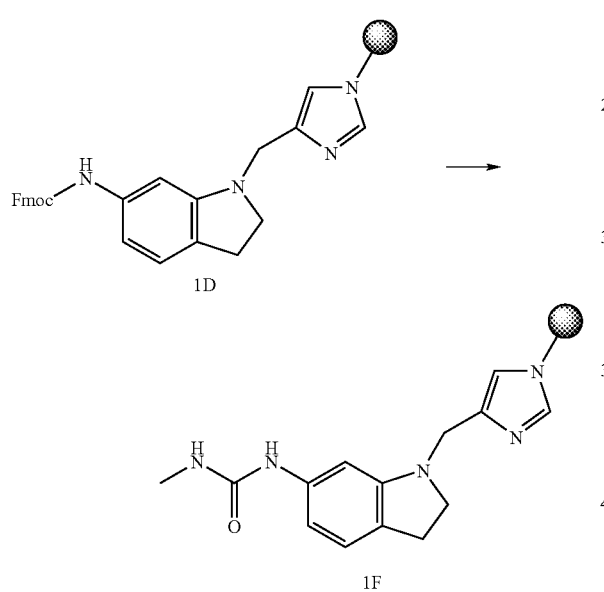

Resin 1D (25 mg) was shaken in 30% piperidine/DMF (5 mL) for 2 h. The resin was filtered and washed with DMF (3×10 mL), MeOH (3×10 mL), and DCM (4×10 mL). The resin was then suspended in DCM (4 mL) and MeNCO (0.1 g) was added. The mixture was shaken overnight. The resin was washed with DCM (3×10 mL), MeOH (3×10 mL), and DCM (4×10 mL) to give resin 1F.

Resin 1F was cleaved in 50% TFA/DCM (10 mL) for 3 h and filtered. The filtrate was concentrated under reduced pressure to give the title compound 1 as a TFA salt. MS m/z 272 (MH+).

Compounds in Table 1 were prepared similarly as described above, by deprotecting resin 1D and then capping with different reagents as shown in the table. After cleavage from the resin, the final compound can be purified further by Gilson HPLC (YMC COMBI PREP ODS-AQ 50×20 mm I.D. with 5 micron particle size, 20 mL/min, 10 min gradient: 10-90% ACN: $H_2O$ with 0.1% TFA). Alternatively, compound 1G and 1H can be prepared by following procedure as described in Example 4. Compound 1, 1I and 1J can also be prepared by following procedure as described in Example 5.

TABLE 1

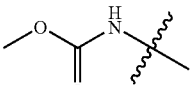

| Cpd | Reagent | R | MS (MH+) |
|---|---|---|---|
| 1G | ClCO₂Me Pyridine | 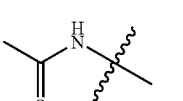 | 273 |
| 1H | Ac₂O Pyridine | 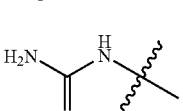 | 257 |
| 1I | Me₃SiNCO | 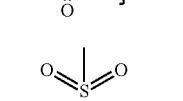 | 258 |
| 1J | CH₃SO₂Cl DIPEA | 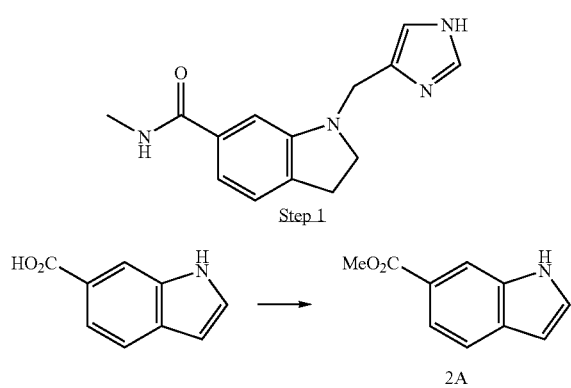 | 371 |

Preparative Example 2

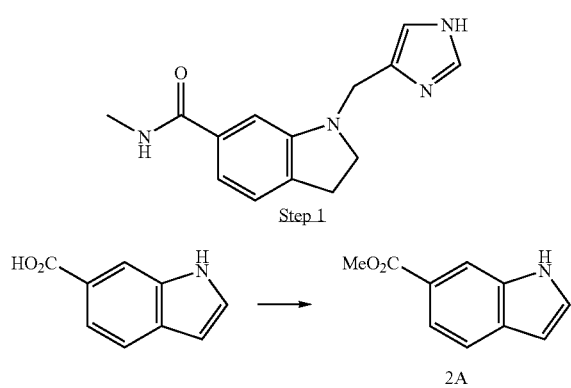

To a stirred solution of 1H-indole-6-carboxylic acid (1.5 g, 9.31 mmol) in MeOH (200 mL) was added conc. $H_2SO_4$ (3 mL). The reaction was refluxed for 15 h and cooled to RT. The mixture was neutralized with sat. NaHCO₃ and MeOH was removed under reduced pressure. The remaining mixture was extracted with EtOAc (50 mL×3). The combined organic layer was dried ($Na_2SO_4$), filtered and concentrated under reduced pressure. Chromatography (20% EtOAc/hexanes) provided 2A (1.4 g, 88%) as a white solid.

Step 2

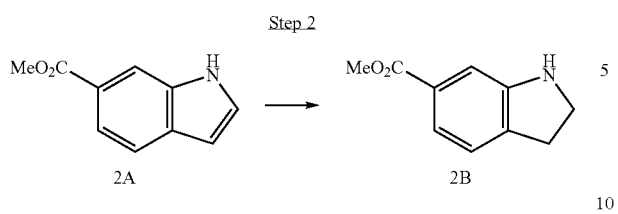

A stirred solution of 2A (1 g, 5.7 mmol) in DCM (20 mL) and TFA (10 mL) at −20° C. was treated with Et₃SiH (10 mL). The reaction was warmed to RT slowly and stirred thereafter for 17 h. The reaction was quenched with 2 N NaOH until pH 8. The mixture was extracted with DCM (100 mL×3). The combined organic layer was dried (Na₂SO₄), filtered and concentrated under reduced pressure. Chromatography (20% EtOAc/hexanes) provided 2B (0.5 g, 49%).

Step 3

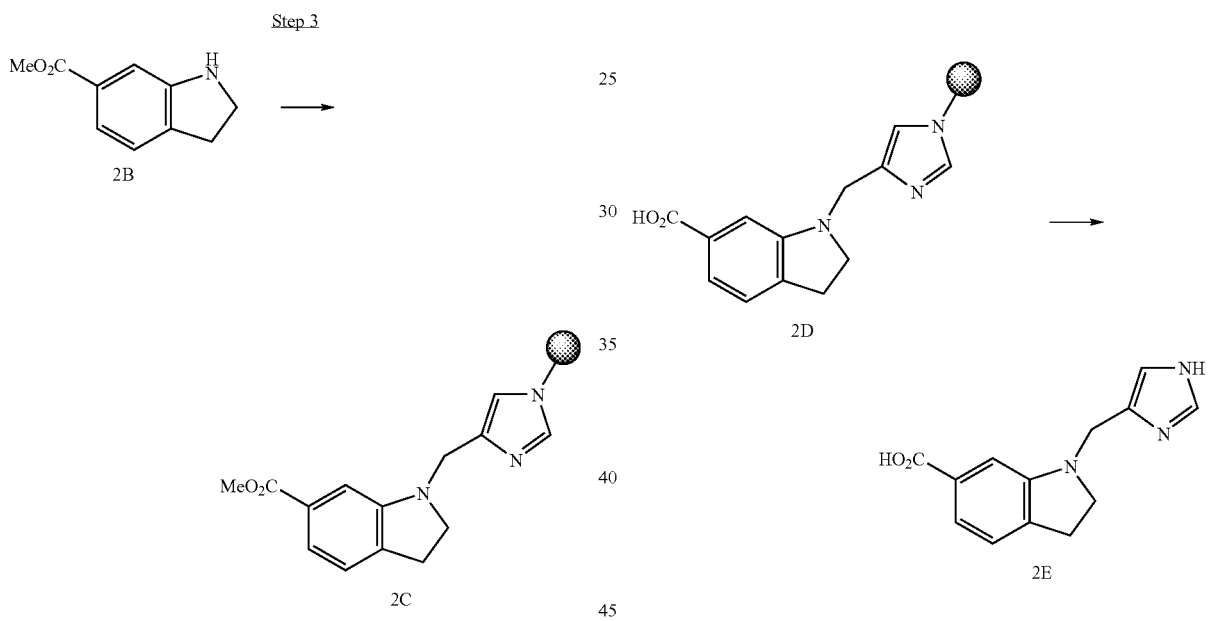

In a manner similar to that found in Example 1, Step 5, 2B and resin 1C were converted to resin 2C.

Step 4

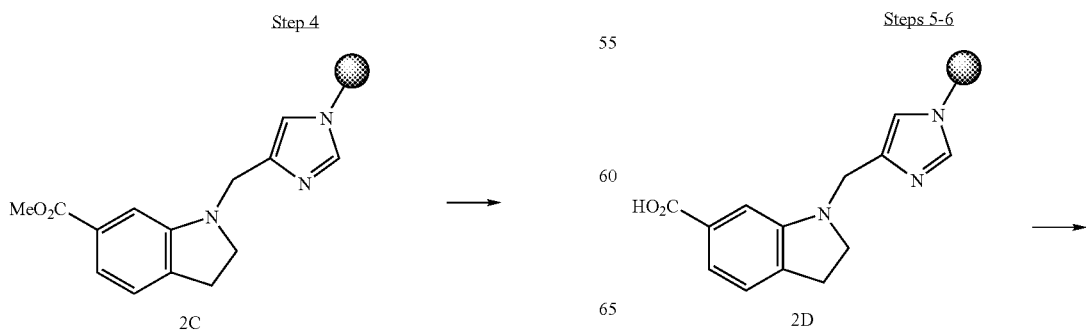

-continued

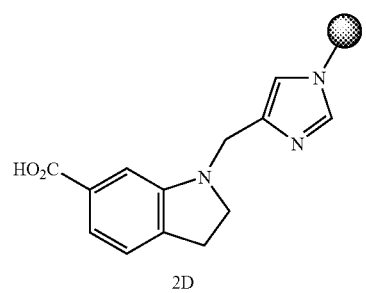

Resin 2C (0.16 g) was treated with 8 mL of a solution prepared by dissolving KOH (7.2 g) in H₂O (2 mL)/MeOH (60 mL)/dioxane (60 mL). The mixture was shaken overnight. The resin was filtered and washed with dioxane (3×10 mL), MeOH (3×10 mL), DCM (4×10 mL) and pumped on high vacuum to give resin 2D.

A small amount of resin 2D (10 mg) was cleaved in 50% TFA/DCM for 1 h. The resin was filtered and the filtrate was concentrated under reduced pressure and the residue was identified in LC-MS as the desired cleavage product 2E: MS m/z 271 (MH+).

Steps 5-6

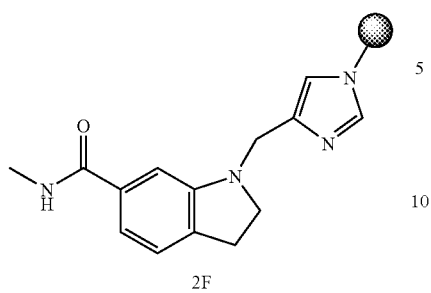

2F

Resin 2D (0.1 g, 0.16 mmol) was suspended in 1:1 DCM:DMF (3 mL) and treated with MeNH$_2$ (2 M/THF, 0.5 mL), EDCI (0.16 mL, 1 mmol) and HOBt (0.074 g, 0.48 mmol). The mixture was shaken overnight. The resin was filtered and washed with DMF (3×10 mL), MeOH (3×10 mL), and DCM (4×10 mL) to give resin 2F.

In a manner similar to that found in Example 1, Step 8, 2F was converted to the title compound 2. MS m/z 257 (MH+).

Compounds in Table 2 can be prepared similarly as described above starting from resin 2D, by coupling with different reagents as shown in the table. If needed, the final compounds can be further purified as described in Example 1.

TABLE 2

| Cpd | reagent | R | MS (MH+) |
|---|---|---|---|
| 2G | NH$_4$Cl DIPEA | NH$_2$ | 243 |
| 2H | (structure) | (structure) | 314 |
| 2I | (structure) | (structure) | 301 |
| 2J | Me$_2$NH | (structure) | 271 |
| 2K | morpholine | (structure) | 313 |

Preparative Example 3

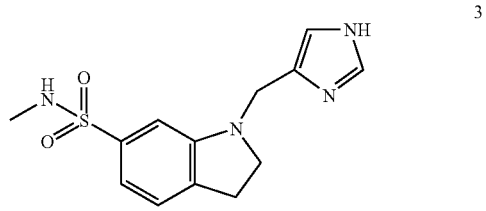

3

Step 1

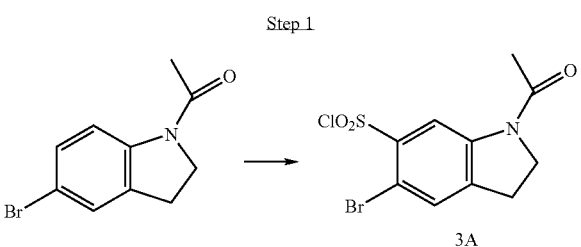

Chlorosulfonic acid (5 g, 42.9 mmol) was cooled in an ice bath and treated with 1-(5-bromoindolin-1-yl)ethanone (2.4 g, 10 mmol). The reaction was stirred at 0° C. for 20 min and then heated to 70° C. for 7 h. After cooling, the mixture was slowly poured onto ice. The precipitate was filtered, washed with H$_2$O and pumped on high vacuum overnight to give a crude mixture containing compound 3A and starting material in ratio of 2:3 as determined by $^1$H NMR.

Step 2

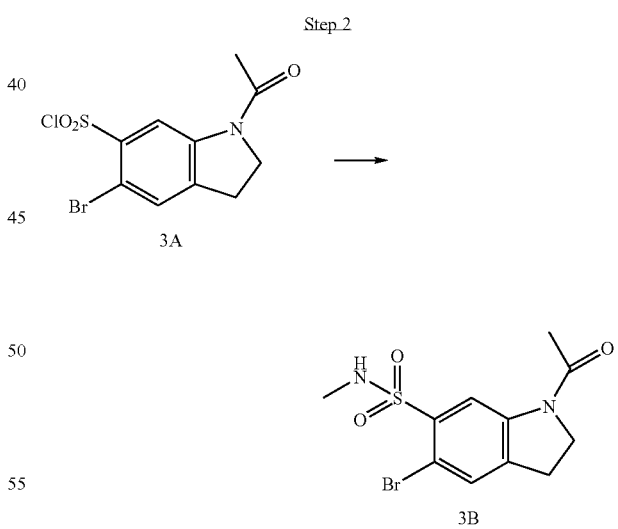

One third of the above mixture was dissolved in DCM (10 mL) and treated with MeNH$_2$ (2 M/THF, 5 mL). The reaction was stirred at RT overnight, concentrated, and partitioned between EtOAc and water. The aqueous layer was extracted with EtOAc (2×100 mL). The combined organic layers were dried (Na$_2$SO$_4$), filtered and concentrated. Chromatography (60-100% EtOAc/hexanes) provided 3B (0.39 g).

Step 3

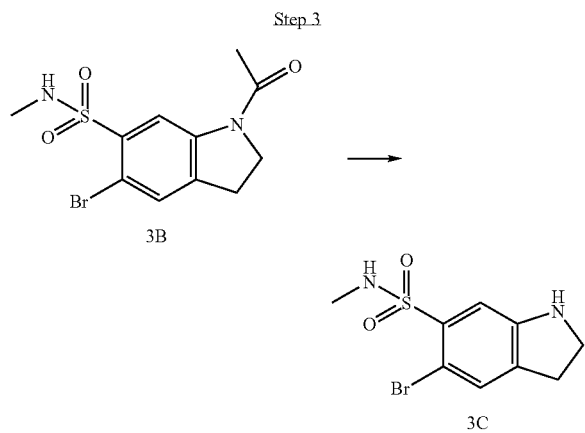

To Compound 3B (0.39 g, 1.17 mmol) was added 37% HCl (10 mL) and the mixture was refluxed for 1.5 h. The reaction was cooled and diluted with $H_2O$, then basified with 2 N NaOH. After extraction with EtOAc (2×50 mL), the organic layer was dried ($Na_2SO_4$), filtered and concentrated to give 3C (0.26 g, 76%).

Step 4-5

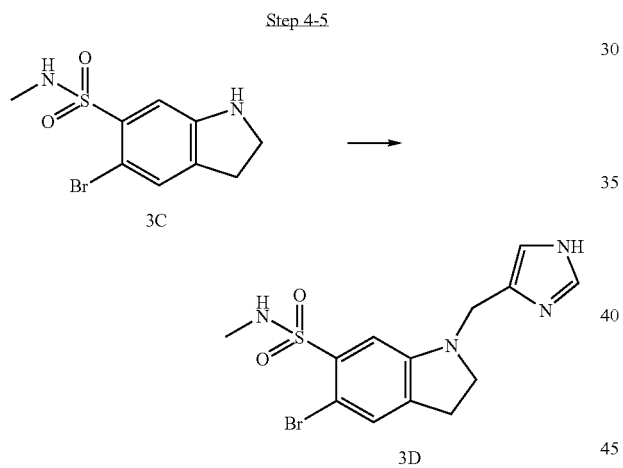

In a manner similar to that found in Example 1, Steps 5 and 8, 3C was converted to compound 3D. MS m/z 371 (MH+). Alternatively, 3C can be reacted with 4-imidazolecarboxaldehyde and converted to 3D as described in Example 4, Step 1.

Step 6

A mixture of 3D (0.14 g, 0.37 mmol) and 10% Pd/C (20 mg) in MeOH (10 mL) was hydrogenated at 50 psi $H_2$ overnight and filtered through celite. The filtrate was concentrated under reduced pressure. The residue was purified by Glison 215 HPLC (YMC COMBI PREP ODS-AQ 50×20 mm I.D. with 5 micron, 20 mL/min, 10 min gradient: 10-90 ACN/$H_2O$ with 0.1% TFA) to give the title compound 3. MS m/z 293 (MH+).

Compounds in Table 3 can be prepared similarly as described above starting from compound 3A, by coupling with different amines as shown in the table.

TABLE 3

| Cpd | reagent | $R_1$ | $R_2$ | MS (MH+) |
|---|---|---|---|---|
| 3E | $NH_3$/MeOH | $NH_2$ | H | 279 |
| 3F | $Me_2NH$/THF | $NMe_2$ | Br | 385 |
| 3G | $Me_2NH$/THF | $NMe_2$ | H | 307 |

Preparative Example 4

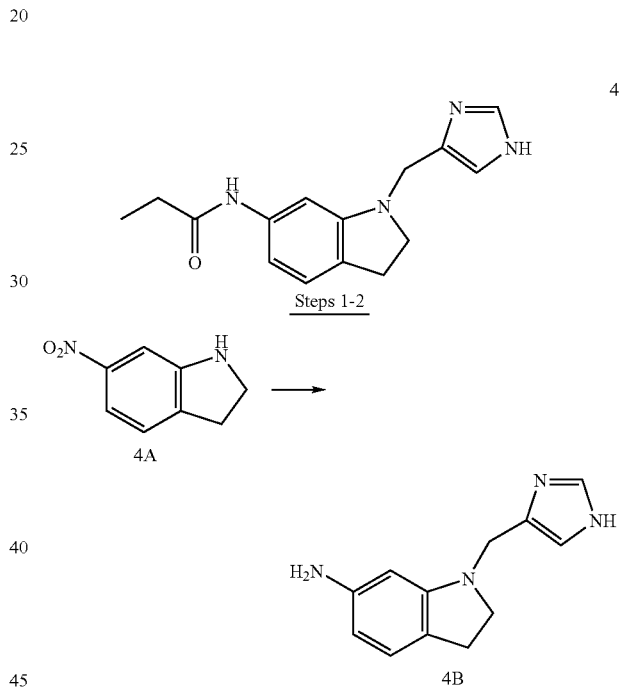

Steps 1-2

To a stirred solution of 4A (5 g, 30 mmol) in 1,2-dichloroethane (100 mL) was added 4-imidazolecarboxaldehyde (2.9 g, 30 mmol) and HOAc (3 mL). The mixture was stirred for 1 h, and NaBH(OAc)$_3$ (13 g, 61 mmol) was added. The reaction was stirred overnight at RT, and washed with NaHCO$_3$ and brine. The organic layer was dried (MgSO$_4$), filtered and concentrated (7 g, 94%).

The resulting product was hydrogenated in a manner similar to that found in Example 1, Step 2, to provide 4B.

Step 3

To compound 4B (0.43 g, 2 mmol) in DCM (10 mL) was added TEA (0.7 mL, 5 mmol) and EtCOCl (0.35 mL, 4 mmol). The mixture was stirred at RT for 1.5 h. After adding 2 N NaOH, the mixture was extracted with DCM (3×30 mL). The organic layer was dried (MgSO$_4$), filtered and concentrated. Chromatography (2-5% of 7N NH$_3$-MeOH/DCM) provided the title compound 4 (0.173 g). MS m/z 271 (MH+).

Compounds in Table 4 were prepared in a similar fashion starting from compound 4B:

TABLE 4

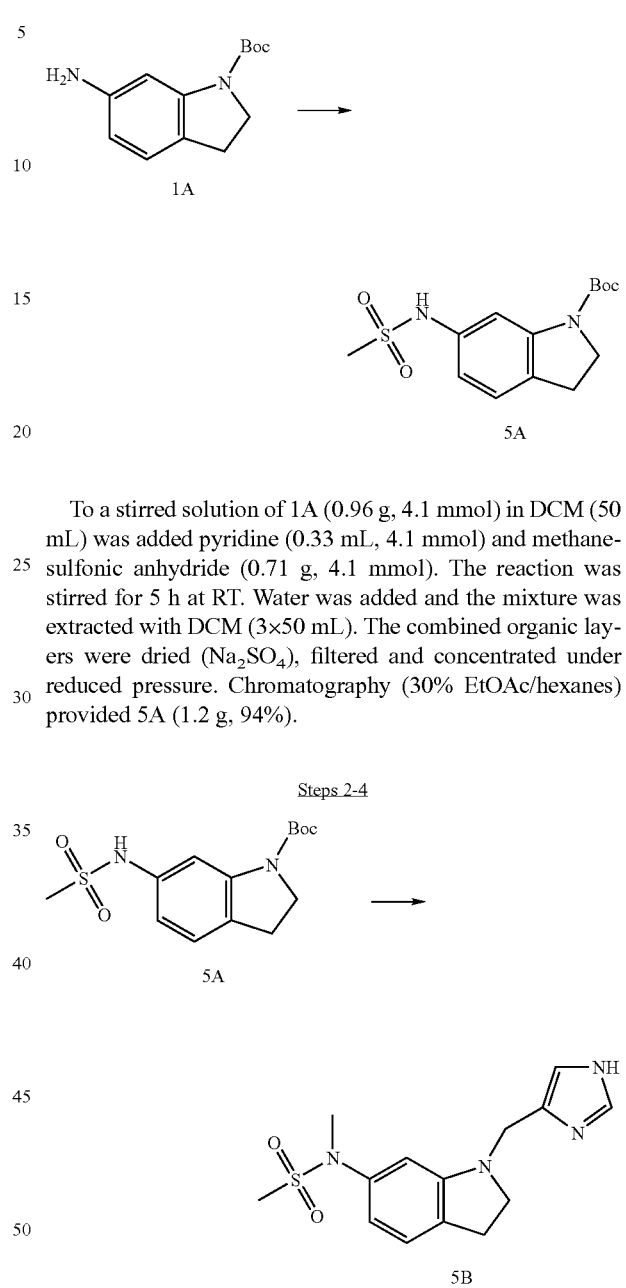

| Cpd | R | Spectral data |
|---|---|---|
| 4C | (1-oxobutyl, methyl-substituted) | MS 285 (MH+) |
| 4D | (isopropyl ketone, methyl-substituted) | MS 285 (MH+) |
| 4E | (2-furanyl ketone, methyl-substituted) | MS 309 (MH+) |
| 4F | (phenyl ketone, methyl-substituted) | MS 319 (MH+) |
| 4G | (dimethylamino-acetyl, methyl-substituted) | MS 300 (MH+) |
| 4H | (methoxy-acetyl, methyl-substituted) | $^1$H NMR(CD$_3$OD): 7.61 (s, 1H), 6.96 (d, 3H), 6.80 (d, 1H), 4.22 (s, 2H), 4.0 (s, 2H), 3.45 (s, 3H), 3.34 (t, 2H), 2.85 (t, 2H) |

Preparative Example 5

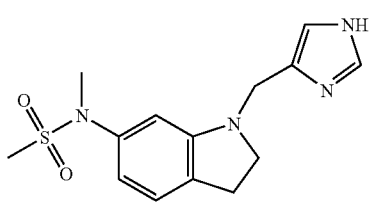

Step 1

To a stirred solution of 1A (0.96 g, 4.1 mmol) in DCM (50 mL) was added pyridine (0.33 mL, 4.1 mmol) and methanesulfonic anhydride (0.71 g, 4.1 mmol). The reaction was stirred for 5 h at RT. Water was added and the mixture was extracted with DCM (3×50 mL). The combined organic layers were dried (Na$_2$SO$_4$), filtered and concentrated under reduced pressure. Chromatography (30% EtOAc/hexanes) provided 5A (1.2 g, 94%).

Steps 2-4

To a stirred solution of 5A (0.73 g, 2.34 mmol) in 1 M NaOH (10 mL) was added MeI (0.44 mL). The mixture was stirred overnight, diluted with water (20 mL) and extracted with DCM (3×30 mL). The combined organic layer was dried (Na$_2$SO$_4$), filtered and concentrated under reduced pressure. The residue was then deprotected and converted to 5B in a manner similar to that found in Example 1, Step 4 and Example 4, Step 1. MS m/z 307 (MH+).

The following compounds can be prepared by reacting compound 1A with ethyl chloroformate, N,N-dimethylsulfamoyl chloride or methanesulfonic anhydride, respectively, followed by Boc-deprotection and reductive alkylation.

TABLE 5

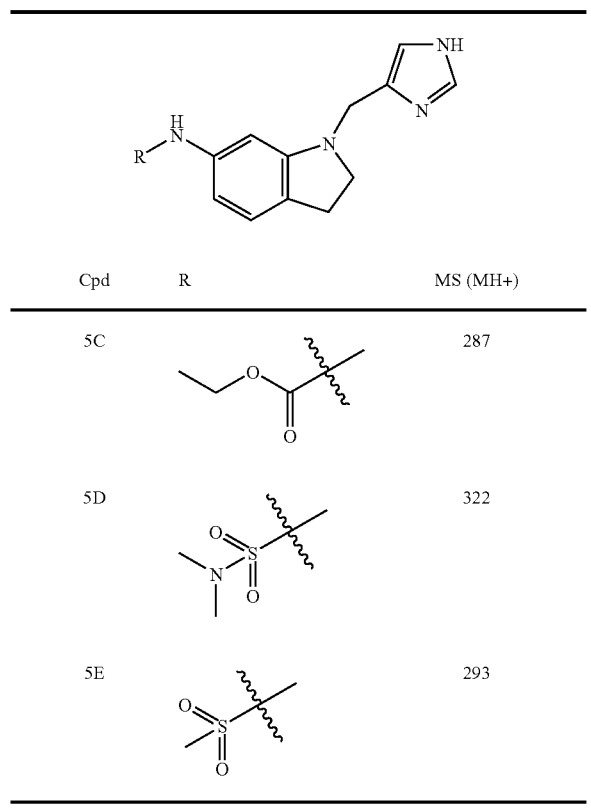

| Cpd | R | MS (MH+) |
|---|---|---|
| 5C | ethyl 2-methylpropanoate group | 287 |
| 5D | N,N-dimethylsulfamoyl group | 322 |
| 5E | methylsulfonyl group | 293 |

Preparative Example 6

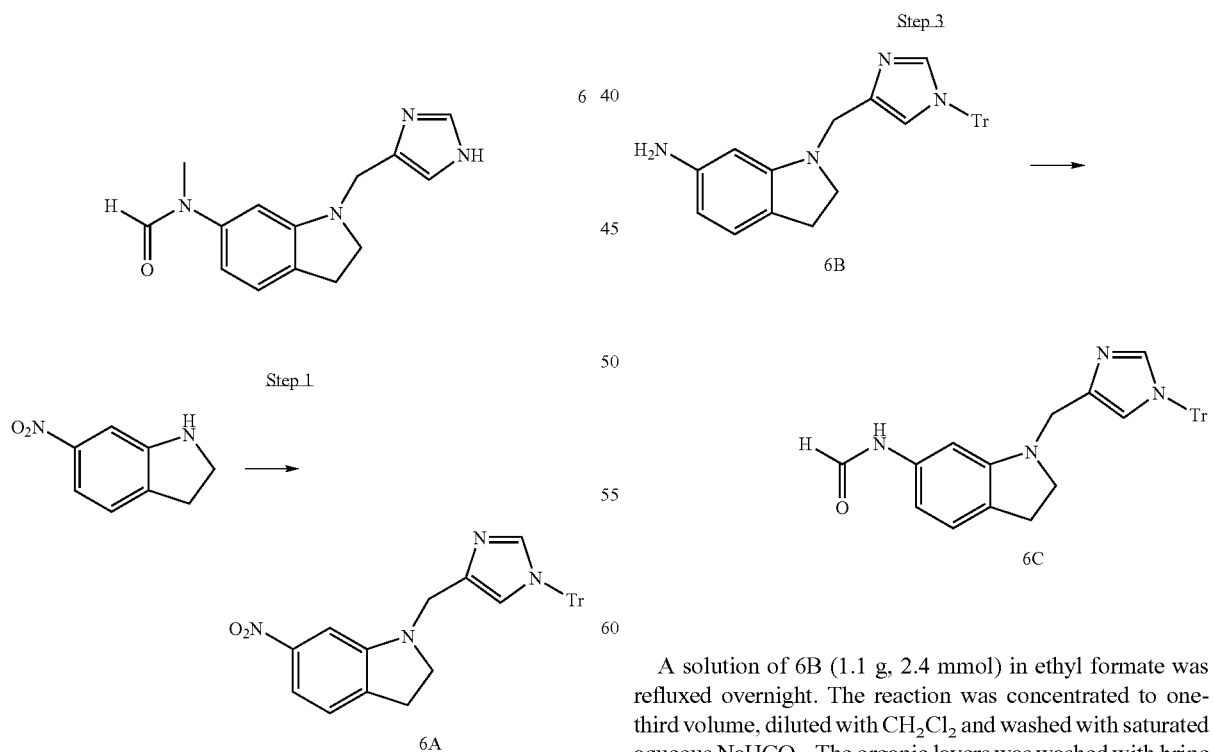

In a manner similar to that found in Example 4, Step 1, 6-nitroindoline was reacted with 1-tritylimidazole-4-carboxaldehyde and converted to 6A.

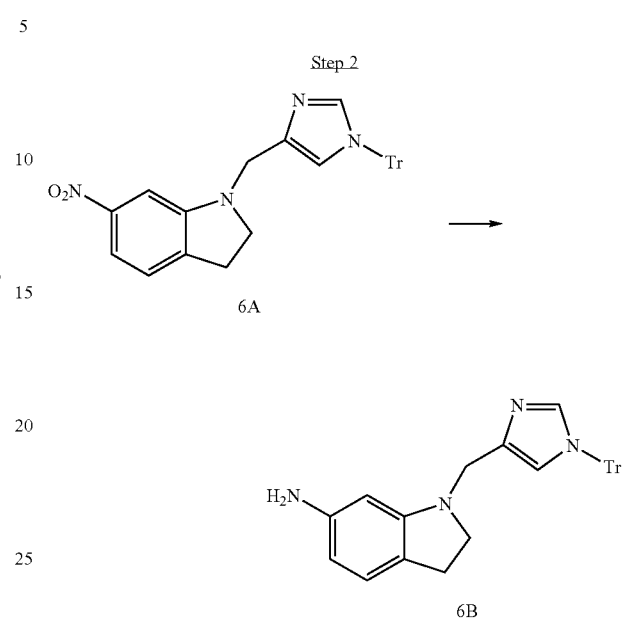

A mixture of 6A (3.0 g, 6.2 mmol) in EtOH was treated with 10% Pd/C and hydrogenated at 50 psi $H_2$ for 4 h. The reaction was filtered through celite and concentrated to provide the 6B as tan foam (2.75 g, 98%).

A solution of 6B (1.1 g, 2.4 mmol) in ethyl formate was refluxed overnight. The reaction was concentrated to one-third volume, diluted with $CH_2Cl_2$ and washed with saturated aqueous $NaHCO_3$. The organic layers was washed with brine and concentrated. Chromatography (30-100% EtOAc/hexanes) provided 6C as a yellow foam (0.41 g, 35%).

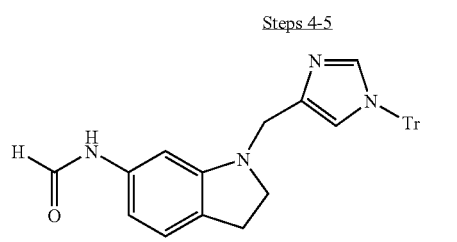

6C

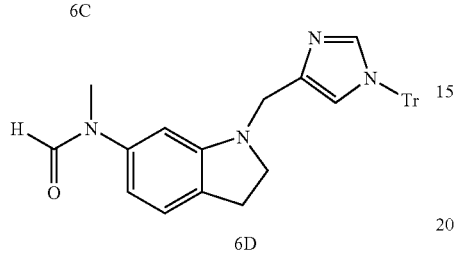

6D

A solution of 6C (0.17 g, 0.35 mmol) in THF (10 ml) was added slowly to a slurry of LAH (0.13 g, 3.5 mmol) in THF (10 ml). The reaction was refluxed for 1 h, cooled with an ice bath, and quenched slowly with water and then 10% aqueous NaOH. The mixture was diluted with EtOAc, filtered through celite and concentrated to provide a tan brown film. This material was then refluxed overnight in butyl formate. Chromatography (0-5% 7 N $NH_3$-MeOH/$CH_2Cl_2$) provided 6D as a yellow film (0.020 g, 11%).

A solution of 6D (0.014 g, 0.03 mmol) in $CH_2Cl_2$ (3 mL) was treated with $Et_3SiH$ (9 µL, 0.03 mmol) and TFA (28 µL, 0.3 mmol) and stirred at 20° C. for 2 h. Chromatography (5% 7 N $NH_3$-MeOH/$CH_2Cl_2$) provided the title compound 6 as a yellow film (0.006 g, 85%). LMCS m/z 257 (MH+).

Preparative Example 7

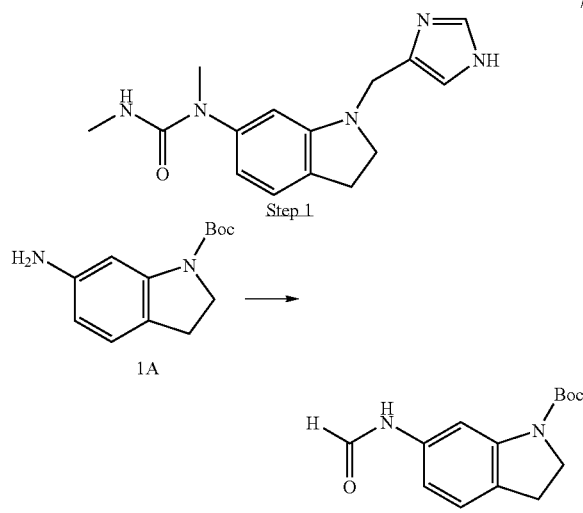

A sample of $Ac_2O$ (9.71 mL, 103 mmol) was cooled at 0° C. and treated with $HCO_2H$ (3.95 mL, 103 mmol) dropwise. The mixture was stirred at 0° C. for 5 min, and then heated at 55° C. for 2 h. The reaction was cooled to 0° C. and a solution of 1A (9 g, 38.4 mmol) in THF (100 mL) was added. The mixture was stirred at 0° C. for 30 min, and the solvent was removed under reduced pressure to yield 7A.

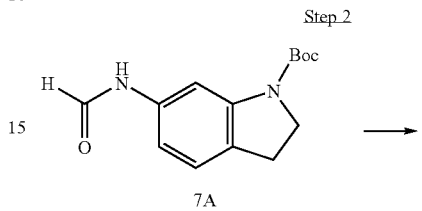

Compound 7A was dissolved in THF (100 mL), treated with 2M $BH_3$—$SMe_2$ in THF (77 mL, 142.8 mmol) and refluxed for 2 h. The reaction was then treated with MeOH and refluxed for 10 min. The mixture was then cooled to RT and concentrated under reduced pressure. The residue was dissolved in water and extracted with EtOAc (3×120 mL). The combined organic layer was dried ($Na_2SO_4$), filtered and concentrated give 7B (8.85 g, 93%).

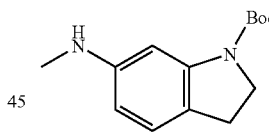

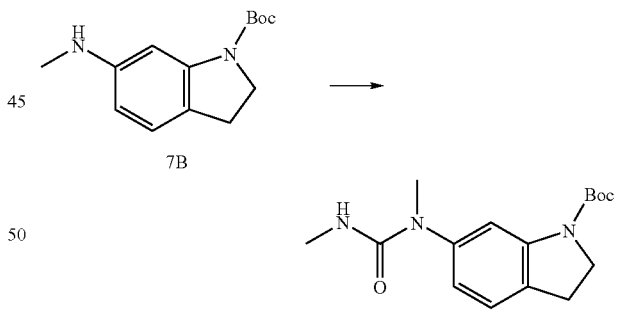

A solution of 7B (0.26 g, 1.05 mmol) in THF (10 mL) was treated with MeNCO (0.072 g, 1.26 mmol), stirred overnight, and concentrated to give 7C.

In a manner similar to that found in Example 1, Step 4 and Example 4, Step 1, 7C was deprotected and converted to the title compound 7. MS m/z 286 (MH+).

Compounds 7D-7N in TABLE 6 can be prepared starting from compound 7B, by reaction with isocyanates, acid chlorides or chloroformates, followed by deprotection and reductive alkylation as described above.

TABLE 6

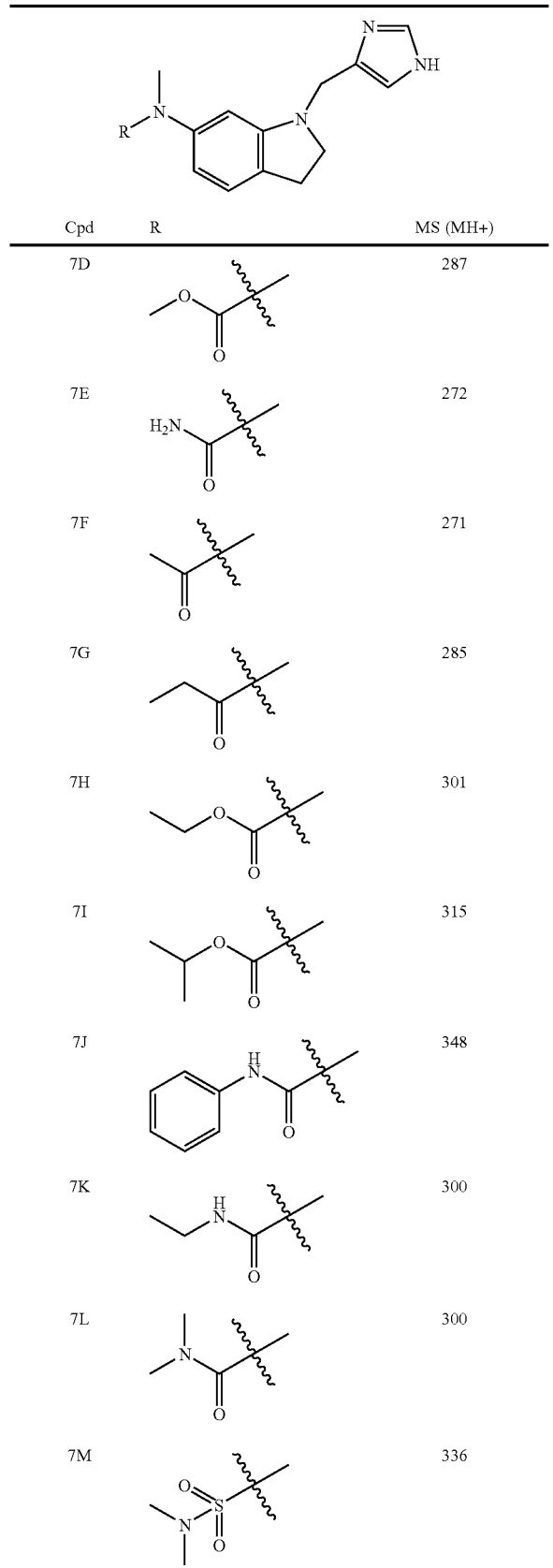

| Cpd | R | MS (MH+) |
|---|---|---|
| 7D | methyl ester (–C(CH3)(–)C(O)OCH3) | 287 |
| 7E | amide (–C(CH3)(–)C(O)NH2) | 272 |
| 7F | acetyl (–C(CH3)(–)C(O)CH3) | 271 |
| 7G | propanoyl (–C(CH3)(–)C(O)CH2CH3) | 285 |
| 7H | ethyl ester (–C(CH3)(–)C(O)OCH2CH3) | 301 |
| 7I | isopropyl ester | 315 |
| 7J | anilide (–C(CH3)(–)C(O)NHPh) | 348 |
| 7K | ethyl amide (–C(CH3)(–)C(O)NHEt) | 300 |
| 7L | N,N-dimethyl amide | 300 |
| 7M | N,N-dimethylsulfamoyl | 336 |

TABLE 6-continued

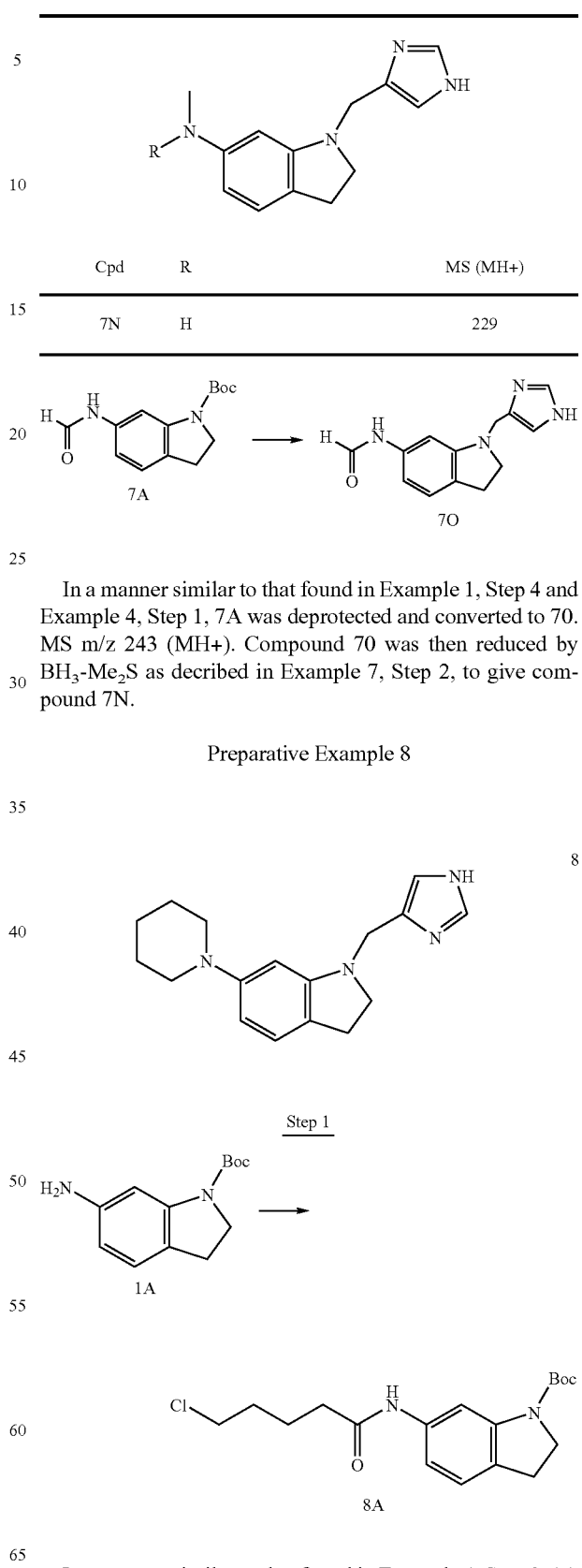

| Cpd | R | MS (MH+) |
|---|---|---|
| 7N | H | 229 |

In a manner similar to that found in Example 1, Step 4 and Example 4, Step 1, 7A was deprotected and converted to 7O. MS m/z 243 (MH+). Compound 7O was then reduced by BH3-Me2S as decribed in Example 7, Step 2, to give compound 7N.

Preparative Example 8

In a manner similar to that found in Example 4, Step 3, 1A was reacted with 5-chlorovaleryl chloride to give 8A.

Step 2

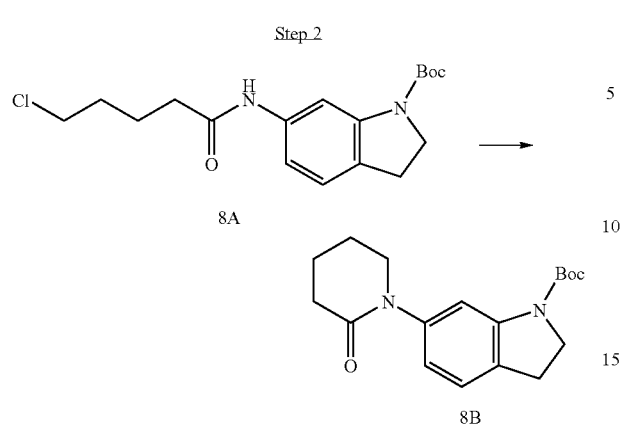

A stirred solution of compound 8A (3.1 g, 8 mmol) in THF (10 mL) was treated with 5 N NaOH (100 mL) and stirred overnight. The mixture was extracted with DCM (2×100 mL). Combined organic layer was dried ($Na_2SO_4$), filtered and concentrated under reduced pressure. Chromatography (30% EtOAc/hexanes) provided 8B (1.73 g, 68%) and recovered 8A (1.2 g).

Steps 3-5

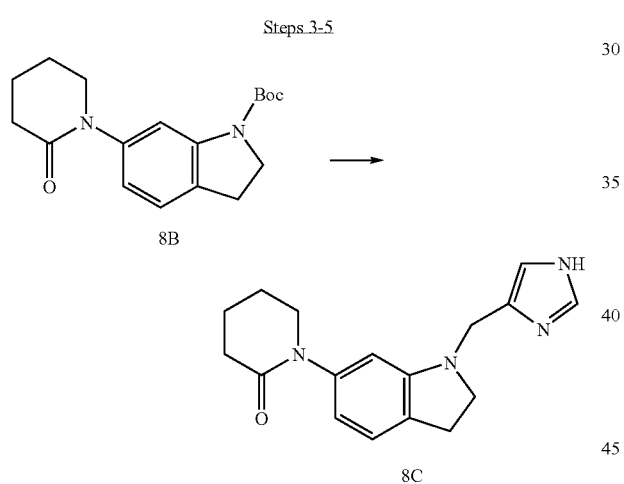

In a manner similar to that found in Example 1, Step 4 and Example 4, Step 1, 8B was deprotected and converted to 8C (MS m/z 297 MH+). 8C was then reacted with $BH_3$-THF in a manner similar to that found in Example 7, Step 2 to provide the title compound 8. MS m/z 283 (MH+).

Preparative Example 9

-continued

Step 1

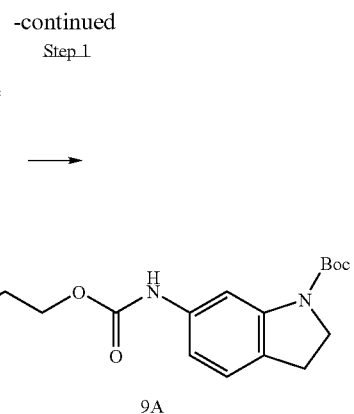

In a manner similar to that found in Example 4, Step 3, 1A was reacted with 2-chloroethyl chloroformate to provide 9A.

Steps 2-4

To a stirred solution of compound 9A (0.41 g, 1.2 mmol) in DMF (5 mL) was added NaH (0.1 g, 60% in oil). The mixture was stirred overnight. Solvent was removed under high vacuum and EtOAc (20 mL) was added. The mixture was washed with 1 M HCl quickly, dried ($Na_2SO_4$), filtered and concentrated under reduced pressure. The residue was purified by flash column chromatography (5% MeOH/DCM) to give 9B (0.23 g).

In a manner similar to that found in Example 1, Step 4 and Example 4, Step 1, 9B was deprotected and converted to the title compound 9. MS m/z 285 (MH+).

Preparative Example 10

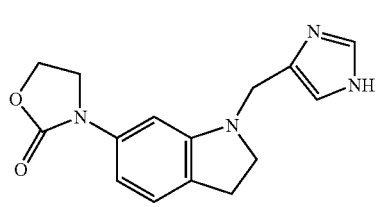

9

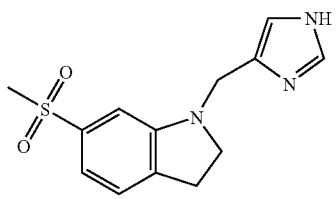

10

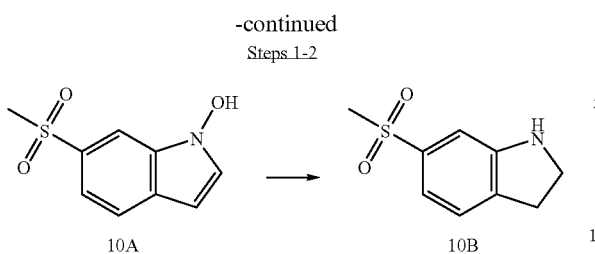

To a stirred solution of 1-hydroxy-6-methylsulfonylindole 10A (1.5 g, 7.1 mmol) in TFA (20 mL) was added 1 M BH$_3$-THF (20 mL). The reaction was stirred at RT for 30 min. The reaction was concentrated and treated with 1 N NaOH. The mixture was extracted with DCM (3×50 mL). The combined organic layer was dried (Na$_2$SO$_4$), filtered and concentrated under reduced pressure. Flash chromatography (30-50% EtOAc/hexanes) provided 10B (1.05 g, 75%).

In a manner similar to that found in Example 4, Step 1, 10B was reacted with 4-imidazolecarboxaldehyde to provide the title compound 10. MS m/z 278 (MH+).

Preparative Example 11

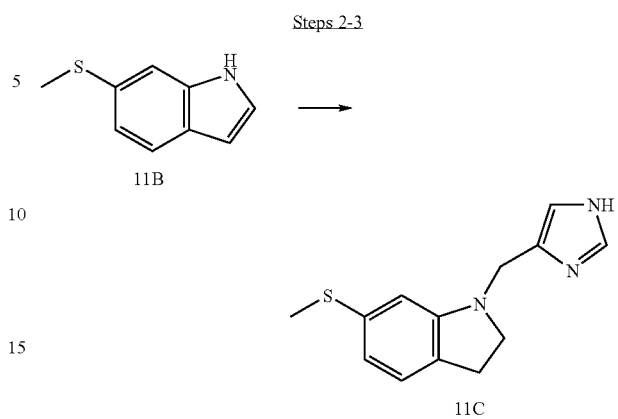

To a suspension of KH (30% in mineral oil, washed with hexanes, 0.68 g, 5.1 mmol) in anhydrous THF (10 mL) at 0° C. under argon was added a solution of 11A (1 g, 5.1 mmol) in THF (10 mL). After 15 min, the solution was cooled to −78° C. and treated with t-BuLi (1.7 M in pentane, 6 mL, 10 mmol) dropwise. After 15 min (−78° C.), DMS (0.92 mL, 10.2 mmol) was added dropwise. The solution was warmed gradually to RT and stirred overnight. Then the reaction was carefully quenched by saturated NH$_4$Cl (15 mL) and filtered. The filtrate was diluted with water and extracted with EtOAc (3×50 mL). The combined organic layers were dried (MgSO$_4$), filtered, and concentrated under vacuum. The residue was purified by flash column chromatography (5-25% EtOAc/hexanes) to give compound 11B (1.2 g).

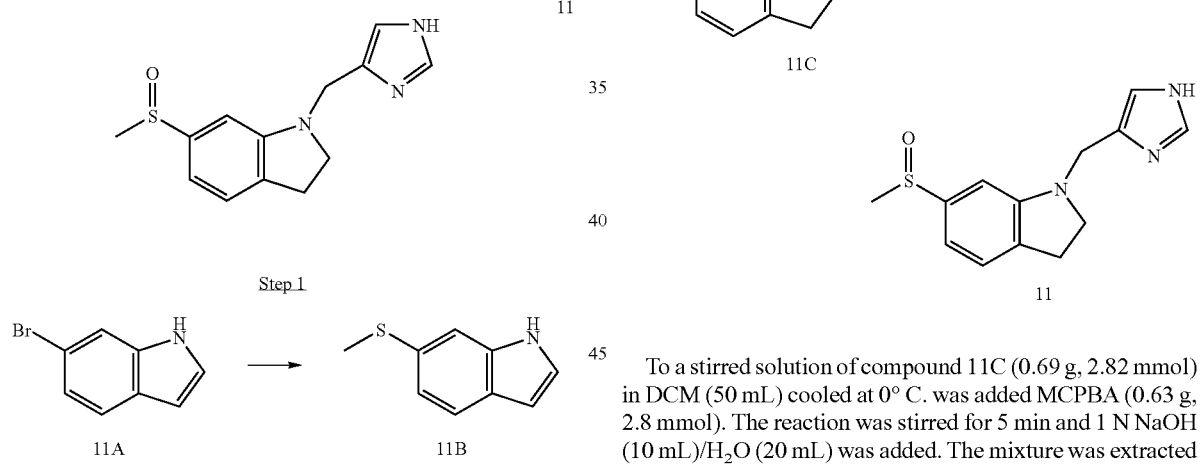

In a manner similar to that found in Example 10, Step 1, and Example 4, Step 1, 11B was reduced with BH$_3$-THF and then converted to 11C. MS m/z 246 (MH+).

To a stirred solution of compound 11C (0.69 g, 2.82 mmol) in DCM (50 mL) cooled at 0° C. was added MCPBA (0.63 g, 2.8 mmol). The reaction was stirred for 5 min and 1 N NaOH (10 mL)/H$_2$O (20 mL) was added. The mixture was extracted with DCM (3×50 mL). The combined organic layer was dried (Na$_2$SO$_4$), filtered and concentrated under reduced pressure. Chromatography (2-5% 7N NH$_3$-MeOH/DCM) provided 11 (0.183 g, 25%). MS m/z 262 (MH+).

Preparative Example 12

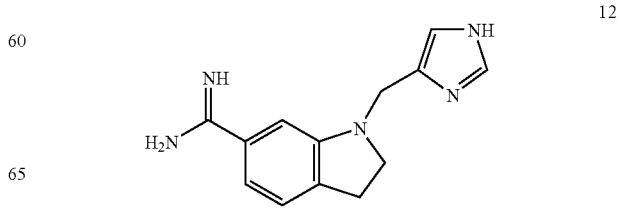

-continued

Steps 1-2

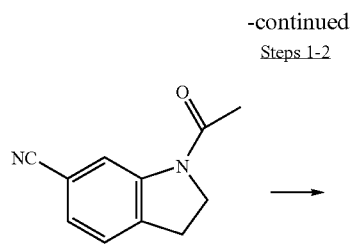

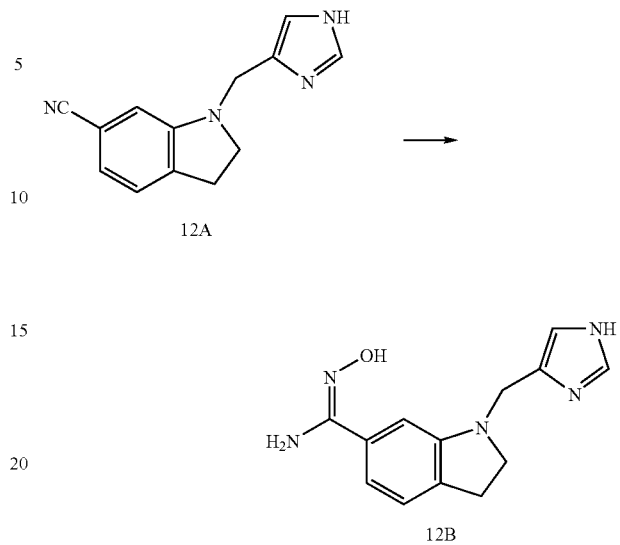

1-Acetyl-6-cyanoindoline (2.4 g, 12.9 mmol, Tetrahedron, 1967, 23, 3823) was stirred in a solution containing 5 N NaOH (20 mL), MeOH (60 mL) and dioxane (60 mL). The mixture was stirred at RT over the weekend. Solvent was removed under reduced pressure and the residue was partitioned between water (100 mL) and DCM (100 mL). Aqueous layer was extracted with DCM (2×75 mL). Combined organic layer was dried ($Na_2SO_4$), filtered and concentrated under reduced pressure. Chromatography (10-30% EtOAc/hexanes) provided 6-cyanoindoline (0.95 g, 51%) which was then converted to 12A in a manner similar to that found in Example 4, Step 1.

Compound 12B can be prepared from compound 12A as follows: To a stirred solution of 12A (0.197 g, 0.88 mmol) in EtOH (100 mL) was added $NH_2OH$ (50% in $H_2O$, 0.5 mL, 15 mmol). The reaction was refluxed for 24 h. The mixture was concentrated and subjected to chromatography (DCM containing 10-15% of 7N $NH_3$/MeOH) to give 12B (0.22 g, 98% yield). MS m/z 258 (MH+).

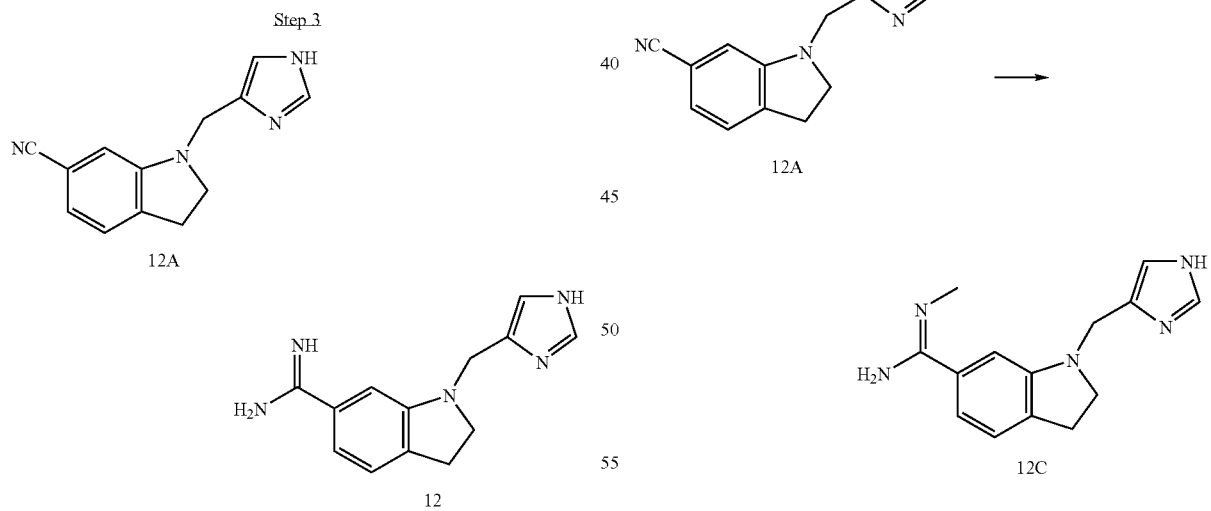

To a stirred solution of compound 12A (0.1 g, 0.45 mmol) in MeOH (60 mL) was bubbled in HCl gas at 0° C. for 15 min. The reaction was stirred overnight and solvent was removed under reduced pressure. The residue was dissolved in 2N $NH_3$/MeOH (50 mL) and stirred for 4 h. The mixture was concentrated and subjected to chromatography (DCM containing 5-15% of 7N $NH_3$/MeOH) to give the title compound 12 (0.062 g, 57%). MS m/z 242 (MH+).

Compound 12C can be prepared from compound 12A as follows: Compound 12A (0.1 g, 0.44 mmol) was dissolved in EtOH (2 mL) and methylamine (40% in $H_2O$, 1 mL) was added. The mixture was refluxed overnight. Solvent was removed under reduced pressure and the residue was purified by HPLC (using Waters SunFire™ Prep C18 5 μM, 19-100 mm column, gradient: 5-90% $H_2O$/$CH_3CN$) to give 12C (0.028 g, 25%). MS m/z 256 (MH+).

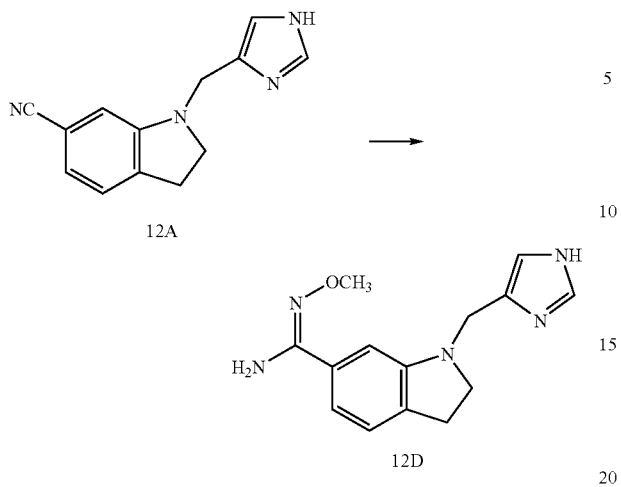

Compound 12D can be prepared from compound 12A as follows: To a stirred solution of compound 12A (0.3 g, 1.34 mmol) in MeOH (30 mL) was bubbled in HCl gas at 0° C. for 15 min. The reaction was stirred overnight and solvent was removed under reduced pressure. The residue was dissolved in MeOH (30 mL), treated with TEA (3.4 mL, 24 mmol) and O-methylhydroxylamine hydrochloride (2 g, 24 mmol), and stirred for 24 h. Solvent was removed under reduced pressure and the residue was purified (reverse phase HPLC) to give 12D (0.16 g, 44%). MS m/z 272 (MH+).

Preparative Examle 13

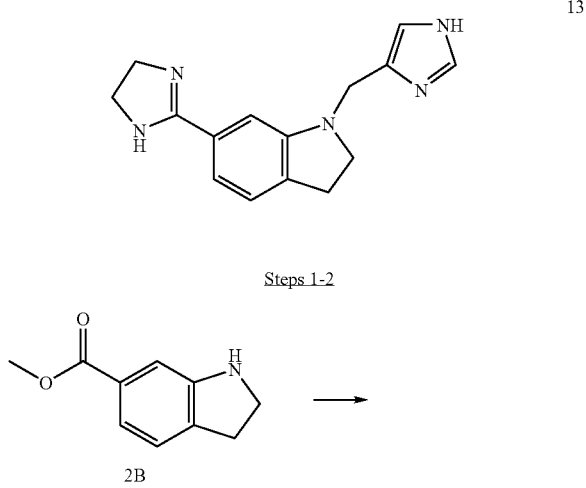

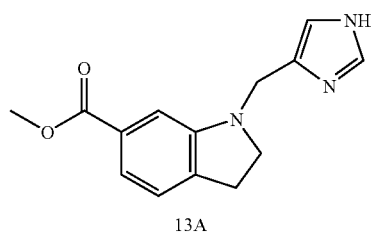

In a manner similar to that found in Example 4, Step 1, 2B was reacted with 4-imidazolecarboxaldehyde to provide 13A. A mixture of compound 13A (0.075 g, 0.3 mmol), 1,2-aminoethane (0.067 mL) and AlMe$_3$ (2M in toluene, 0.5 mL) was refluxed overnight. The reaction was concentrated and purified by preparative HPLC (as described previously) to give the title compound 13. MS m/z 268 (MH+).

Preparative Example 14

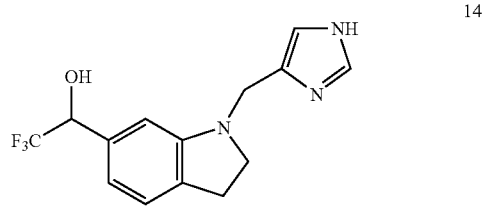

Step 1

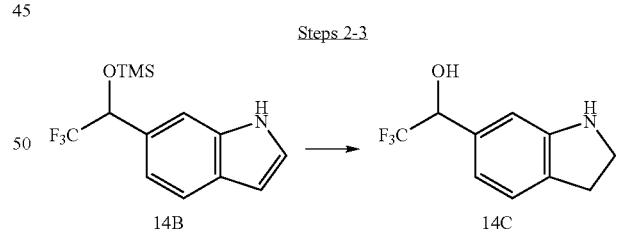

To a stirred solution of compound 14A (0.28 g, 1.93 mmol) in THF (10 mL) was added TMS-CF$_3$ (0.5 M in THF, 3.8 mL, 1.9 mmol) and CsF (0.61 g, 4 mmol). The reaction was stirred at RT for 4 h. Solvent was removed under reduced pressure and H$_2$O (10 mL) was added. The aqueous mixture was extracted with EtOAc (3×15 mL). The combined organic layer was dried (Na$_2$SO$_4$), filtered and concentrated to give crude 14B. $^{19}$F NMR (CDCl3): 78.78 (d).

Steps 2-3

To a stirred solution of compound 14B (0.2 g, 0.7 mmol) in DCM (25 mL) was added NaCNBH$_3$ (0.3 g, 4.76 mmol) and AcOH (0.1 mL). The reaction was stirred overnight and quenched with sat. NaHCO$_3$. The aqueous layer was extracted with EtOAc (20 mL×3). The combined organic layer was dried (Na$_2$SO$_4$), filtered and concentrated to give 14C.

In a manner similar to that found in Example 4, Step 1, 14C reacted with 4-imidazolecarboxaldehyde to provide the title compound 14. MS m/z 298 (MH+).

Preparative Example 15

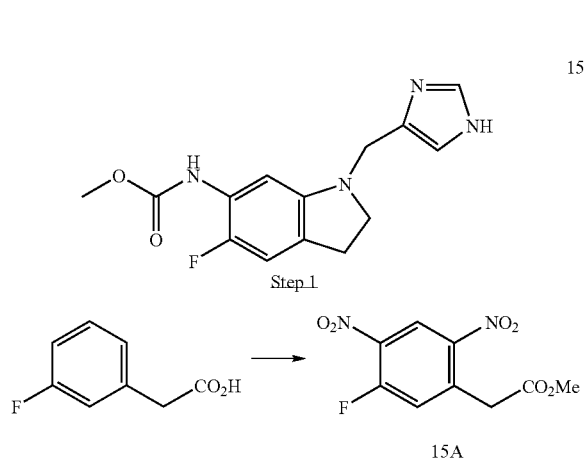

A stirred solution of 3-fluorophenylacetic acid (10.1 g, 65.5 mmol) in concentrated H$_2$SO$_4$ (20 mL) was treated with a solution of HNO$_3$ (90%, 12 mL) and conc. H$_2$SO$_4$ (15 mL) dropwise through an addition funnel while maintaining a temperature between 20-35° C. by water bath. The reaction was stirred overnight at 35° C. and then poured onto ice. The precipitate was filtered, washed with water, and then dried under vacuum at 80° C. for 5 h. The solid was dissolved in MeOH and 0.5 mL conc. H$_2$SO$_4$ was added. The reaction was refluxed for 5 h and cooled to RT overnight. The mixture was cooled in an ice bath and 3 N NaOH was added until pH=5 was obtained. The mixture was concentrated under reduced pressure, diluted with water, and extracted with EtOAc. The combined organic layer was dried (MgSO$_4$), filtered and concentrated. Chromatography (5-20% EtOAc/hexanes) provided 15A (40%).

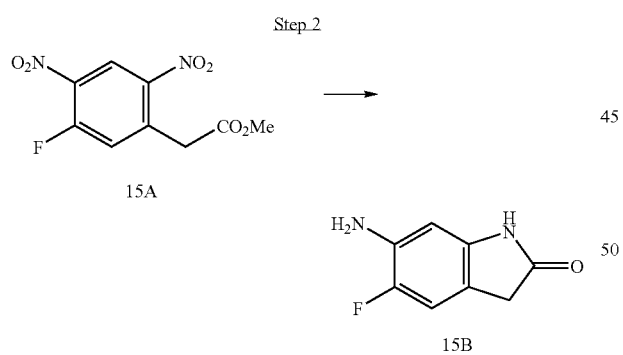

To a stirred solution of compound 15A (6.83 g, 26.5 mmol) in MeOH (80 mL) was added 10% Pd/C (0.68 g). The reaction was stirred under H$_2$ (1 atm) overnight. The mixture was filtered through celite and the solvent was removed under reduced pressure to give 5.05 g of the hydrogenation product (96%). This material was dissolved in 10% HCl (50 mL) and the mixture was refluxed for 0.5 h. The reaction was cooled to RT, basified with 50% NaOH to pH=8, and extracted with EtOAc (3×100 mL). The combined organic layer was dried (MgSO$_4$), filtered and concentrated to give 15B (3.92 g, 93%).

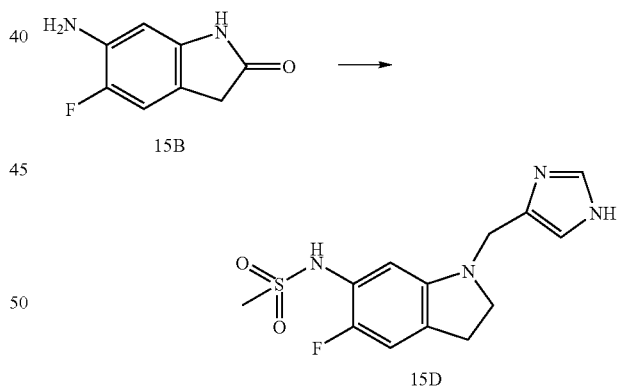

To a suspension of compound 15B (0.305 g, 1.84 mmol) was added pyridine (0.3 mL, 3.68 mmol) and ClCO$_2$Me (0.24 mL, 3.11 mmol) The reaction was stirred at RT for 2 h and the precipitate was filtered. The precipitate was washed with DCM, sat. NH$_4$Cl, H$_2$O, and 3 N HCl. The DCM layer was dried (MgSO$_4$), filtered and concentrated and combined with the precipitate (dried on high vacuum) to give 0.455 g of the corresponding methylcarbamate. The solid was dissolved in THF (10 mL) and BH$_3$—SMe$_2$ (2 M/THF, 1.84 mL, 3.68 mmol) was added. The reaction was refluxed for 3 h, quenched with MeOH, and refluxed for another 10 min. Solvent was removed under reduced pressure and the residue was purified by flash column chromatography (10-25% EtOAc/hexanes) to give 15C (0.24 g, 63%).

Compound 15C was reacted with 4-imidazolecarboxaldehyde to provide the title compound 15 in a manner similar to that described in Example 4, Step 1. MS m/z 291 (MH+)

Compound 15D can be prepared starting from compound 15B, by using methanesulfonic anhydride/pyridine, followed by BH$_3$ reduction and reductive alkylation with 4-imidazolecarboxyaldehyde as described previously. MS m/z 311, (MH+)

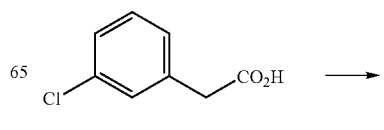

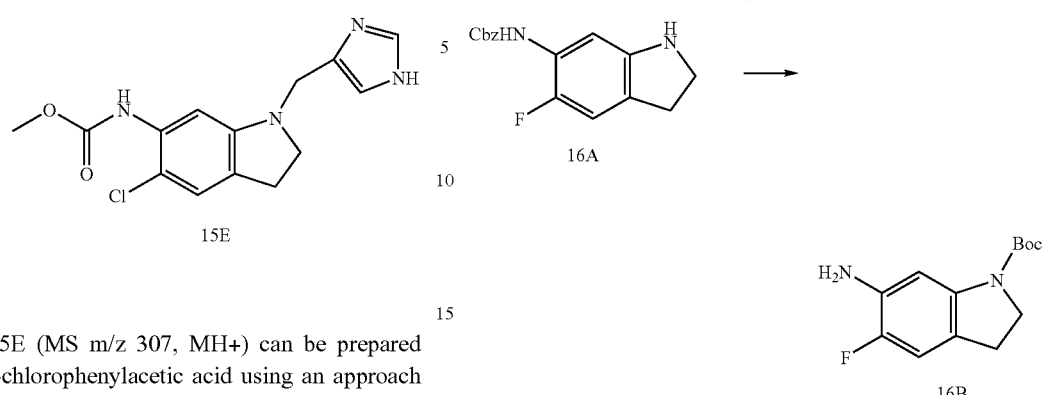

Compound 15E (MS m/z 307, MH+) can be prepared starting from 3-chlorophenylacetic acid using an approach similar to that described in Example 15, except that Step 2 (nitro group reduction) was accomplished using Raney Ni as described below: To a stirred solution of 3-chloro-4,6-dinitrophenylacetic acid in EtOH was added Raney Ni. The reaction was stirred under $H_2$ (1 atm) for 4 h. The mixture was filtered through celite and solvent was removed under reduced pressure. This material was dissolved in 10% HCl (10 mL) and the mixture was refluxed for 0.5 h. The reaction was cooled to RT, basified with 50% NaOH to pH=8, and extracted with EtOAc (30 mL×5). Combined organic layer was dried ($Na_2SO_4$), filtered and concentrated under reduced pressure. The residue was purified by flash column chromatography (60-80% EtOAc/hexanes).

Preparative Example 16

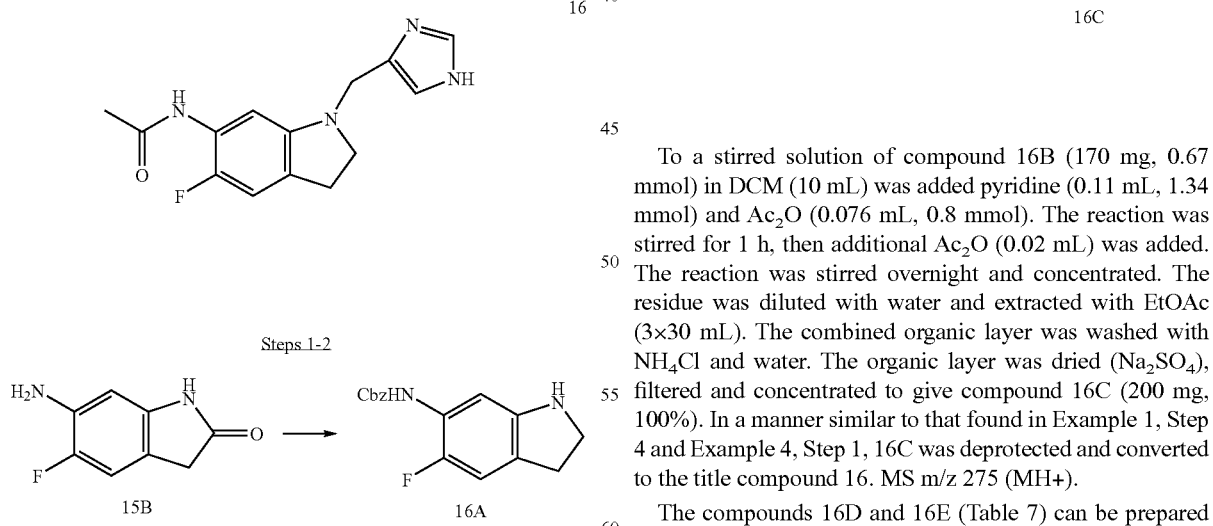

In a manner similar to that found in Example 15, Steps 3-4, 15B was reacted with benzylchloroformate and then reduced with $BH_3$—$SMe_2$ to provide 16A.

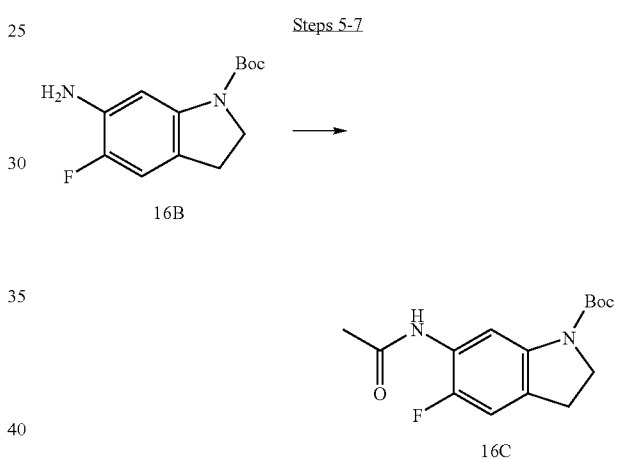

In a manner similar to that found in Example 1, Steps 1-2, 16A was protected and then hydrogenated to provide 16B.

To a stirred solution of compound 16B (170 mg, 0.67 mmol) in DCM (10 mL) was added pyridine (0.11 mL, 1.34 mmol) and $Ac_2O$ (0.076 mL, 0.8 mmol). The reaction was stirred for 1 h, then additional $Ac_2O$ (0.02 mL) was added. The reaction was stirred overnight and concentrated. The residue was diluted with water and extracted with EtOAc (3×30 mL). The combined organic layer was washed with $NH_4Cl$ and water. The organic layer was dried ($Na_2SO_4$), filtered and concentrated to give compound 16C (200 mg, 100%). In a manner similar to that found in Example 1, Step 4 and Example 4, Step 1, 16C was deprotected and converted to the title compound 16. MS m/z 275 (MH+).

The compounds 16D and 16E (Table 7) can be prepared starting from compound 16B, using methylisocyanate or N,N-dimethylsulfamoylchloride/2,6-lutidine, followed by Boc-deprotection and reductive alkylation as described above. Compound 16F (Table 7) can be prepared from compound 16A by performing reductive alkylation with 4-imidazolecarboxyaldehyde and hydrogenation to remove the Cbz group, as described above.

TABLE 7

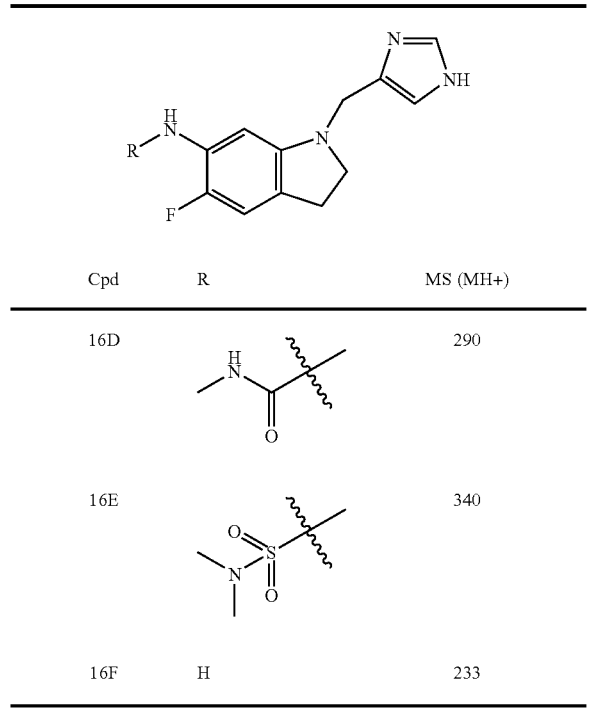

| Cpd | R | MS (MH+) |
|---|---|---|
| 16D | (N-methyl carboxamide, dimethyl) | 290 |
| 16E | (N,N-dimethylsulfamoyl, dimethyl) | 340 |
| 16F | H | 233 |

Preparative Example 17

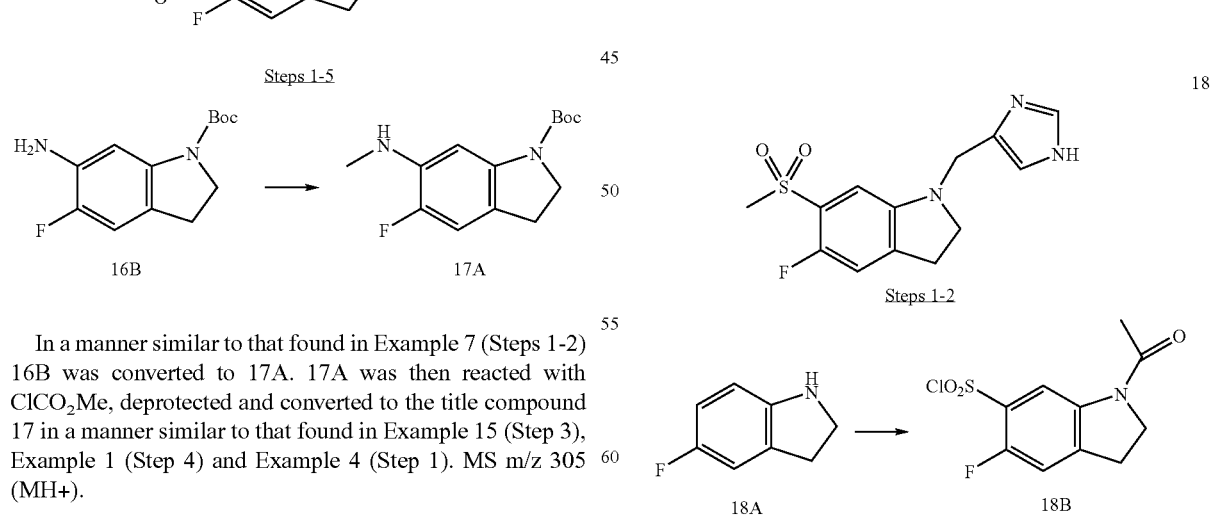

In a manner similar to that found in Example 7 (Steps 1-2) 16B was converted to 17A. 17A was then reacted with ClCO₂Me, deprotected and converted to the title compound 17 in a manner similar to that found in Example 15 (Step 3), Example 1 (Step 4) and Example 4 (Step 1). MS m/z 305 (MH+).

The following compounds (TABLE 8) can be prepared by treating compound 17A with Ac₂O, methanesulfonic anhydride, N,N-dimethylsulfamoyl chloride or MeNCO respectively, followed by Boc-deprotection and reductive alkylation as described previously.

TABLE 8

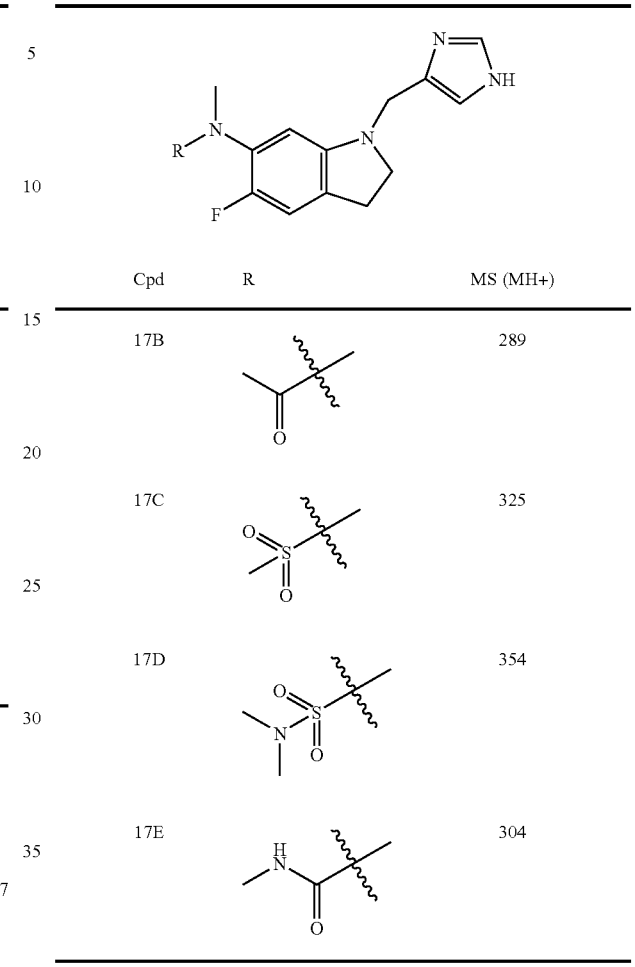

| Cpd | R | MS (MH+) |
|---|---|---|
| 17B | (acetyl) | 289 |
| 17C | (methylsulfonyl) | 325 |
| 17D | (N,N-dimethylsulfamoyl) | 354 |
| 17E | (N-methyl carboxamide) | 304 |

Preparative Example 18

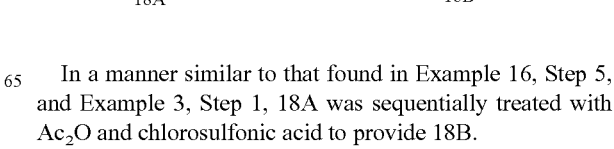

In a manner similar to that found in Example 16, Step 5, and Example 3, Step 1, 18A was sequentially treated with Ac₂O and chlorosulfonic acid to provide 18B.

Step 3-5

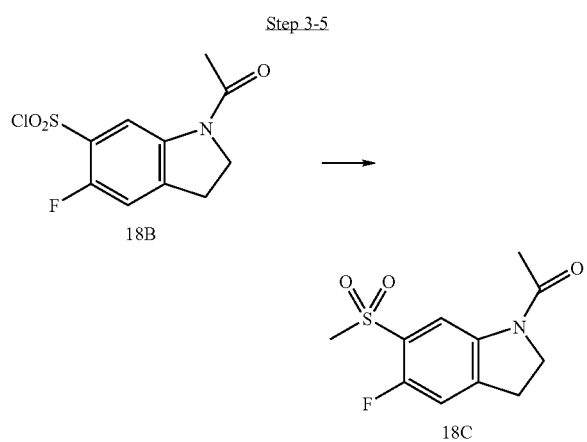

A stirred solution of Na$_2$SO$_3$ (1.15 g, 9.15 mmol) and Na$_2$HCO$_3$ (0.81 g, 9.63 mmol) in H$_2$O (16 mL) at 80° C. was treated with 18B (1.33 g, 4.82 mmol). The mixture was stirred at 80° C. for 1 h, and then allowed to cool to RT and stand overnight. The reaction was concentrated and then residue dried under high vacuum. To this residue was carefully added NaHCO$_3$ (0.77 g, 9.15 mmol) and dimethyl sulfate (0.69 mL, 7.33 mmol), while water was added through addition funnel to keep the reaction mixture stirring. The reaction was heated at reflux over the weekend. After the mixture was cooled to 75° C., benzene (5 mL) was added. The mixture was stirred briefly, cooled to RT, and ammonia was added. After solvent was removed under reduced pressure, the residue was mixed with 2N NaOH and extracted with EtOAc (3×50 mL). The organic layer was dried (MgSO$_4$), filtered, and concentrated under reduced pressure. Chromatography (0-5% MeOH/DCM) provided 18C (0.399 g, 32%).

In a manner similar to that found in Example 3, Step 3, and Example 4, Step 1, 18C was deprotected and converted to the title compound 18. MS m/z 296 (MH+).

Preparative Example 19

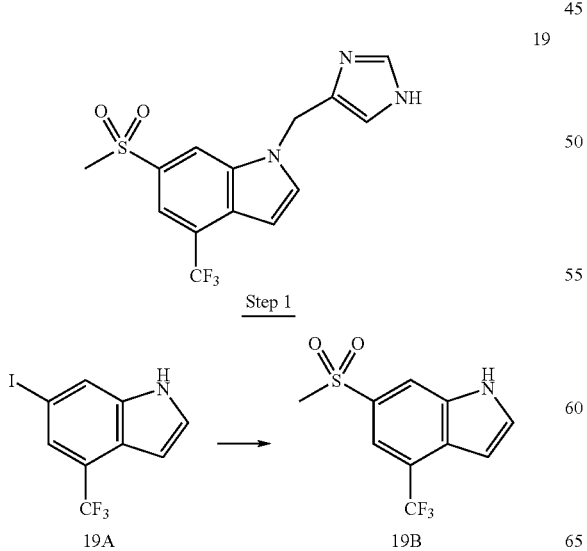

To a stirred solution of compound 19A (0.86 g, 2.76 mmol, Tetrahedron, 2002, 58, 3605) in DMSO (10 mL) was added sodium sulfinate (0.37 g, 3.64 mmol) and cupper triflate benzene complex (42 mg, 0.083 mmol). The mixture was stirred for 5 min and a solution of N,N'-dimethylethylene-diamine (0.32 mL, 3 mmol) in DMSO (3 mL) was added. The reaction was heated at 110° C. for 12 h and then concentrated. The residue was purified by flash column chromatography (10% MeOH/DCM) to give compound 19B (0.6 g, 81% yield).

Step 2

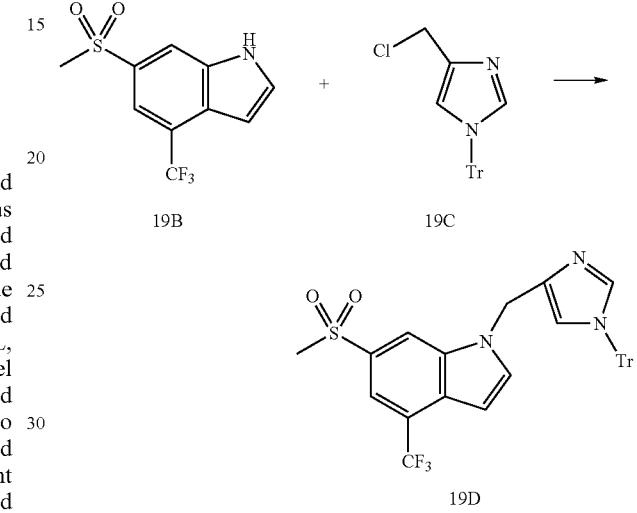

To a stirred solution of compound 19B (0.1 g, 0.38 mmol) in DMF (15 mL) was added NaH (0.08 g). The mixture was stirred for 5 min, and compound 19C (0.1 g, J. Med. Chem. 2002, 45, 533) was added. The reaction was stirred for 24 h. Solvent was removed under high vacuum and the residue was purified by flash column chromatography (20% EtOAc/DCM) to give 19D (0.08 g, 36% yield).

Step 3

Compound 19D was dissolved in EtOH (10 mL) and treated with 10% Pd/C (10 mg). The reaction was stirred under H$_2$ (1 atm) at 45° C. for 16 h. The mixture was filtered through celite and the filtrate was concentrated. The residue was purified by flash column chromatography (10% MeOH/DCM) to give the title compound 19 (30 mg, 63%). MS m/z 344 (MH+).

Preparative Example 20

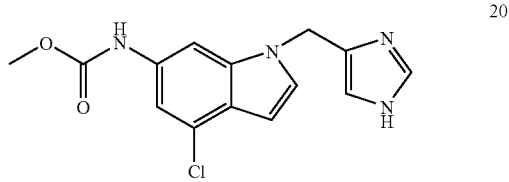

-continued

Step 1

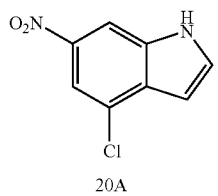
20A

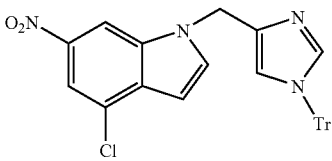
20B

Compound 20A was prepared from 2-chloro-4,6-dinitrotoluene (J. Org. Chem., 1985, 50, 1041-1045) as described in U.S. Pat. No. 5,969,155.

Compound 20A (0.8 g, 4 mmol) in acetone (40 mL) was treated with 19C (1.74 g, 4.8 mmol) and $K_2CO_3$ (0.67 g, 4.8 mmol) and then refluxed for 48 h. Solvent was removed under reduced pressure and the residue was dissolved in DCM (600 mL) and washed with water and brine. The organic layer was dried ($Na_2SO_4$), filtered and concentrated. The residue was purified by chromatography (0.5% MeOH/DCM) to give 20B (1.9 g, 91%) as yellow solid. $^1$H NMR (CDCl$_3$): 8.21 (s, 1H), 8.0 (d, 1H), 7.53 (d, 1H), 7.41 (s, 1H), 7.3-7.0 (15H), 6.75 (s, 1H), 6.65 (d, 1 H), 5.26 (s, 2 H).

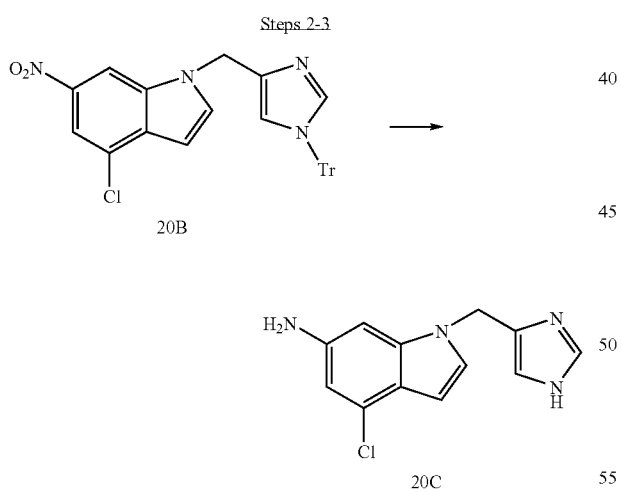

To a stirred solution of compound 20B (1.88 g, 3.62 mmol) in EtOH (70 mL) was added $SnCl_2\cdot 2H_2O$ (3.27 g, 14.48 mmol). The reaction was refluxed for 3 h and solvent was removed under reduced pressure. The residue was diluted with sat. NaHCO$_3$ (120 mL) and extracted with EtOAc (3×200 mL). The combined organic layer was washed with sat. NaHCO$_3$ and brine; then dried (Na$_2$SO$_4$), filtered and concentrated under to give 1.8 g of crude compound 20C. The crude material can be carried to the next reaction without further purification. A small portion of the crude material was purified by flash column chromatography (DCM containing 2-4% 7N NH$_3$/MeOH) to give pure compound 20C. MS m/z 247 (MH+).

To a stirred solution of crude compound 20C (0.6 g, 2.43 mmol) in DCM (10 mL) was added TEA (0.34 mL, 2.46 mmol) and ClCO$_2$Me (0.19 mL, 2.43 mmol). The reaction was stirred at RT overnight and quenched with 2N NaOH (10 mL). Solvent was removed under reduced pressure and the residue was partitioned between H$_2$O and EtOAc. The aqueous layer was extracted with EtOAc (3×30 mL). The combined organic layer was dried (Na$_2$SO$_4$), filtered and concentrated under reduced pressure. The residue was purified by flash column chromatography (DCM containing 2% 7N NH$_3$/MeOH). The fraction that contained the desired product was further purified by preparative TLC (1000 microns) to give pure title compound 20. MS m/z 305 (MH+).

Preparative Example 21

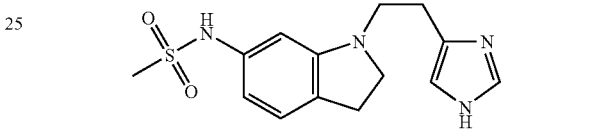
21

Step 1

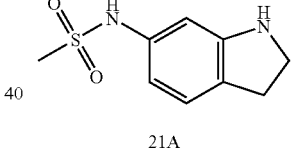
21A

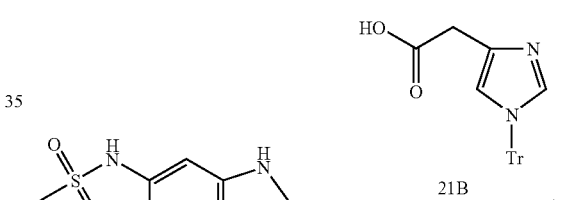
21B

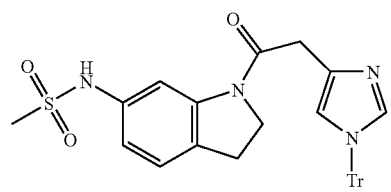
21C

Compound 21A was prepared by treating compound 5A with TFA as described previously Example 1, Step 4.

A stirred solution of compound 21A (0.5 g, 2.4 mmol) and compound 21B (0.87 g, 2.4 mmol, Bioconjugate Chem. 2002, 13, 333) in DMF (25 mL) was treated with HATU (0.95 g, 2.5 mmol) and stirred overnight. Solvent was removed under high vacuum and water (50 mL) was added. The mixture was extracted DCM (3×50 mL). The combined organic layer was dried (Na$_2$SO$_4$), filtered and concentrated under reduced pressure. The residue was purified by flash column chromatography (10% MeOH/DCM) to give 21C in (1.2 g, 89%).

Steps 2-3

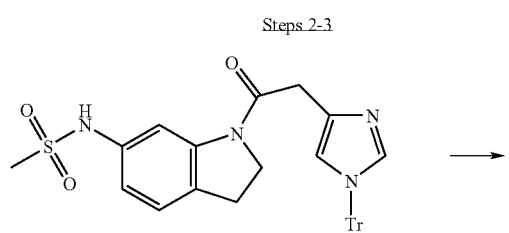

21C

21D

To a stirred solution of compound 21C (1.2 g, 2.1 mmol) in THF (50 mL) was added BH$_3$-THF (2 M, 5 mL). The mixture was heated at 80° C. for 12 h. The reaction was cooled to RT and MeOH (15 mL) was added slowly. Solvent was removed under reduced pressure and the residue was partitioned between EtOAc and water. The organic layer was dried (Na$_2$SO$_4$), filtered and concentrated under reduced pressure to give 21D (0.85 g, 74%).

Compound 21D was then hydrogenated at 80° C. for 18 h in a manner similar to that described in Example 19, Step 3 to provide the title compound 21. MS m/z 307 (MH+).

Preparative Example 22

22

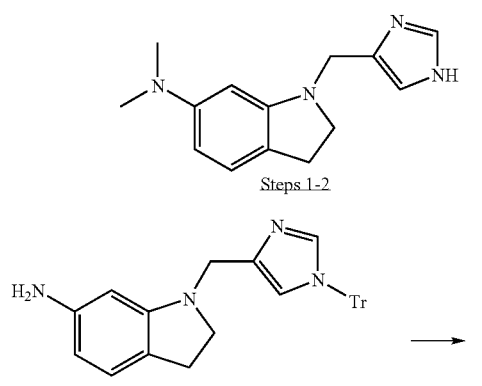

Steps 1-2

6B

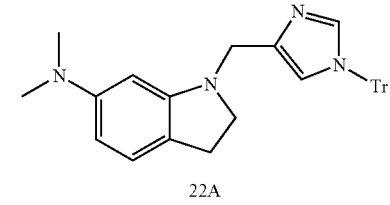

22A

To compound 6B (0.38 g, 0.84 mmol) in THF at 0° C. under Ar was added n-BuLi (2.5 M in hexanes, 1.01 mL, 2.53 mmol). The mixture was stirred at 0° C. for 1 h, and then treated with MeI (0.052 mL, 0.84 mmol). The reaction was stirred at 0° C. for 1 h, and then treated with saturated aqueous NH$_4$Cl. THF was removed under reduced pressure and the aqueous layer was extracted with EtOAc (3×50 mL). The organic layer was dried (MgSO$_4$), filtered and concentrated under reduced pressure. Chromatography (2-2.5% of 7% NH$_3$-MeOH/DCM) provided 22A (0.179 g, 44%).

In a manner similar to that found in Example 6, Step 5, 22A was deprotected to provide the title compound 22. MS m/z 243 (MH+).

Preparative Example 23

23

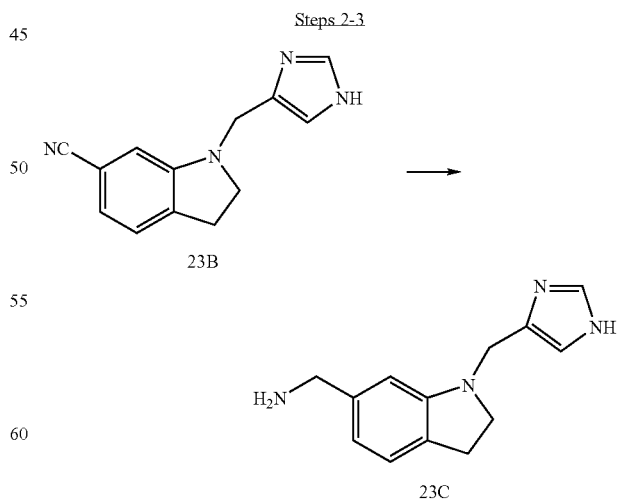

Step 1

23A

23B

In a manner similar to that found in Example 4, Step 1, 23A (Tetrahedron 1967, 23, 3823) was reacted with 4-imidazole-carboxaldehyde to provide 23B.

Steps 2-3

23B

23C

A solution of 23B (0.050 g, 0.15 mmol) in 1 M NH$_3$-MeOH (30 mL) was treated with Raney nickel, hydrogenated (35 psi H$_2$) for 2 h, and filtered through celite. Chromatography (3-15% 7 N NH₃-MeOH/CH₂Cl₂) provided 23C as a yellow film (0.029 g, 85%). LMCS m/z 271 (MH+).

In a manner similar to that found in Example 4, Step 3, 23C was reacted with AcCl to provide the title compound 23. LMCS m/z 229 (MH+).

Preparative Example 24

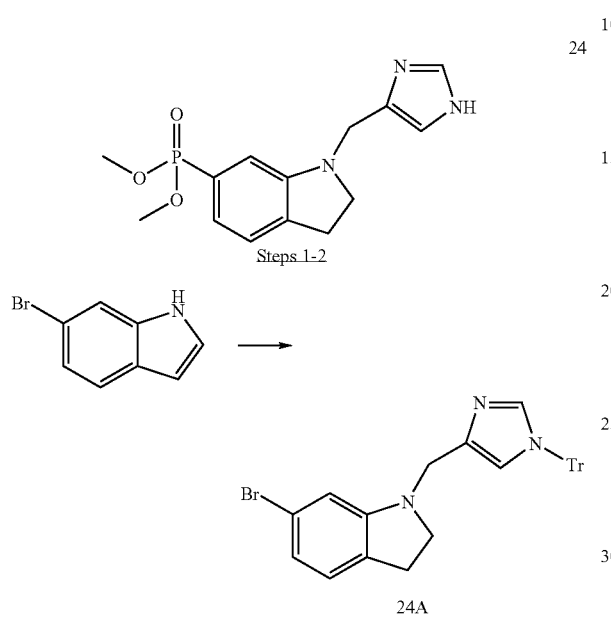

In a manner similar to that found in Example 14 (Step 2) and Example 4 (Step 1), 6-bromoindole was reduced with NaCNBH₃ and reacted with 1-tritylimidazole-4-carboxaldehyde to provide 24A.

A slurry of 24A (0.5 g, 0.96 mmol) in DMSO (5 mL) was treated with dimethylphosphite (0.2 mL, 2.2 mmol), DIPEA (0.7 mL, 3.8 mmol), 1,4-bis(diphenylphosphino)butane (0.041 g, 0.1 mmol), and Pd(OAc)₂ (0.022 g, 0.1 mmol) and stirred at 100° C. overnight. The reaction was poured on water and extracted with EtOAc (3x). The combined organic layers were washed with brine, dried over Na₂SO₄ and concentrated. Chromatography (0-100% EtOAc/hexanes) provided 24B as a light yellow solid (0.081 g, 15%).

In a manner similar to that found in Example 6, Step 5, 24B was deprotected to provide the title compound 24. LMCS m/z 308 (MH+).

Preparative Example 25

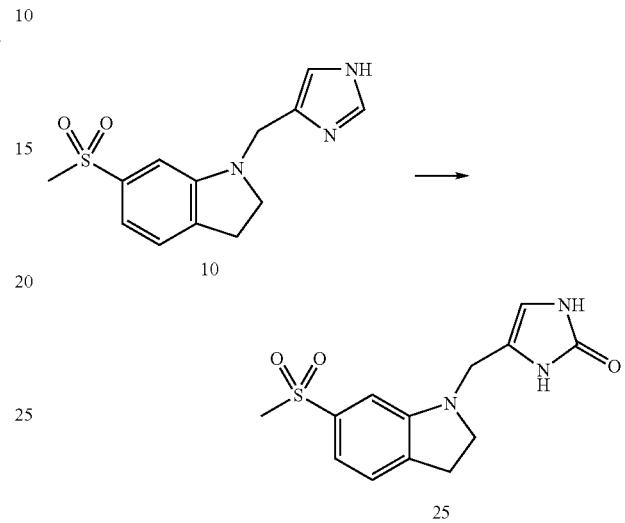

To a well-stirred mixture of Compound 10 (0.24 g, 0.87 mmol) in 1:1 THF-H₂O (10 mL) was added phenyl chloroformate (0.29 mL, 2.3 mmol) dropwise. The reaction was stirred at 20° C. for 4 h and then diluted with EtOAc. The organic layer was isolated, dried over Na₂SO₄ and concentrated. The resulting residue was dissolved in MeOH, treated with Et₃N (0.6 mL, 4.3 mmol), and stirred overnight. The solution was concentrated and subjected to chromatography (0-20% 1 N NH₃-MeOH/EtOAc) to provide the title compound 25 as a pale yellow solid (0.079 g, 87%). LMCS m/z 294 (MH+).

Preparative Example 26

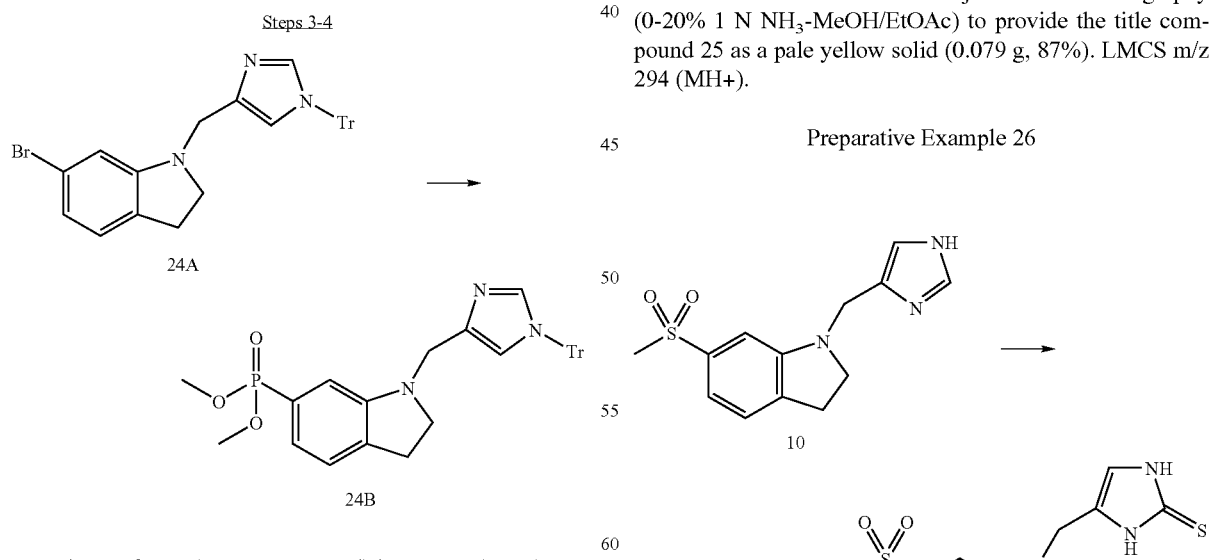

In a manner similar to that found in Example 25, 10 was treated with phenyl chlorothionoformate to give Compound 26. LMCS m/z 310 (MH+).

Preparative Example 27

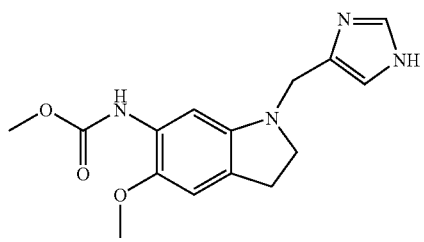

27

Step 1

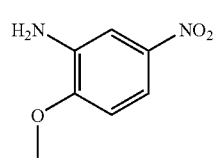

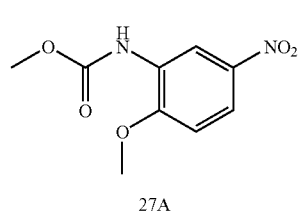

27A

A solution of 2-methoxy-5-nitroaniline (14.4 g, 85 mmol) in $CH_2Cl_2$ (100 mL) was treated with $ClCO_2Me$ (8.0 mL, 103 mmol) and $Et_3N$ (17.9 mL, 128 mmol), stirred overnight at 20° C., and concentrated. Chromatography (20-40% EtOAc/hexanes) provided 27A as a yellow solid (9.21 g, 48%).

Step 2

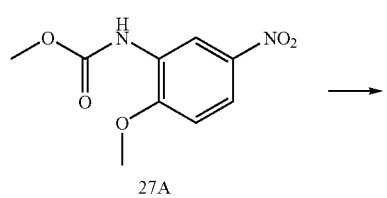

27A

27B

In a manner similar to that found in Example 6, Step 2, 27A was hydrogenated to provide 27B.

Step 3

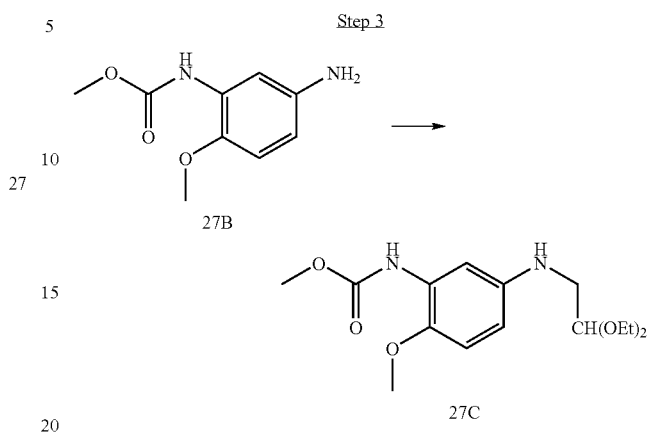

27B

27C

A solution of 27B (7.8 g, 40 mmol) in EtOH (100 mL) was treated with bromoacetaldehyde diethyl acetal (6.7 mL, 44 mmol) and $NaHCO_3$ (3.4 g, 40 mmol) and heated to reflux for 3d. The reaction was concentrated, taken up in $Et_2O$, and washed with water. The organic layer was dried over $Na_2SO_4$ and concentrated. Chromatography (0-40% EtOAc/hexanes) provided 27C (6.4 g, 51%).

Step 4

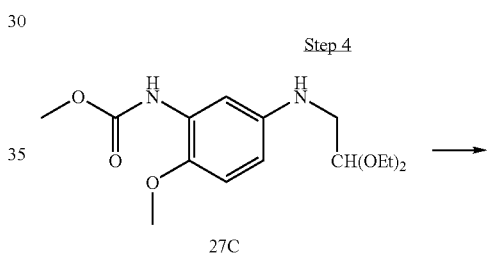

27C

27D

A solution of 27C (5.3 g, 17 mmol) in TFA (70 mL) was treated with trifluoroacetic anhydride (90 mL) and heated to reflux overnight. The reaction was concentrated and subjected to chromatography (0-40% EtOAc/hexanes) to provide 27D (2.9 g, 55%) as a pale yellow solid.

Steps 5-7

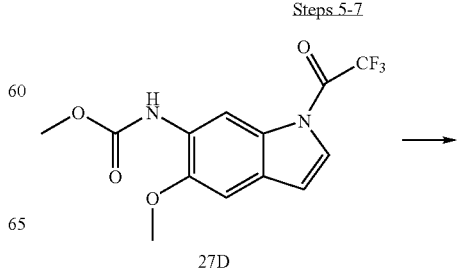

27D

-continued

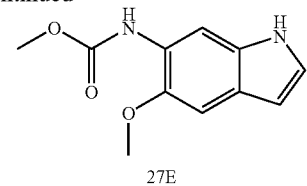
27E

A mixture of 27D (2.9 g, 9.2 mmol) in MeOH (20 mL) was treated with saturated aqueous $Na_2CO_3$ (5 mL) and heated at 55° C. for 1 d. The reaction was concentrated, extracted with $CH_2Cl_2$, dried over $Na_2SO_4$ and concentrated. Chromatography (20-40% EtOAc/hexanes) provided 27E (1.6 g, 78%).

In a manner similar to that found in Example 14, Step 2, and Example 4, Step 1, 27E was reduced with $NaCNBH_3$ and then converted to the title compound 27. LMCS m/z 303 (MH+).

Preparative Example 28

28

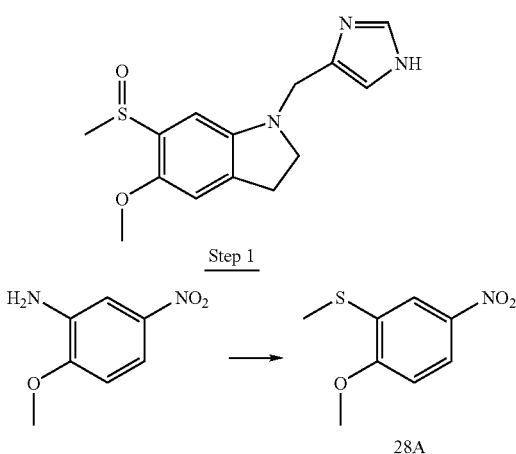

Step 1

A solution of 2-methoxy-5-nitroaniline (10.8 g, 64 mmol) and DMS (10.6 mL, 96 mmol) in $CH_3CN$ (100 mL) was treated slowly with isoamyl nitrite (10.3 mL, 77 mmol) and then heated at 45° C. for 1 h. The reaction was concentrated and subjected to chromatography (10% EtOAc/hexanes) to provide 28A (9.1 g, 71%).

Steps 2-4

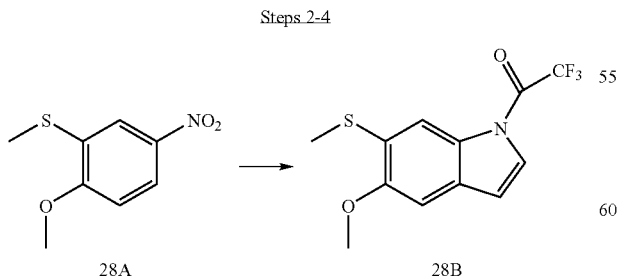
28A → 28B

In a manner similar to that found in Example 27, Steps 2-4, 28A was hydrogenated, alkylated and cyclized to provide 28B.

Steps 5-8

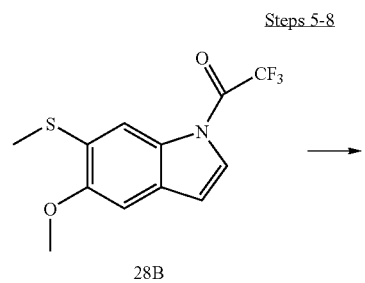
28B

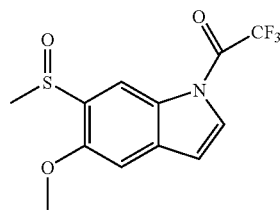
28C

A solution of 28B (3.16 g, 11 mmol) in $CH_2Cl_2$ (50 mL) was treated with urea-hydrogen peroxide (10.3 g, 109 mmol) and $K_2HPO_4$ (17.1 g, 98 mmol) and stirred 0.5 h. Trifluoroacetic anhydride (3.8 mL, 28 mmol) was then added slowly. The reaction mixture was stirred overnight at 20° C. and filtered through a celite pad. Chromatography (0-40% EtOAc/hexanes) provided 28C (1.5 g, 43%).

In a manner similar to that found in Example 27, Steps 5-7, 28C was deprotected, reduced, and then converted to title compound 28. LMCS m/z 292 (MH+).

Preparative Example 29

29

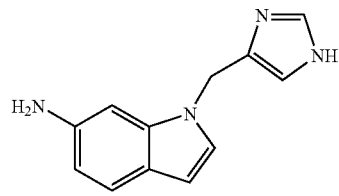

Step 1

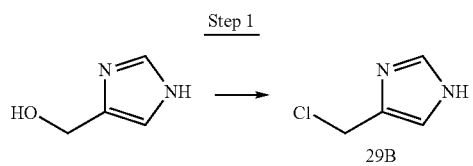
29B

A suspension of 4-hydroxymethylimidazole (15 g, 111 mmol) in toluene (100 mL) was treated slowly with a solution of $SOCl_2$ (8 mL, 144 mmol) in toluene (10 mL) via an addition funnel. The mixture was then refluxed for 1.5 h, cooled, and concentrated to provide 29B as a gray solid (15.8 g, 93%).

Preparative Example 31

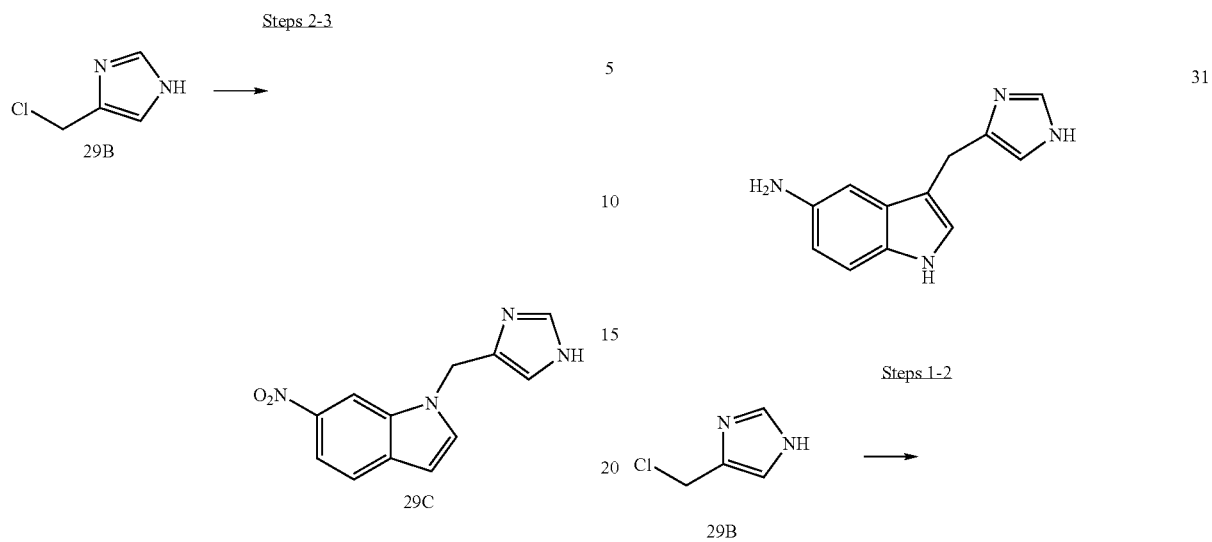

A mixture of 6-nitroindole (3.5 g, 21.8 mmol) in DMF was treated with 60% NaH (1.3 g, 32.7 mmol), stirred 30 min at 20° C., and treated with 29B (4.0 g, 26.2 mmol). The mixture was heated at 70° C. overnight, filtered through celite and concentrated. Chromatography (0-7% 1 N $NH_3$-MeOH/EtOAc) provided 29C as a yellow solid (1.7 g, 32%).

A solution of 29C (0.46 g, 1.9 mmol) in EtOH was treated with Raney nickel and hydrogenated (1 atm $H_2$) overnight. The mixture was filtered through celite, and concentrated to provide Compound 29 as a gray solid (0.39 g, 98%). LMCS m/z 213 (MH+).

Preparative Example 30

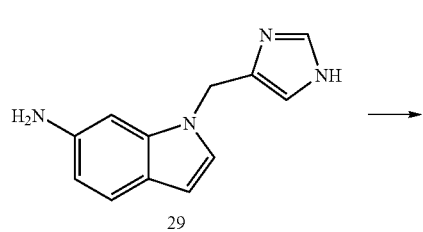

In a manner similar to that found in Example 27, Step 1, 29 was reacted with $ClCO_2Me$ to provide 30. LMCS m/z 271 (MH+).

A solution of 29B (6.9 g, 45.4 mmol) in DMF (100 mL) was treated with 5-nitroindole (14.7 g, 90.8 mmol) and KF (50% wt on celite, 15.8 g, 136 mmol) and heated at 90° C. overnight. The mixture was filtered through celite, and concentrated. Chromatography (0-10% 1 N $NH_3$-MeOH/EtOAc) provided 31A as a yellow solid (3.72 g, 34%).

In a manner similar to that found in Example 29, Step 3, 31A was hydrogenated to Compound 31. LMCS m/z 213 (MH+).

Preparative Example 32

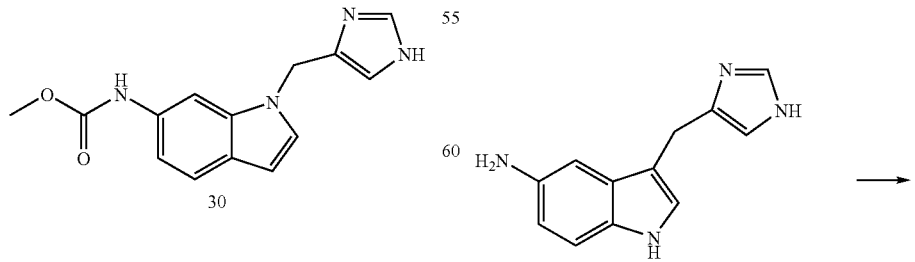

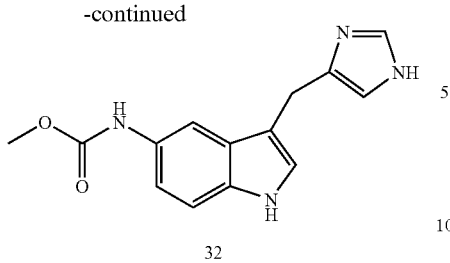

32

In a manner similar to that found in Example 27, Step 1, 31 was reacted with ClCO$_2$Me to provide 32. LMCS m/z 271 (MH+).

Preparative Example 33

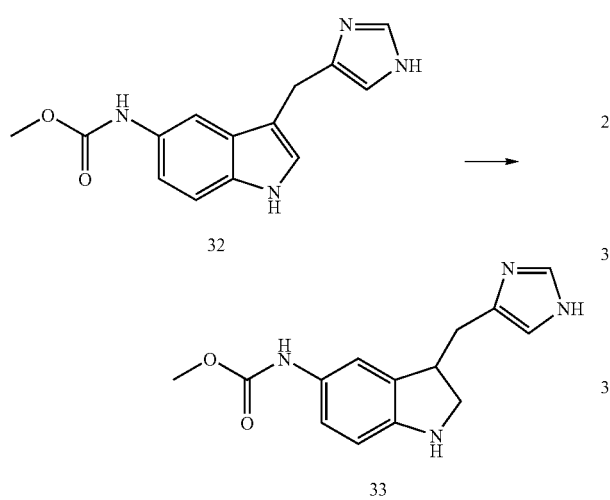

In a manner similar to that found in Example 14, Step 2, 32 was reduced with NaCNBH$_3$ to give 33. LMCS m/z 273 (MH+).

Preparative Example 34

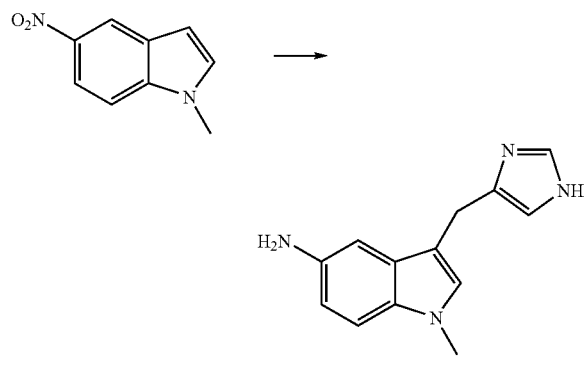

34

In a manner similar to that found in Example 31, Step 1 and Example 29, Step 3, N-methyl-5-nitroindole (Organic Process Research & Development 2001, 5, 604) was alkylated with 29B and hydrogenated to provide Compound 34. LMCS m/z 227 (MH+).

Preparative Example 35

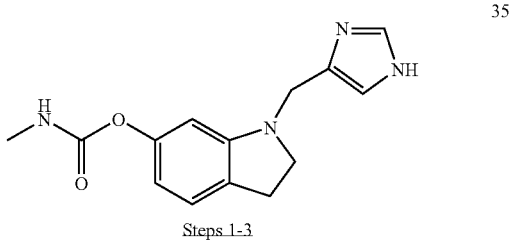

35

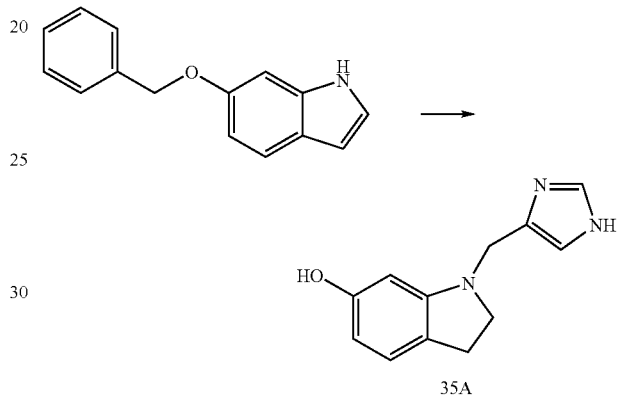

35A

In a manner similar to that found in Example 14 (Step 2), Example 4 (Step 1), and Example 6 (Step 2), 6-benzyloxyindole was reduced with NaCNBH$_3$, reacted with 4-imidazolecarboxaldehyde and hydrogenated to provide 35A.

Step 4

A solution of 35A (0.12 g, 0.46 mmol) and Et$_3$N (0.20 mL, 1.12 mmol) in dichloroethane (10 mL) was treated dropwise with MeNCO (0.035 g, 0.61 mmol) and refluxed for 2 h. The reaction was then stirred overnight at 20° C. and concentrated. The material was treated with water and extracted with CH$_2$Cl$_2$ (3×). The combined organic layers were then concentrated. The residue was taken up in Et$_2$NH (1.5 mL) and stirred overnight. The reaction was treated with water and extracted with CH$_2$Cl$_2$ (3×). The combined organic layers were then concentrated and subjected to chromatography (2-5% MeOH/CH$_2$Cl$_2$) to provide 35 as a white foam (0.015 g, 10%). LMCS m/z 273 (MH+).

Preparative Example 36

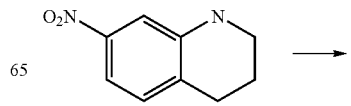

-continued

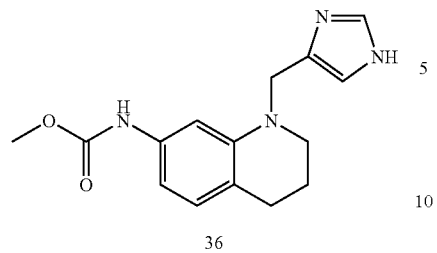

36

In a manner similar to that found in Example 4 (Step 1), Example 29 (Step 3), and Example 27 (Step 1), 7-nitro-1,2,3,4-tetrahydroquinoline (U.S. Pat. No. 5,283,336, 1994) was reacted with 4-imidazolecarboxaldehyde, hydrogenated, and then treated with ClCO$_2$Me to provide 36. LMCS m/z 287 (MH+).

Preparative Example 37

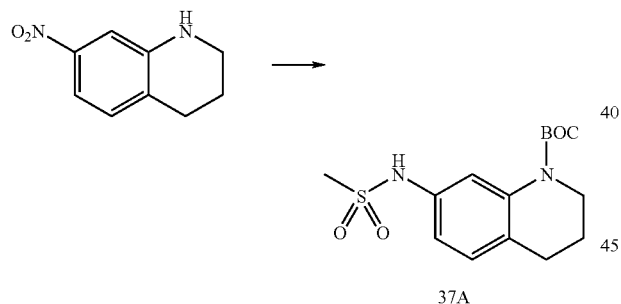

In a manner similar to that found in Example 1 (Step 1), Example 29 (Step 3), and Example 5 (Step 1), 7-nitro-1,2,3,4-tetrahydroquinoline (U.S. Pat. No. 5,283,336, 1994) was treated with (BOC)$_2$O/DMAP, hydrogenated, and then reacted with methanesulfonic anhydride/Et$_3$N to provide 37A.

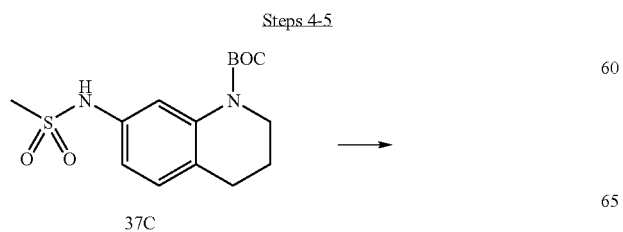

-continued

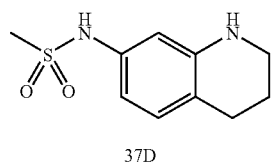

37D

A solution of 37C (0.49 g, 1.5 mmol) in CH$_2$Cl$_2$ (20 mL) was treated with 4 M HCl-dioxane (10 mL), stirred 1 h at 20° C., and concentrated. The mixture was dissolved in MeOH (10 mL), treated with dimethylaminomethyl-polystrene resin, and stirred at 20° C. for 1 h. The mixture was filtered and concentrated to provide 37D as a yellow gum (0.33 g, 97%). In a manner similar to that found in Example 4, Step 1, 37D was reacted with 4-imidazolecarboxyaldehyde to provide the title compound 37. LMCS m/z 307 (MH+).

Preparative Example 38

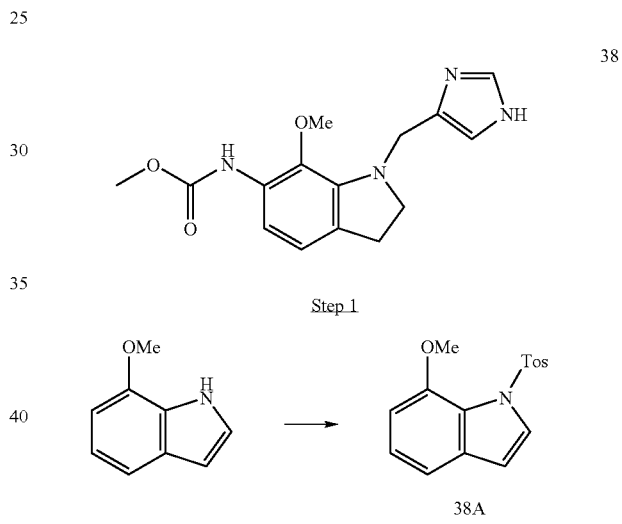

To a stirred solution of 7-methoxyindole (3 g, 20.4 mmol) in THF (80 mL) was added toluenesulfonyl chloride (4 g, 21 mmol) and NaH (60%, 1.22 g). The mixture was stirred at RT overnight, quenched with water, and concentrated under reduced pressure. The residue was partitioned between water (100 mL) and EtOAc (100 mL). The organic layer was then dried (Na$_2$SO$_4$), filtered and concentrated to provide 38A (1.5 g, 24%).

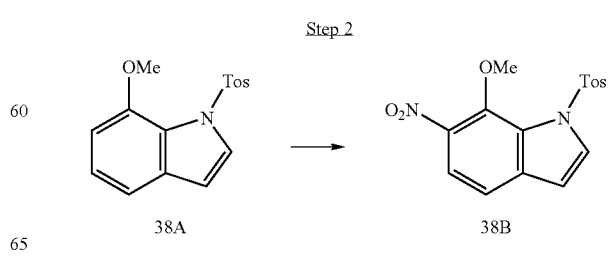

To a stirred solution of 38A in DCM (35 mL) was added HNO$_3$/SiO$_2$ (17 g, J. Org. Chem. 1993, 58, 1666). The mixture was sonicated for 10 minutes, and stirred at room temperature for 1.5 h. The reaction was filtered and concentrated. Column chromatography (10-40% EtOAc/Hexane) provided 38B (0.49 g, 29%).

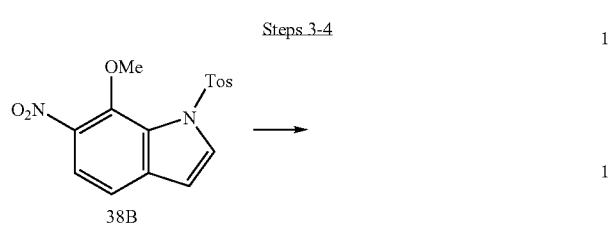

In a manner similar to that found in Example 1 (Step 2) and Example 15 (Step 3), 38B was hydrogenated and then reacted with ClCO$_2$Me to provide 38C.

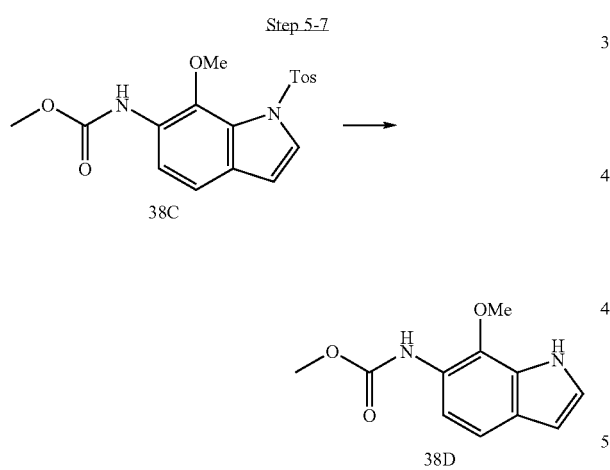

To a stirred solution of 38C (0.42 g, 1.14 mmol) in MeOH (14 mL) was added Mg powder (0.14 g, 5.7 mmol). The resulting suspension was sonicated for 20 minutes, and the reaction was monitored by TLC. After the disappearance of starting material, solvent was removed under reduced pressure. The residue was partitioned between DCM (50 mL) and 0.5 N HCl (40 mL). The organic phase was washed by NaHCO$_3$ (40 mL) and brine (40 mL), dried (MgSO$_4$), filtered and concentrated to provide 38D (0.23 g, 92%).

In a manner similar to that found in Example 14 (Step 2) and Example 4 (Step 1), 38D was reduced with NaCNBH$_3$/AcOH and treated with imidazole-4-carboxaldehyde to provide the title compound 38. MS m/z 303 (MH+).

Preparative Example 39

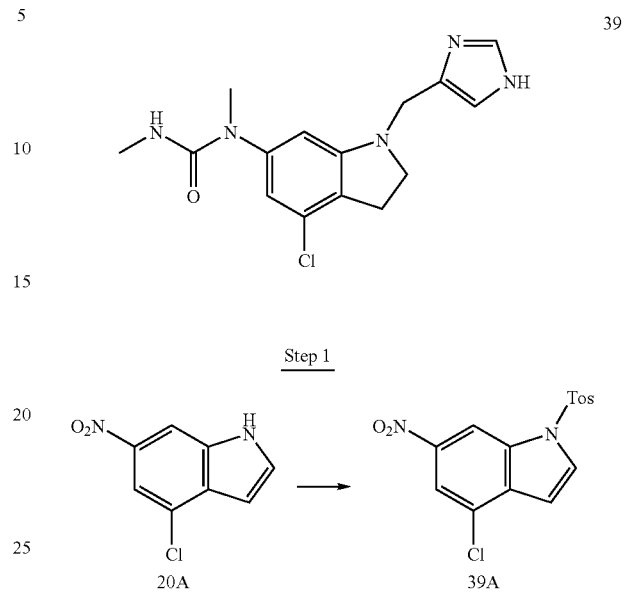

In a manner similar to that found in Example 38 (Step 1), 20A was treated with toluenesulfonyl chloride and NaH to provide compound 39A.

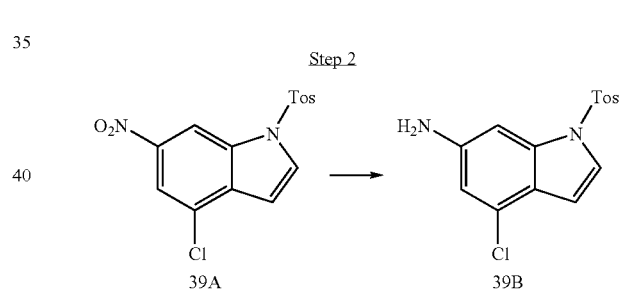

A solution of compound 39A (4.56 g, 13 mmol) in EtOH (260 mL) was treated with SnCl$_2$·2H$_2$O (11.7 g, 52 mmol). The reaction was refluxed at 90° C. for 3 h and then concentrated. The residue was diluted with sat. aq. NaHCO$_3$ (100 mL) and extracted with EtOAc (2×150 mL). The combined organic layer was dried (Na$_2$SO$_4$), filtered and evaporated to give a brown solid 39B.

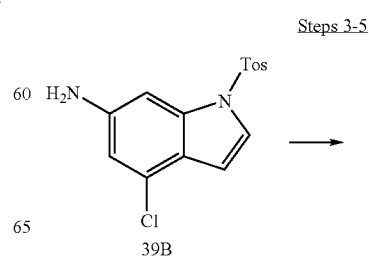

-continued

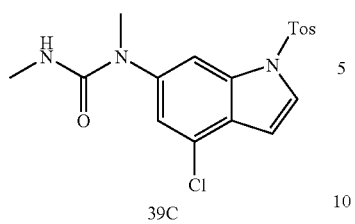
39C

In a manner similar to that found in Example 7 (Steps 1-3), 39B was treated with Ac$_2$O/HCO$_2$H, reduced with BH$_3$—SMe$_2$, and treated with MeNCO to yield compound 39C.

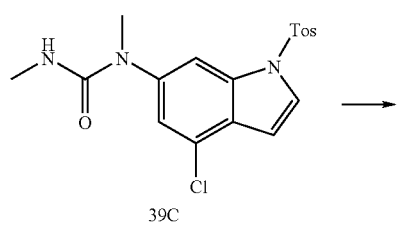
39C

Steps 6-8

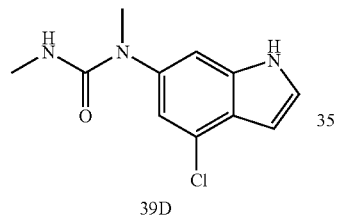
39D

A solution of 39C (2.7 g, 7.0 mmol) in MeOH (100 mL) was treated with KOH (5 g), stirred at RT for 1 h, and concentrated. The mixture was then treated with water and extracted with EtOAc (3×50 mL). The combined organic layer was dried (Na$_2$SO$_4$), filtered and evaporated to provide 39D.

In a manner similar to that previously described, 39D was reduced with NaBH$_3$CN (Example 14, Step 2, AcOH used as solvent) and then treated with 4-imadzolecarboxaldehyde (Example 4, Step 1) to give the title compound 39. MS m/z 320 (MH+).

Preparative Example 40

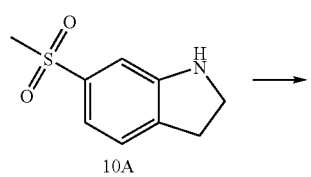
10A

-continued

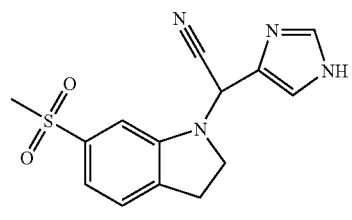
40

A mixture of 10A (0.25 g, 1.3 mmol) and imidazole-4-carboxaldehyde (1B, 0.16 g, 1.7 mmol) in CH$_2$Cl$_2$ (5 mL) was treated with Ti(OiPr)$_4$ (0.75 mL, 2.6 mmol), stirred at 20° C. overnight, and then treated with Et$_2$AlCN (2.6 mL, 1M/toluene). After 18 h, EtOAc, H$_2$O, and celite were added. Filtration and subsequent chromatography (0-10% of 7N NH$_3$-MeOH in CH$_2$Cl$_2$) provided 40 as a yellow solid (0.07 g, 18%). LCMS m/z 303 (MH+).

Preparative Example 41

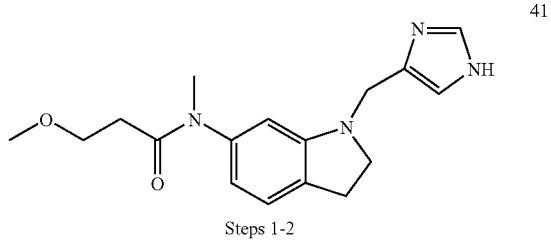
41

Steps 1-2

41A

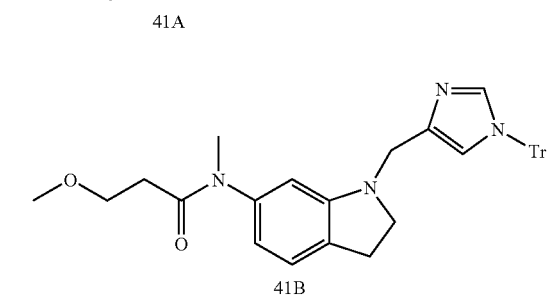
41B

A mixture of 3-methoxylpropionic acid (0.03 mL, 0.32 mmol) in DMF (4 mL) was treated with EDCI (61 mg, 0.32 mmol) and HOBt (43 mg, 0.32 mmol). After stirring for 10 min, compound 41A (100 mg, 0.21 mmol, see Example 6, Step 4) was added. The reaction was stirred at RT overnight, diluted with NaHCO$_3$ (50 mL), and extracted with CH$_2$Cl$_2$ (3×50 mL). The combined organic layer was washed with H$_2$O (2×60 mL), dried over Na$_2$SO$_4$ and concentrated to provide 41B.

In a manner similar to that found in Example 6 (Step 5), 41B was treated with TFA and Et₃SiH to provide the title compound 41. LCMS m/z 315 (MH+).

Preparative Example 42

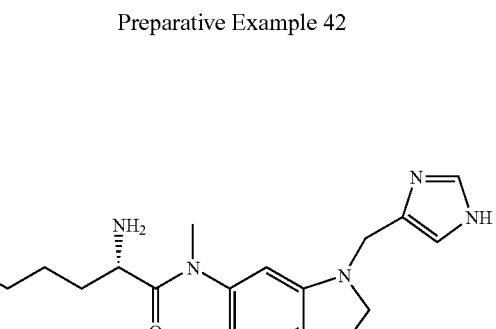

In a manner similar to that found in Example 41, 42A (Boc-Nle-OH) was coupled with 41A to afford 42B Global deprotection (TFA/Et₃SiH) and chromatography (reverse-phase HPLC, 0-15% gradient of 0.25% NH₃-MeOH/H₂O and 0.25% NH₃-MeOH/acetonitrile) provided the title compound 42. LCMS m/z 342 (MH+).

Preparative Example 43

In a manner similar to that found in Example 7, 7B was sequentially treated with acetoxyacetyl chloride, TFA, and then 4-imidazolecarboxaldehyde to provide 43A. MS m/z 329 (MH+).

Step 4

A mixture of the ester 43A (180 mg, 0.55 mmol) in methanol (20 mL) was treated with LiOH (200 mg), stirred for 1 h at 25° C., and then concentrated. Chromatography (DCM containing 5% of 7N NH₃/MeOH) provided the title compound 43 (80 mg, 51%). MS m/z 287 (MH+).

Preparative Example 44

In a manner similar to that found in Example 7, 1A was acylated with acetic anhydride/pyridine and then reduced with BH₃—SMe₂ to provide 44A.

Steps 3-5

In a manner similar to that found in Example 7, 44A was treated with ClCO₂Me/pyridine and then converted to the title compound 44. MS m/z 301 (MH+).

Preparative Example 45

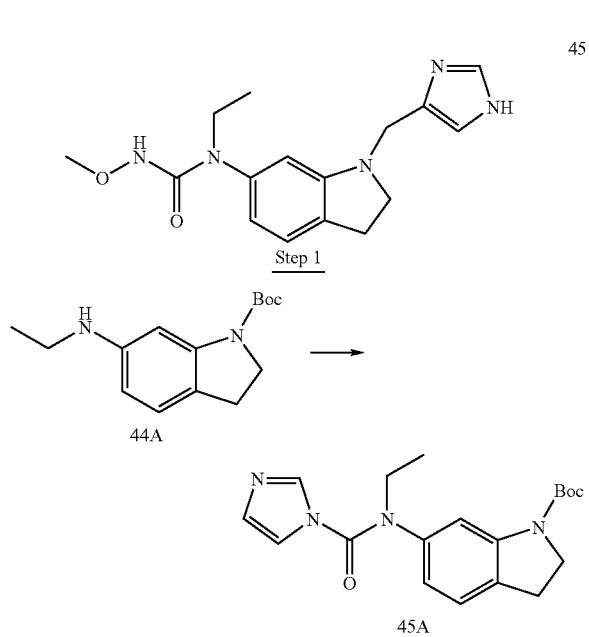

A mixture of 44A (100 mg, 0.38 mmol), Et₃N (0.11 mL, 0.76 mmol) and carbonyldiimidazole (92 mg, 0.38 mmol) in DCM (5 mL) was stirred overnight. Additional Et₃N (0.2 mL, 1.43 mmol) and carbonyldiimidazole (0.2 g, 1.2 mmol) was then added. After 18 h, the reaction was concentrated and chromatographed (50-80% EtOAc/hexanes) to give 45A (155 mg).

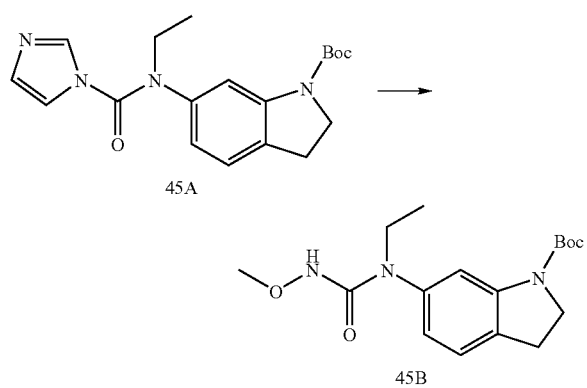

Compound 45A was mixed with CH₃CN (5 mL) and MeI (3 mL, 48 mmol) in a sealed tube and heated at 55° C. for 3 h. Solvent was removed and the residue was dried under high vacuum for 0.5 h. THF (5 mL), MeONH₂—HCl (95 mg, 1.14 mmol) and DIPEA (0.2 mL, 1.14 mmol) were sequentially added. The reaction was stirred for 2 d, concentrated, and then partitioned between water and DCM. The organic layer was dried (Na₂SO₄), filtered and evaporated. Chromatography (50-60% EtOAc/hexanes) gave 45B (100 mg).

In a manner similar to that found in Example 1 (Step 4) and Example 4, (Step 1), compound 45B was deprotected and converted to the title compound 45. MS m/z 316 (MH+).

Preparative Example 46

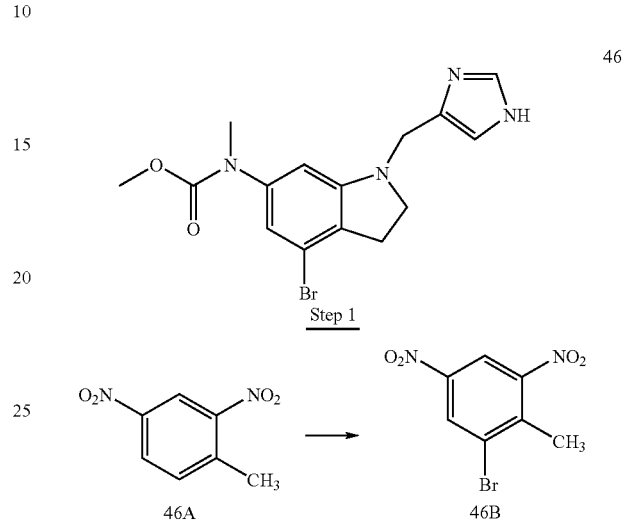

A 1 L 3-neck round-bottom flask equipped with a condenser and a thermometer was charged with 2,4-dinitrotoluene (46A, 20 g, 0.11 mol), concentrated sulfuric acid (50 mL), water (50 mL) and pre-made K₂SO₄ (KOH+conc. H₂SO₄, equivalent to 100 mg of K₂SO₄). The mixture was heated to 80° C. to 90° C. and treated with NaBrO₃ (17.24 g, 0.114 mol) in portions, while maintaining a temperature of 80° C. to 90° C. The mixture was then stirred at 85° C. overnight, cooled to RT and extracted with EtOAc (3×200 mL). The combined organic layers were washed with sat. aq. NaHCO₃ and brine solution. The organic layer was dried (MgSO₄), filtered and concentrated under reduced pressure. The residue was purified by flash column chromatography (2-5% EtOAc/hexanes) to give 46B (8.02 g, 28%).

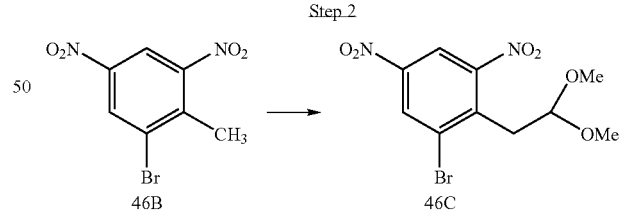

To compound 46B (13.86 g, 53.3 mmol) was added N,N-dimethylformamide dimethyl acetal (79.5 mL, 533 mmol). The reaction was heated to reflux at 115° C. The mixture then was cooled and concentrated. The crude product was dissolved in MeOH (250 mL), treated with HCl (10.5 mL), and refluxed for 4 h. The reaction was cooled to RT, diluted with water and extracted with EtOAc (3×100 mL). The combined organic layers were dried (MgSO₄), filtered and concentrated under reduced pressure. The residue was purified by flash column chromatography (2.5-8% EtOAc/hexanes) to give compound 46C (14.67 g, 82%).

Step 3

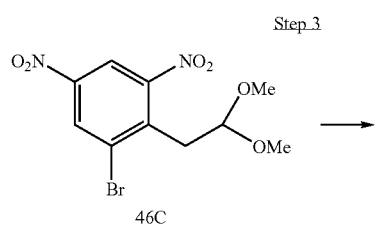

To a solution of 46C (4.04 g, 12.1 mmol) in glacial AcOH (40 mL) at 60° C. was added iron powder (2.03 g, 36.3 mmol). The reaction was heated to 110° C. and stirred for 40 min. Then the mixture was cooled and poured into cold water and the precipitate was filtered. The filtrate was extracted with EtOAc (3×50 mL). The combined organic layers were dried (MgSO$_4$), filtered and concentrated under reduced pressure. The residue was purified by flash column chromatography (5-15% EtOAc/hexanes) to give 46D (0.93 g, 32%).

Steps 4–5

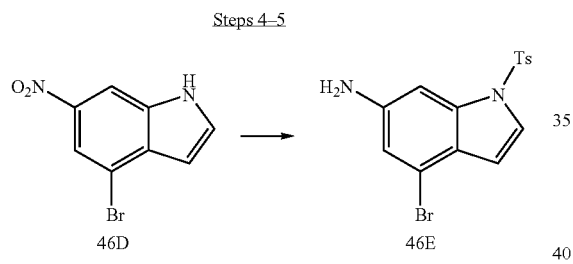

In a manner similar to that described in previous examples, 46D was protected with TsCl (Example 38, Step 1) and reduced with SnCl$_2$-2H$_2$O (Example 39, Step 2) to provide 46E.

Steps 6–11

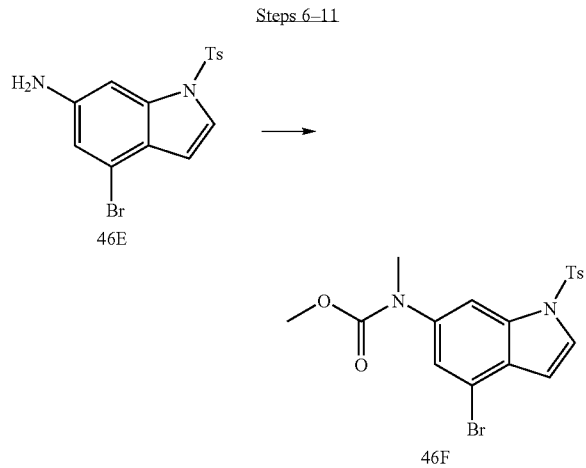

In a manner similar to that described in Example 7, 46E was treated with Ac$_2$O/HCO$_2$H, reduced with BH$_3$, and treated with ClCO$_2$Me/pyridine to provide 46F.

Compound 46F was then deprotected with Mg (Example 38, Step 5), reduced with NaBH$_3$CN (Example 14, Step 2, AcOH used as solvent), and treated with 4-imidazolecarboxaldehyde (Example 4, Step 1) to provide 46. MS m/z 365 (MH+).

Preparative Example 47

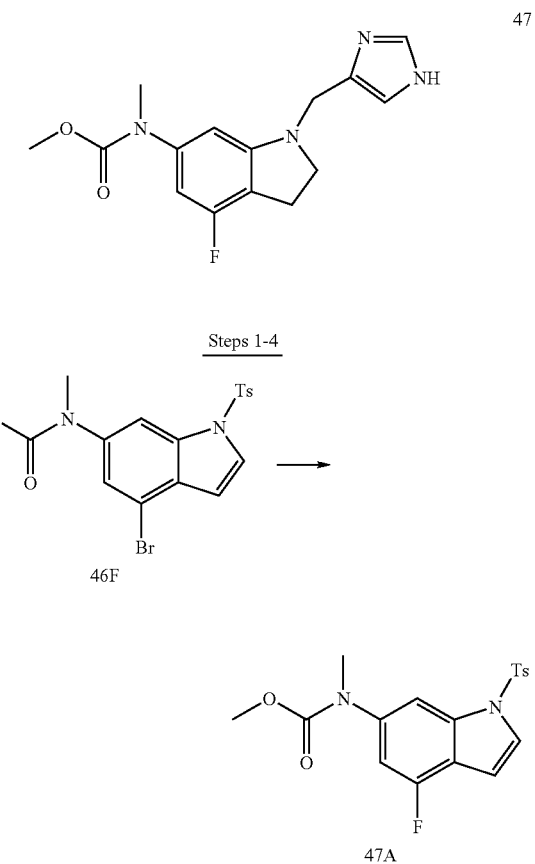

A mixture of 46F (121 mg, 0.28 mmol) in anhydrous THF at −78° C. under argon was treated with n-BuLi (1.6 M in hexanes, 0.17 mL, 0.28 mmol) dropwise, stirred at −78° C. for 8 min and then treated with N-fluorobenzenesulfonimide (87 mg, 0.28 mmol, solution in THF, added via cannula). The mixture was allowed to warm to 0° C. over 2 h, quenched with water, and extracted with EtOAc (3×10 mL). The combined organic layer was dried (MgSO$_4$), filtered and concentrated. The residue was purified by flash column chromatography (0-25% EtOAc/hexanes) to give compound 47A (62 mg, 59%).

In a manner similar to that found in previous examples, 47A was deprotected with KOH (Example 39, Step 6), reduced with NaBH$_3$CN (Example 14, Step 2, AcOH used as solvent), and treated with 4-imidazolecarboxaldehyde (Example 4, Step 1) to give compound 47. MS m/z 305 (MH+).

Preparative Example 48

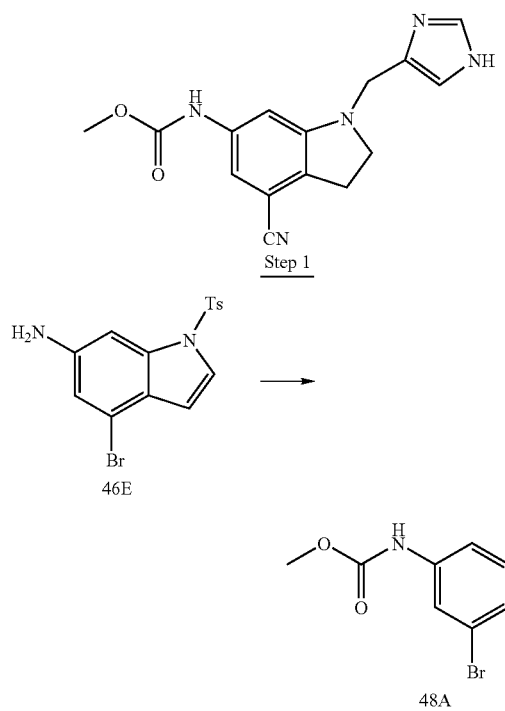

In a manner similar to that found in Example 7, compound 46E was treated with ClCO₂Me/DIPEA to provide 48A.

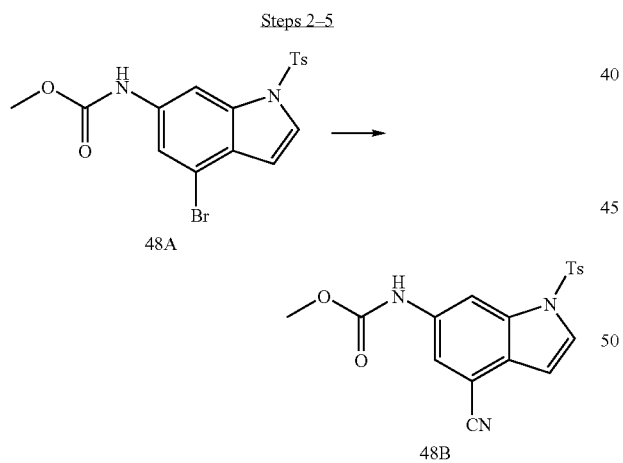

A mixture of intermediate 48A (500 mg, 1.2 mmol), Zn(CN)₂ (160 mg, 1.3 mmol), 1,1'-bis(diphenylphosphino)ferrocene (275 mg, 0.3 mmol), and Pd₂dba₃ (55 mg, 0.1 mmol) was stirred in DMF (100 mL) at 25° C. under a N₂ atmosphere and then heated at 120° C. for 12 h. The suspension was cooled to RT and concentrated. The residue was partitioned between EtOAc (3×100 mL) and sat. aq. NH₄Cl (50 mL). The combined organic phase was dried over Na₂SO₄ and concentrated. Column chromatography (DCM) provided 48B (415 mg, 94%).

In a manner similar to that previously described, 48B was deprotected with KOH (Example 39, Step 6), reduced with NaBH₃CN (Example 14, Step 2, AcOH used as solvent) and treated with 4-imidazolecarboxaldehyde (Example 4, Step 1) to give the title compound 48. MS m/z 298.4 (MH+).

Preparative Example 49

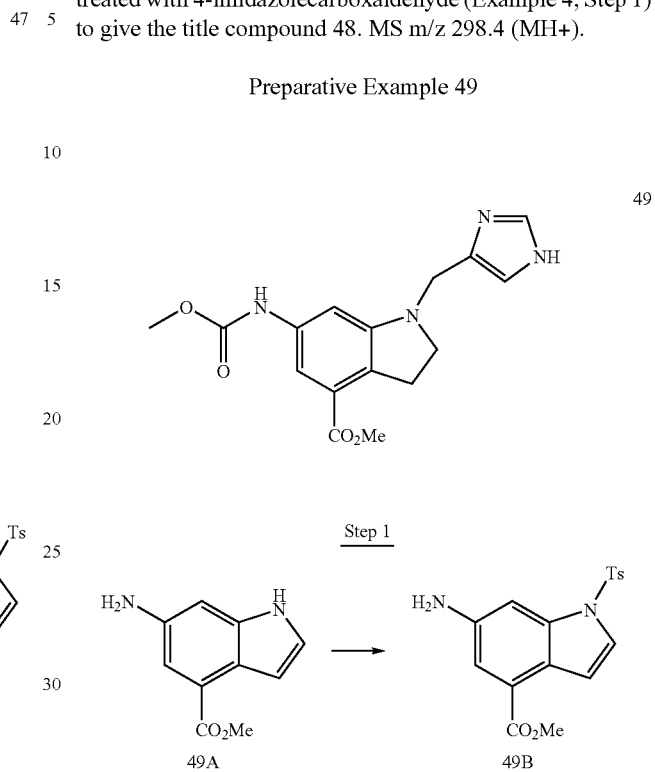

A stirred solution of methyl 6-aminoindole-4-carboxylate (49A, 0.5 g, 2.63 mmol) in THF (10 mL) under Ar at 0° C. was treated sequentially with NaH (0.095 g, 3.95 mmol, added portionwise) and TsCl (0.551 g, 3.16 mmol, added portionwise) and then allowed to warm to RT. After 2 h, the reaction was quenched with MeOH (3.95 mmol) at 0° C., poured onto ice cold water (10 mL) and extracted with EtOAc. The organic layer was washed with brine, dried over (Na₂SO₄), filtered and concentrated. Chromatography (40% EtOAc/hexanes) afforded 49B (0.51 g, 57%).

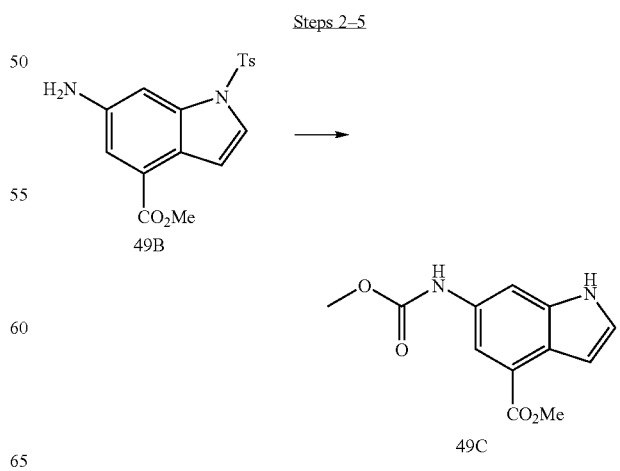

In a manner similar to that found in Example 7, compound 49B was treated with ClCO$_2$Me/pyridine. The product (0.45 g, 1.12 mmol) was taken up in DMF (5 mL) and treated with LiOH (0.110 g, 4.48 mmol). After 10 min, thioglycolic acid (0.124 g, 1.34 mmol) was added. The resulting solution was stirred at RT for 48 h, diluted with EtOAc and washed with water. After extracting the water layer with EtOAc, the combined organic layers were washed with sat. aq. Na$_2$CO$_3$ (2×), dried over sodium sulfate, filtered and evaporated. Chromatography (50% EtOAc/hexanes) afforded 49C (0.15 g, 54%).

In a manner similar to that previously described, 49C was reduced with NaBH$_3$CN (Example 14, Step 2, AcOH used solvent) and treated with 4-imidazolecarboxaldehyde (Example 4, Step 1) to give compound 49. MS m/z 331 (MH+).

Preparative Example 50

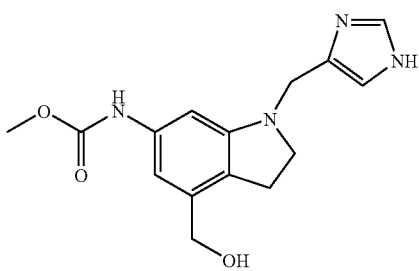

50

-continued
Step 1

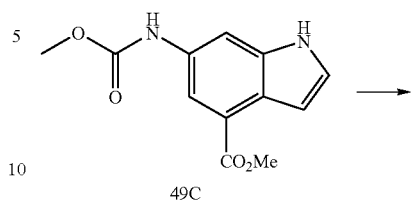
49C

50A

In a manner similar to that found in Example 14 (Step 2), compound 49C reduced with NaBH$_3$CN. A solution of the product (0.060 g, 0.24 mmol) in THF was treated with LAH (0.027 g, 0.72 mmol) at 0° C. under Ar. After 2 h at RT, the reaction was quenched with saturated Na$_2$SO$_4$ and filtered. The precipitate was washed with ethyl acetate (50 mL). The organic layer was washed with brine and concentrated. Chromatography (2% 7N NH$_3$-MeOH in DCM) gave 50A (0.030 g, 57%).

In a manner as described in Example 4 (Step 1), 50A was converted to the title compound 50. MS m/z 303 (MH+).

The following compounds were prepared following essentially the same procedures as in the examples above.

| Cpd | Structure | MS (MH+) |
|---|---|---|
| 100 | 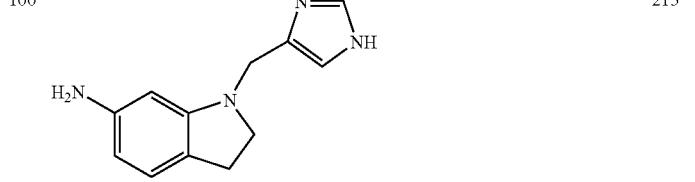 | 215 |
| 101 | 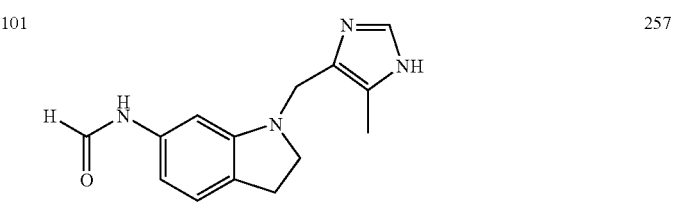 | 257 |

-continued
| Cpd | Structure | MS (MH+) |
|---|---|---|
| 102 | 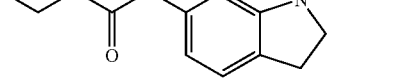 | 286 |
| 103 | 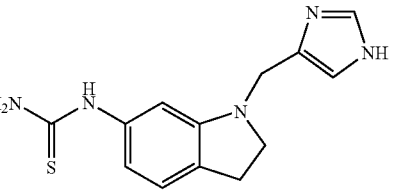 | 274 |
| 104 | 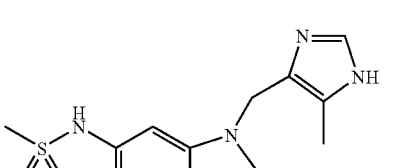 | 307 |
| 105 | 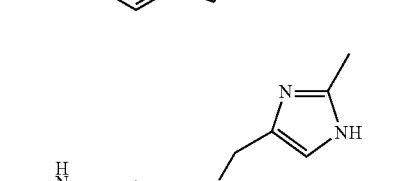 | 307 |
| 106 | 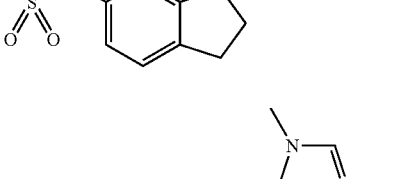 | 307 |
| 107 | 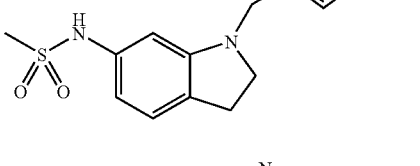 | 292 |
| 108 | 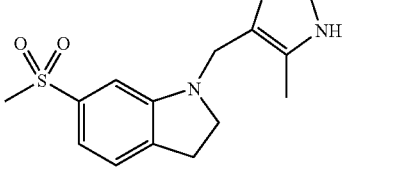 | 292 |

-continued

| Cpd | Structure | MS (MH+) |
|---|---|---|
| 109 | 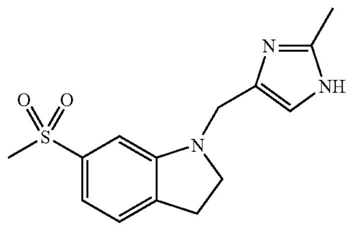 | 292 |
| 110 | 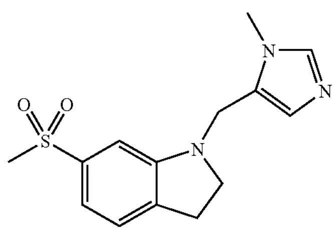 | 292 |
| 111 | 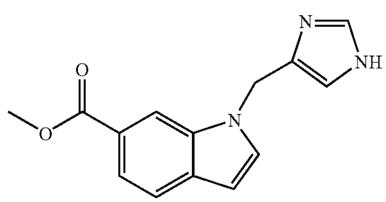 | 256 |
| 112 | 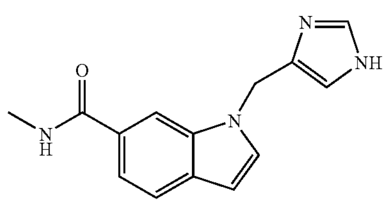 | 255 |
| 113 | 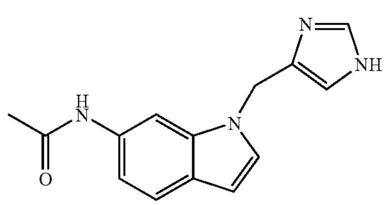 | 255 |
| 114 | 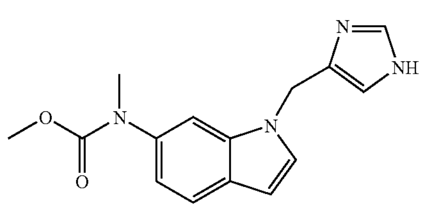 | 285 |
| 115 | 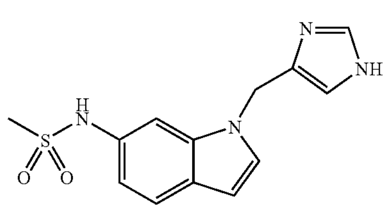 | 291 |

-continued

| Cpd | Structure | MS (MH+) |
|---|---|---|
| 116 | 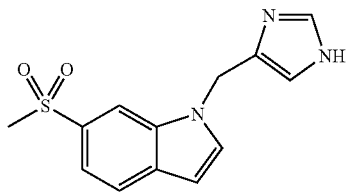 | 276 |
| 117 | 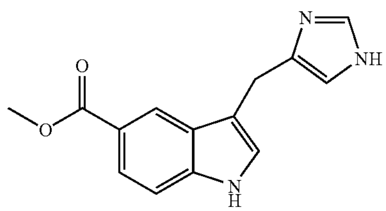 | 256 |
| 118 | 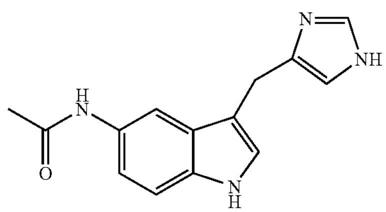 | 255 |
| 119 | 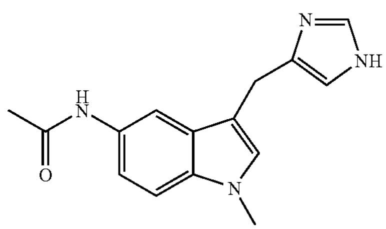 | 269 |
| 120 | 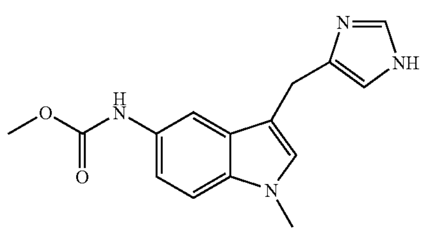 | 285 |
| 121 | 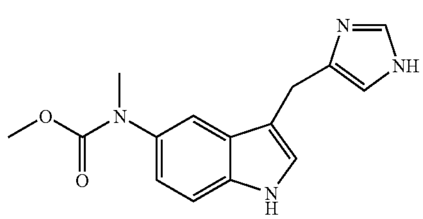 | 285 |
| 122 | 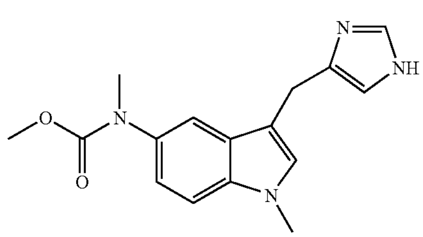 | 299 |

-continued

| Cpd | Structure | MS (MH+) |
|---|---|---|
| 123 | 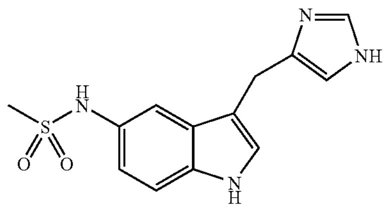 | 291 |
| 124 | 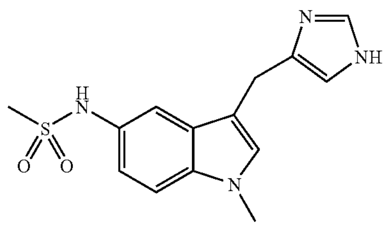 | 305 |
| 125 | 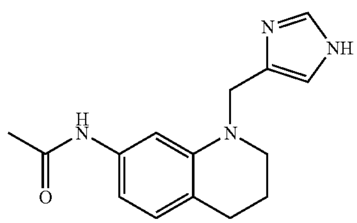 | 271 |
| 126 | 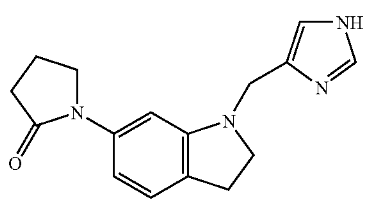 | 283 |
| 127 | | 258 |
| 127 | | 321 |
| 128 | 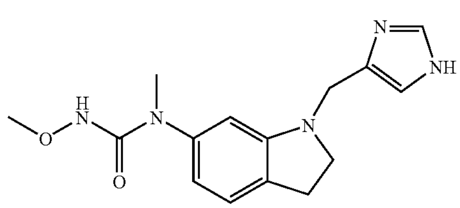 | 302 |

-continued

| Cpd | Structure | MS (MH+) |
|---|---|---|
| 129 | 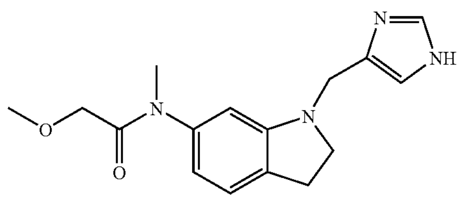 | 301 |
| 130 | 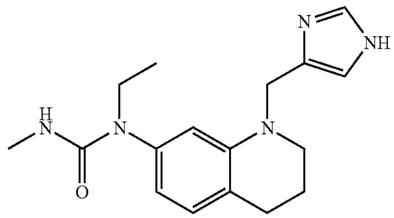 | 314 |
| 131 | 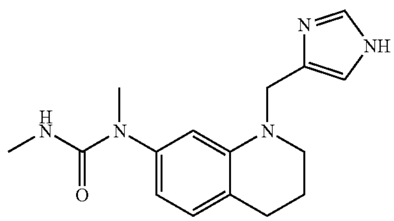 | 300 |
| 132 | 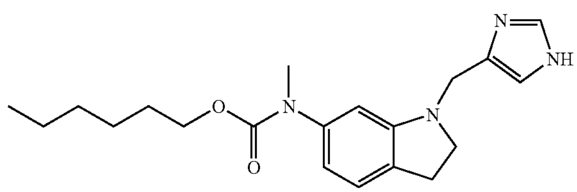 | 357 |
| 133 | 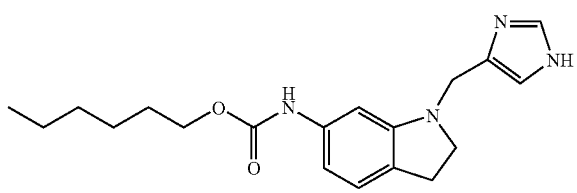 | 343 |
| 134 | 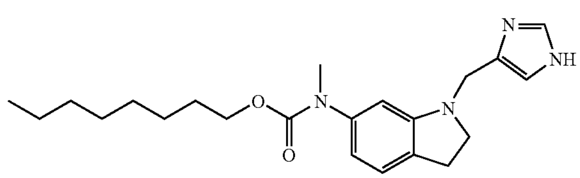 | 385 |
| 135 | 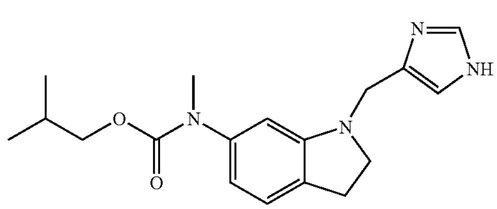 | 329 |

-continued

| Cpd | Structure | MS (MH+) |
|---|---|---|
| 136 | 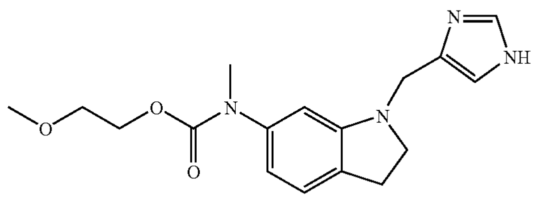 | 331 |
| 137 | 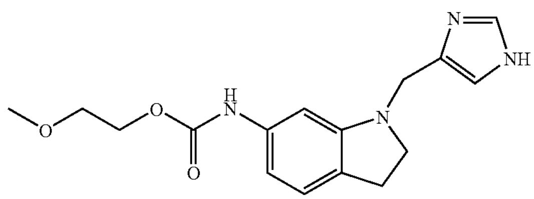 | 317 |
| 138 | 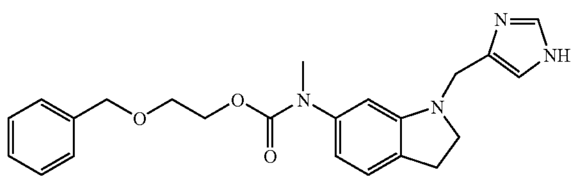 | 407 |
| 139 | 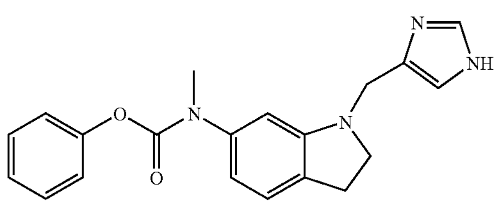 | 349 |
| 140 | 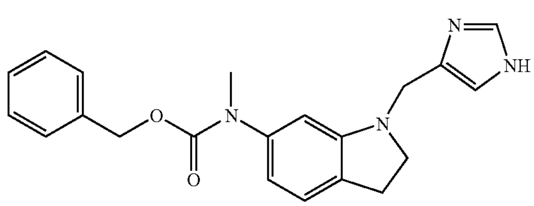 | 363 |
| 141 | 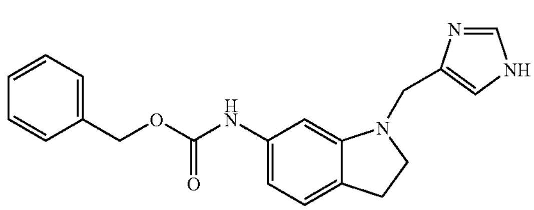 | 349 |
| 142 | 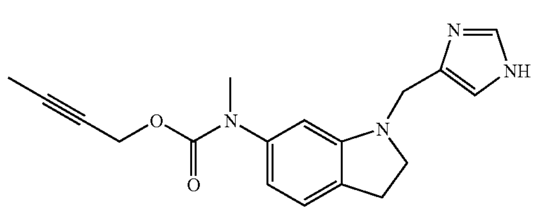 | 325 |

-continued
| Cpd | Structure | MS (MH+) |
|---|---|---|
| 143 | 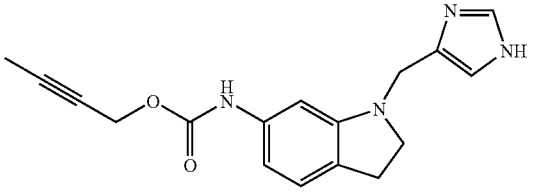 | 311 |
| 144 | 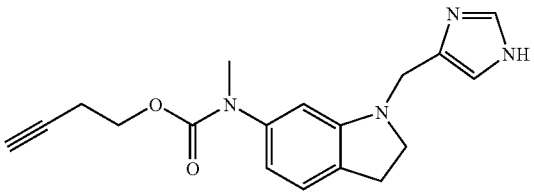 | 325 |
| 145 | 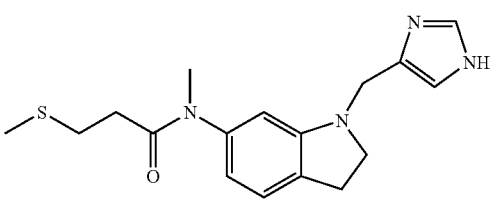 | 331 |
| 146 | 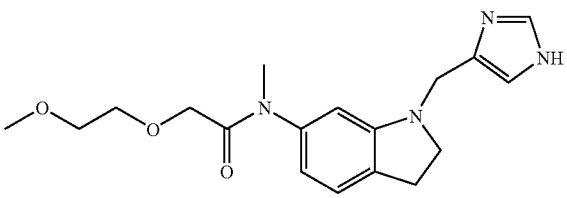 | 345 |
| 147 | 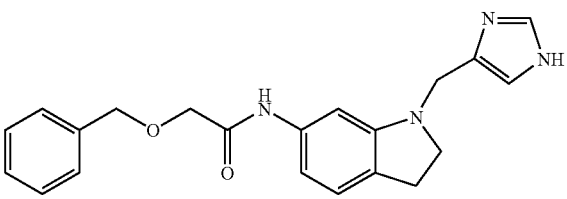 | 363 |
| 148 | 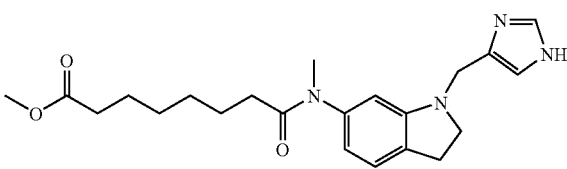 | 399 |
| 149 | 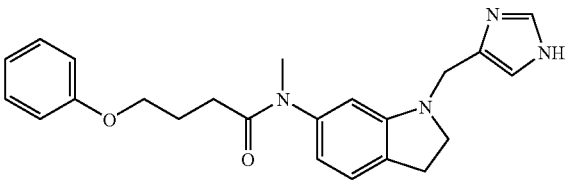 | 391 |

-continued

| Cpd | Structure | MS (MH+) |
|---|---|---|
| 150 | 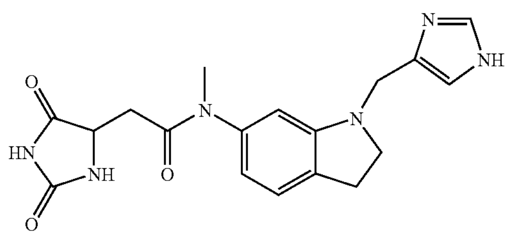 | 369 |
| 151 | 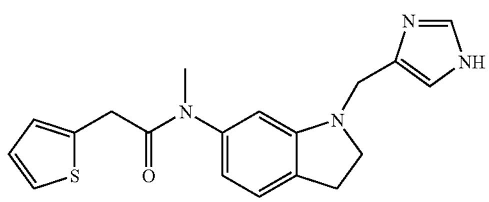 | 353 |
| 152 | 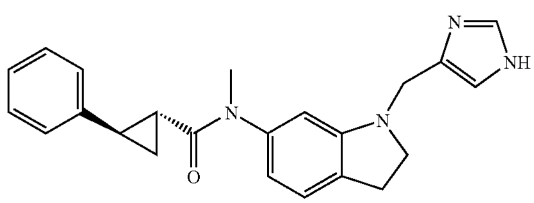 | 373 |
| 153 | 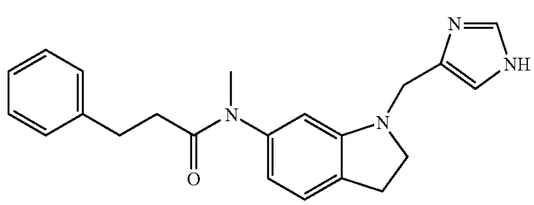 | 361 |
| 154 | 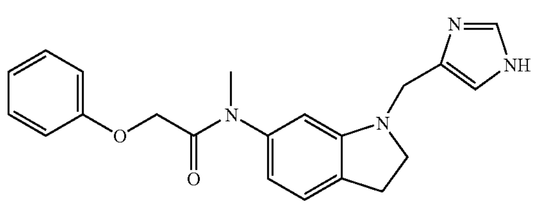 | 363 |
| 155 | 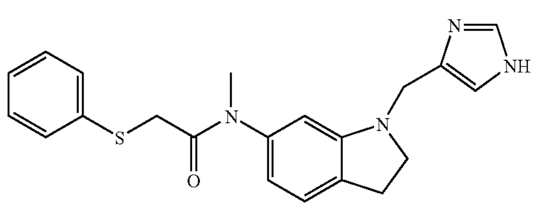 | 379 |
| 156 | 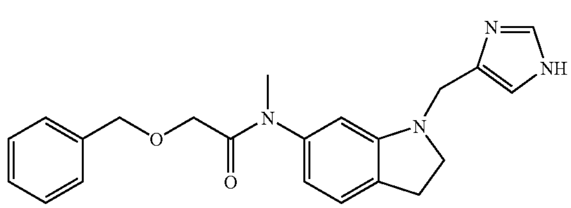 | 377 |

-continued
| Cpd | Structure | MS (MH+) |
|---|---|---|
| 157 | 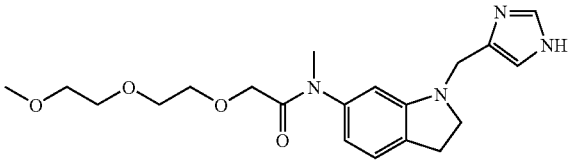 | 389 |
| 158 | 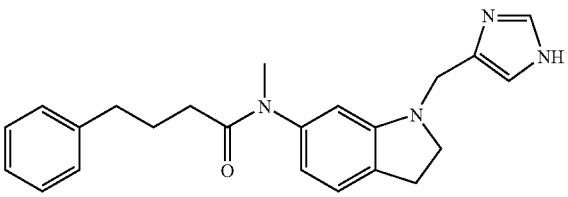 | 375 |
| 159 | 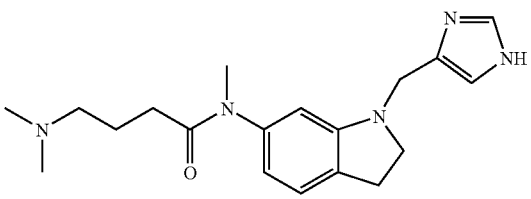 | 342 |
| 160 | 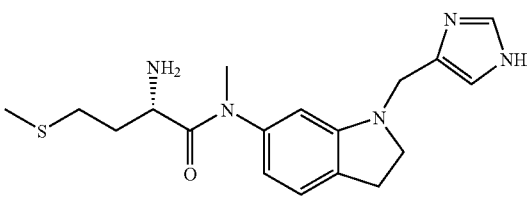 | 360 |
| 161 | 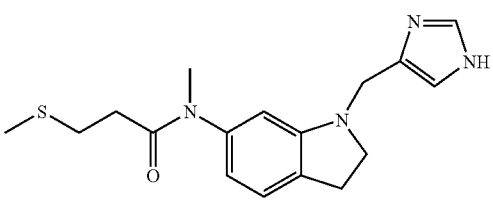 | 317 |
| 162 | 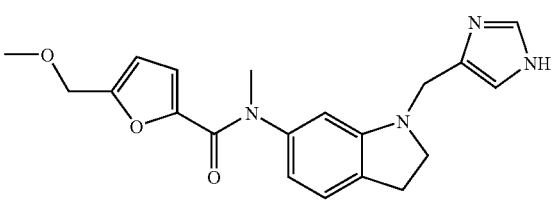 | 367 |
| 163 | 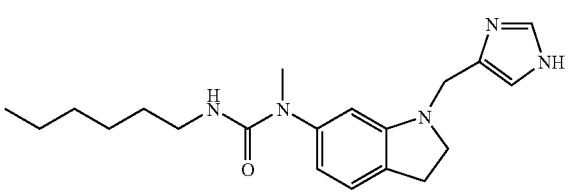 | 356 |

-continued
| Cpd | Structure | MS (MH+) |
|---|---|---|
| 164 | 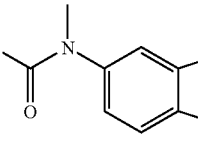 | 362 |
| 165 | 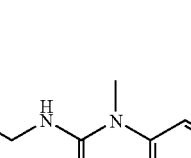 | 390 |
| 166 | 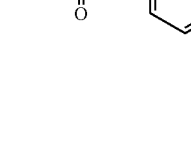 | 371 |
| 167 | 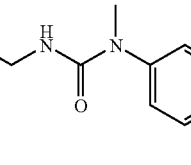 | 795036 |
| 168 | 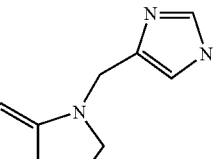 | 307 |
| 169 | 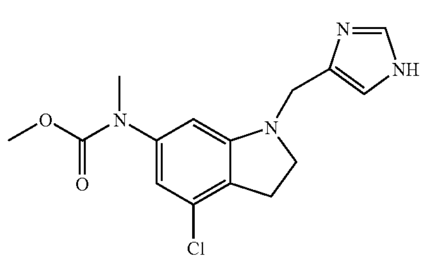 | 321 |

-continued

| Cpd | Structure | MS (MH+) |
|---|---|---|
| 170 | 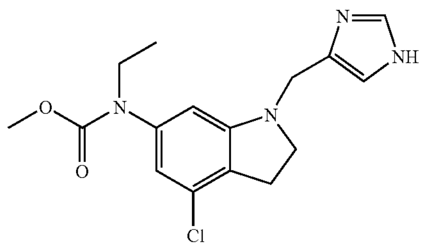 | 335 |
| 171 | 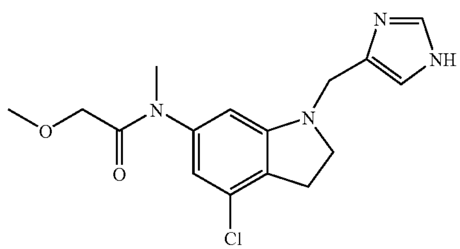 | 335 |
| 172 | 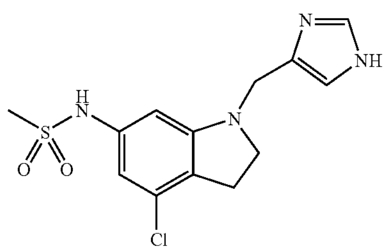 | 327 |
| 173 | 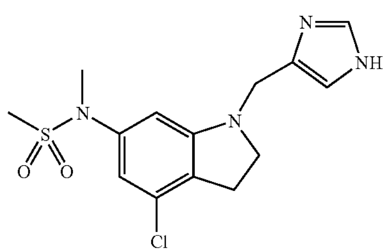 | 341 |
| 174 | 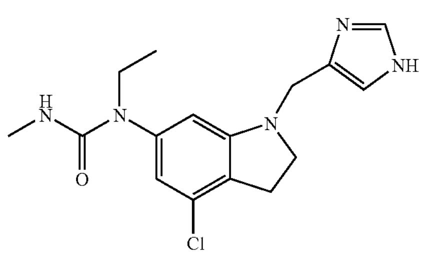 | 334 |
| 175 | 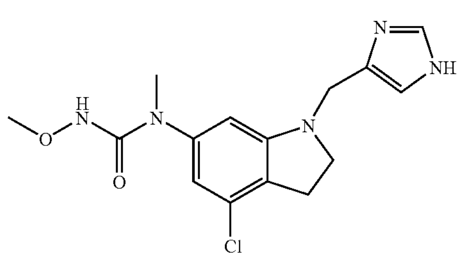 | 336 |

-continued

| Cpd | Structure | MS (MH+) |
|---|---|---|
| 176 | 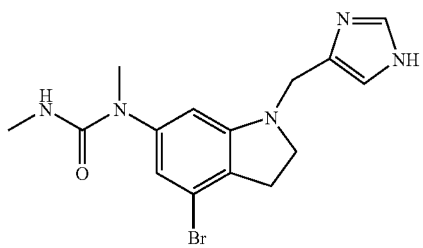 | 364 |
| 177 | 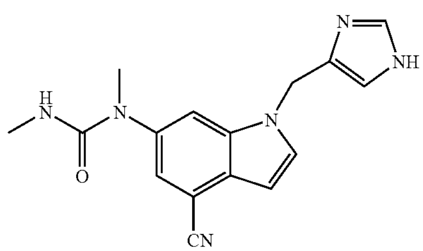 | 309 |
| 178 | 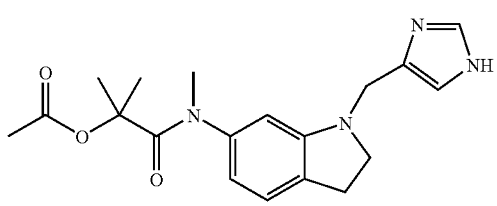 | 357 |
| 179 | 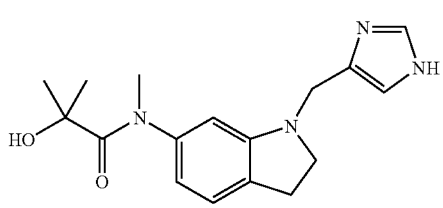 | 315 |
| 180 | 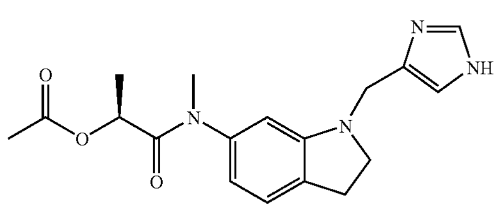 | 343 |
| 181 | 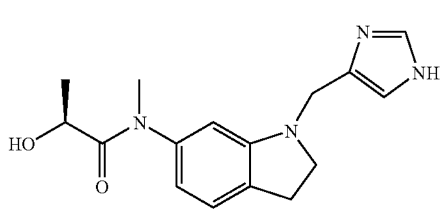 | 301 |
| 182 | 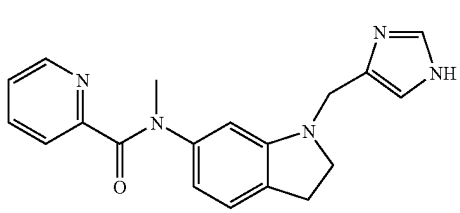 | 334 |

-continued

| Cpd | Structure | MS (MH+) |
|---|---|---|
| 183 | 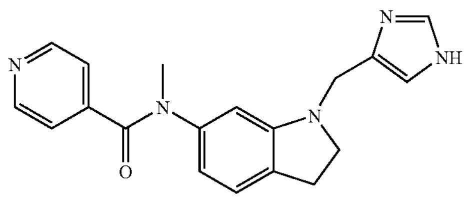 | 334 |
| 184 | 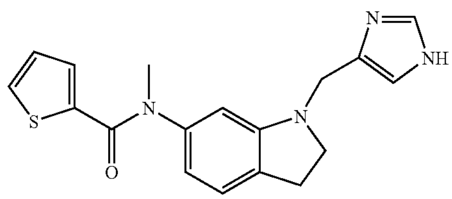 | 339 |
| 185 | 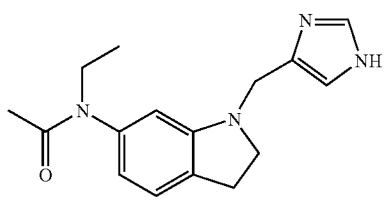 | 285 |
| 186 | 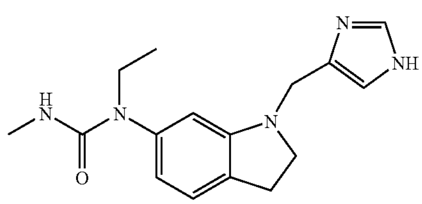 | 300 |
| 187 | 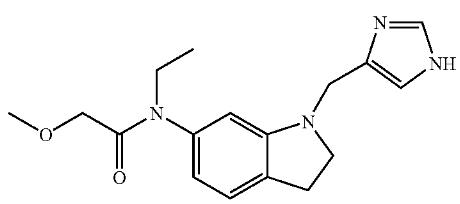 | 315 |
| 188 | 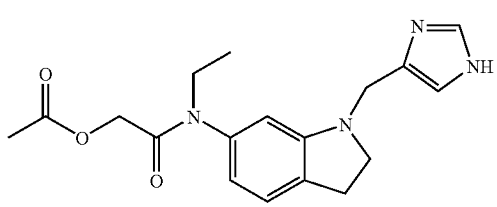 | 343 |
| 189 | 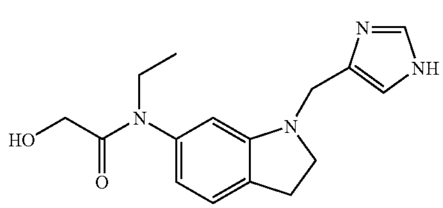 | 301 |

-continued

| Cpd | Structure | MS (MH+) |
|---|---|---|
| 190 | 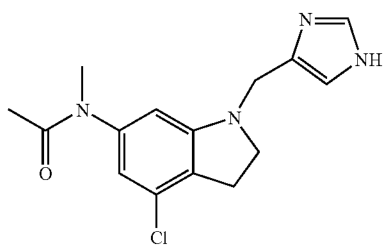 | 305 |
| 191 | 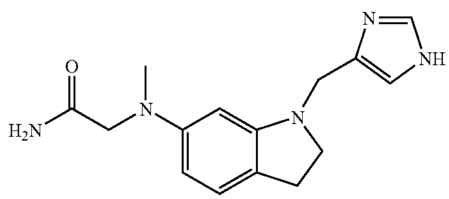 | 286 |
| 192 | 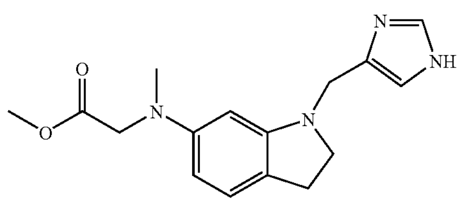 | 301 |
| 193 | 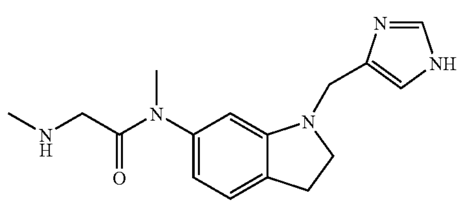 | 300 |
| 194 | 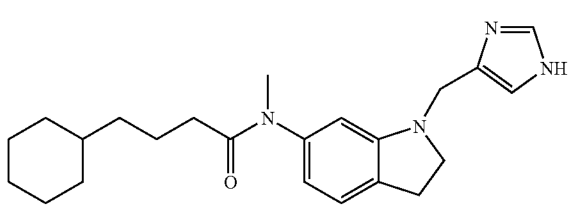 | 381 |
| 195 | 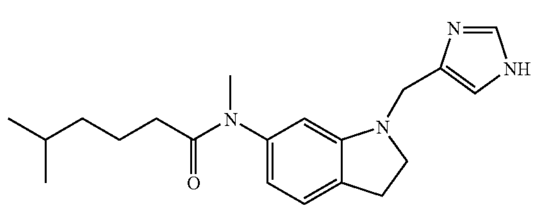 | 341 |
| 196 | 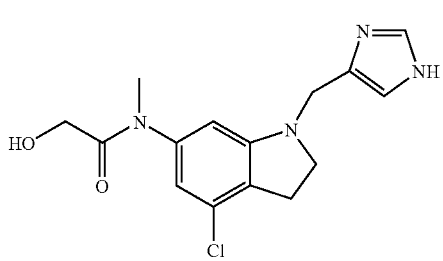 | 321 |

-continued

| Cpd | Structure | MS (MH+) |
|---|---|---|
| 197 | 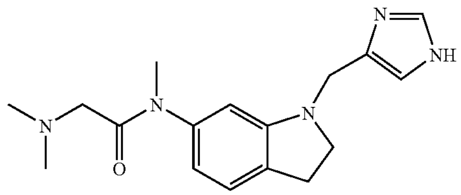 | 314 |
| 198 | 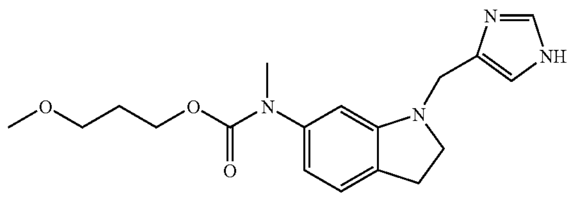 | 345 |
| 199 | 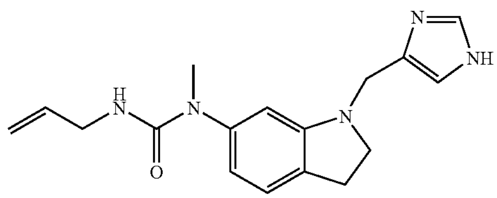 | 312 |
| 200 | 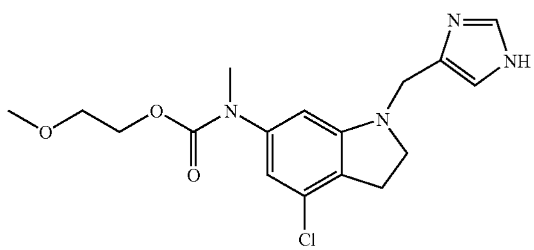 | 365 |
| 201 | 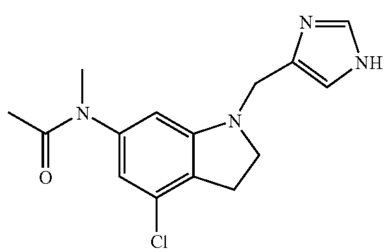 | 305 |

Assay:

Efficacy agonist activity values (Emax, GTPγS assay) for α2A and α2C were determined by following the general procedure detailed by Umland et. al ("Receptor reserve analysis of the human $\alpha_{2c}$-adrenoceptor using [$^{35}$S]GTPγS and cAMP functional assays" European Journal of Pharmacology 2001, 411, 211-221). For the purposes of the present invention, a compound is defined to be a specific or at least selective agonist of the α2C receptor subtype if the compound's efficacy at the α2C receptor is ≧30% Emax (GTPγS assay) and it's efficacy at the α2A receptor is ≦30% Emax (GTPγS assay).

The following compounds were evaluated to be specific or at least selective agonists of the α2C receptor subtype based on the previously defined definition: 1G, 1H, 1I, 2G, 3, 5C, 5D, 6, 7, 7D, 7F, 7G, 7H, 7I, 7N, 10, 11, 11C, 12, 12B, 12D, 14, 15, 17B, 21, 23C, 30, 32, 39, 43, 45, 46, 113, 114, 115, 120, 122, 123, 124, 125, 128, 129, 132, 142, 146, 151, 168, 169, 170, 171, 174, 175, 186, and 187.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by the structural formula:

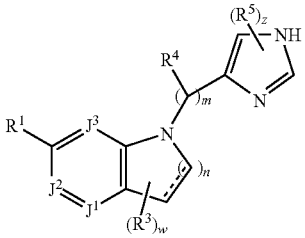

Formula III or a pharmaceutically acceptable salt of said compound, wherein:

$J^1$, $J^2$ and $J^3$ are —C($R^2$)—;

----- is a single or double bond;

$R^1$ is —(CH$_2$)$_q$NR$^7$YR$^{7'}$;

Y is selected from the group consisting of —C(=O)—, —C(=O)NR$^7$—, —C(=O)O—, —C(=NR$^7$)NR$^{7'}$—, —S(O)$_p$—, and —SO$_2$NR$^7$;

$R^2$ is independently selected from the group consisting of H, —OH, halo, and —CN, and alkyl and alkoxy optionally substituted with at least one $R^5$;

$R^3$ is independently selected from the group consisting of H and alkyl and alkoxy optionally substituted with at least one $R^5$;

$R^4$ is independently selected from the group consisting of H and alkyl;

$R^5$ is independently selected from the group consisting of H, halo, —OH, —CN, —NO$_2$, —NR$^7$R$^{7'}$, and —SR$^7$, and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl groups, each of which is optionally substituted with at least one of halo, —OH, —CN, —NO$_2$, —NR$^7$R$^{7'}$, and —S(O)$_p$R$^7$ substituents;

$R^7$ is independently selected from the group consisting of H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N(R$^{11}$)$_2$ and —S(O)$_p$R$^{11}$ substituents;

$R^{7'}$ is independently selected from the group consisting of selected from the group consisting of H and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —SR$^{11}$ substituents;

$R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

m is 1-5;

n is 1;

p is 0-2;

q is 0;

w is 1-3; and z is 0.

2. A compound according to claim 1, which is represented by the structural formula:

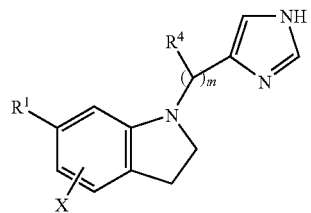

or a pharmaceutically acceptable salt or solvate of said compound, wherein:

X is H or halo;

$R^1$ is —(CH$_2$)$_q$NR$^7$YR$^{7'}$;

Y is selected from the group consisting of a —C(=O)NR$^7$— and —C(=O)O—;

$R^4$ is independently selected from the group consisting of H and alkyl, $R^7$ is independently selected from the group consisting of H and alkyl, alkenyl, alkynyl, cycloalkyl, aryl, arylalkyl, heterocyclyl, heteroaryl, and heteroarylalkyl groups, each of which is optionally substituted with at least one of halo, alkoxy, —OH, —CN, —NO$_2$, —N(R$^{11}$)$_2$ and —S(O)$_p$R$^{11}$ substituents;

$R^{7'}$ is independently selected from the group consisting of selected from the group consisting of H and alkyl, alkenyl, alkynyl, cycloalkyl, aryl, arylalkyl, heteroaryl, and heteroarylalkyl groups, each of which is optionally substituted with at least one of halo, —OH, —CN, —NO$_2$, —N(R$^{11}$)$_2$, and —SR$^{11}$ substituents; or $R^{11}$ is a moiety independently selected from the group consisting of H and alkyl, alkoxy, alkenyl, alkenyloxy, alkynyl, cycloalkyl, cycloalkoxy, aryl, aryloxy, arylalkyl, heteroaryl, heteroarylalkyl, heterocyclyl, and heterocyclylalkyl;

m is 1-5;

p is 0-2; and q is 0;

or a pharmaceutically acceptable salt of said compound.

3. The compound of claim 2, wherein m is 1 and $R^4$ is H.

4. A compound that is selected from the group consisting of

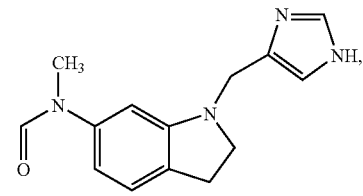

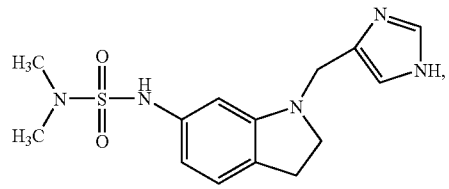

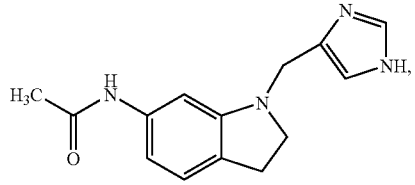

-continued
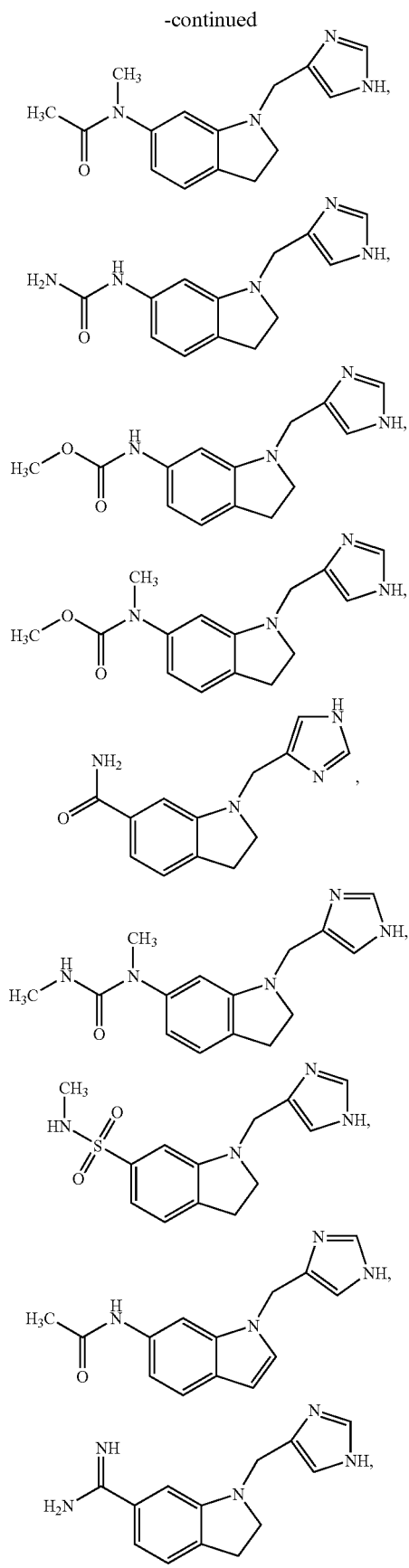
-continued
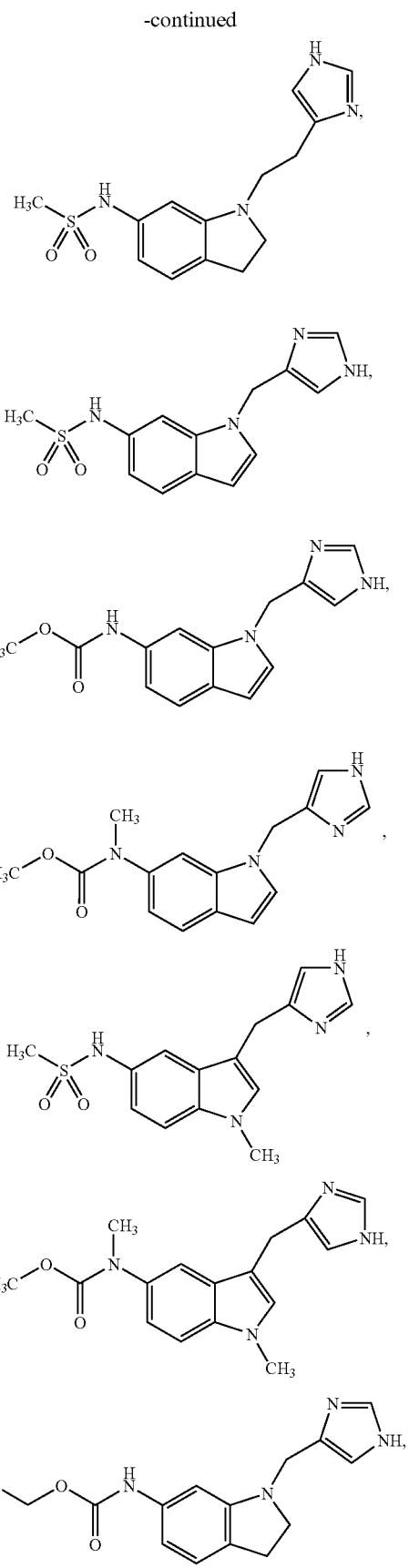

127
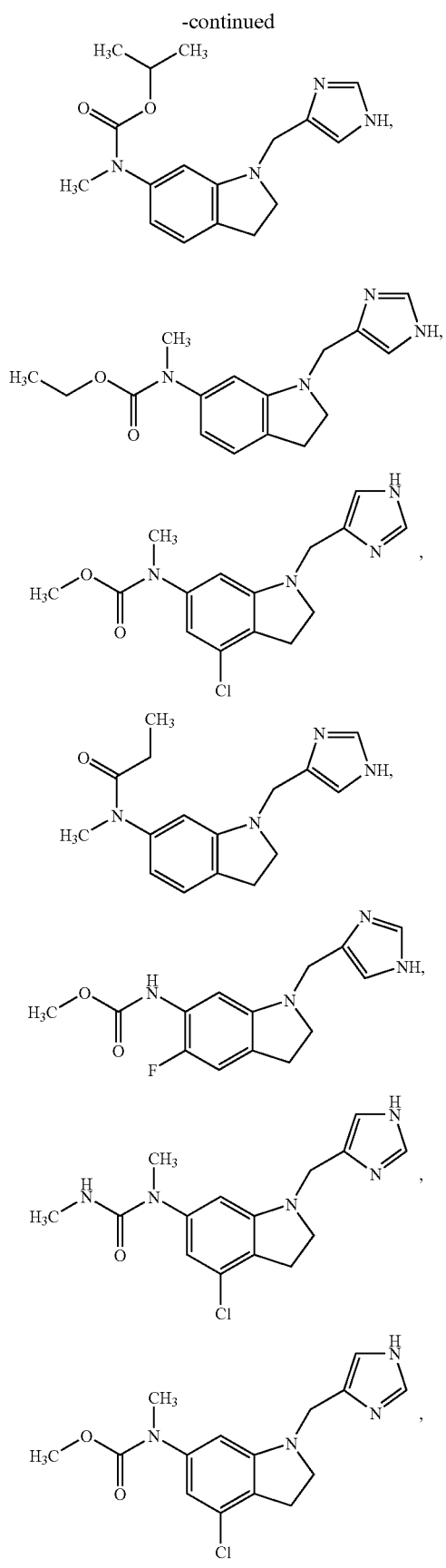
128
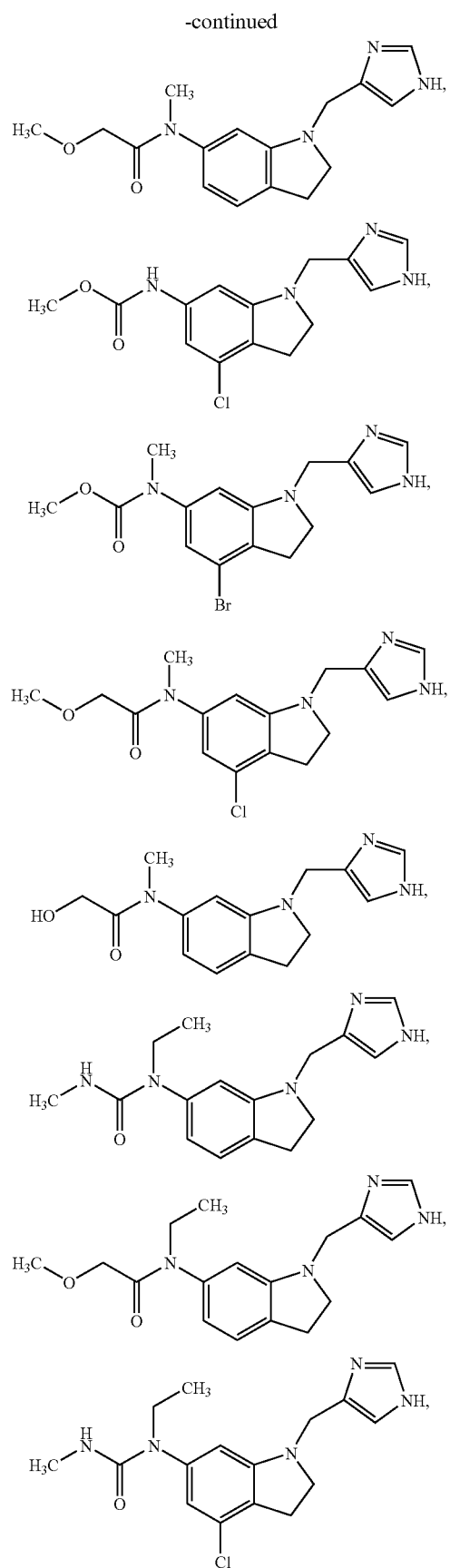

or a pharmaceutically acceptable salt thereof.

5. A compound of claim 1, having the formula:

or a pharmaceutically acceptable salt thereof.

6. A compound of claim 1 having the formula:

or a pharmaceutically acceptable salt thereof.

7. A compound of claim 1 having the formula:

or a pharmaceutically acceptable salt thereof.

8. A compound of claim 1 having the formula:

or a pharmaceutically acceptable salt thereof.

9. A compound of claim 1 having the formula:

or a pharmaceutically acceptable salt thereof.

10. A compound of claim 1, in isolated and purified form.

11. A solid pharmaceutical composition comprising at least one compound of claim 1, or a pharmaceutically acceptable salt and at least one pharmaceutically acceptable carrier, adjuvant or vehicle.

12. A solid pharmaceutical composition comprising at least one compound of claim 4, or a pharmaceutically acceptable salt and at least one pharmaceutically acceptable carrier, adjuvant or vehicle.

13. The pharmaceutical composition of claim 11, additionally further comprising one or more additional therapeutic agents.

14. The pharmaceutical composition of claim 12, additionally further comprising one or more additional therapeutic agents.

15. The pharmaceutical composition of claim 13, wherein said additional therapeutic agents are selected from the group consisting of steroids, PDE-4 inhibitors, anti-muscarinic agents, cromolyn sodium, $H_1$ receptor antagonists NSAIDs, angiotensin-converting enzyme inhibitors, angiotensin II receptor agonists, β-blockers, β-agonists, leukotriene antagonists, diuretics, aldosterone antagonists, ionotropic agents, pain management agents, anti-anxiety agents, and anti-migraine agents.

16. The pharmaceutical composition of claim 14, wherein said additional therapeutic agents are selected from the group consisting of steroids, PDE-4 inhibitors, anti-muscarinic agents, cromolyn sodium, $H_1$ receptor antagonists, NSAIDs, angiotensin-converting enzyme inhibitors, angiotensin II receptor agonists, β-blockers, β-agonists, leukotriene antagonists, diuretics, aldosterone antagonists, ionotropic agents, pain management agents, anti-anxiety agents, and anti-migraine agents.

17. The pharmaceutical composition according to claims 13 wherein therapeutic agents are selected from the group consisting of $5\text{-}HT_1$ agonists, natriuretic peptides, therapeutic agents suitable for treating heart conditions, psychotic disorders, and glaucoma.

* * * * *